(12) United States Patent
Comer et al.

(10) Patent No.: US 9,428,507 B2
(45) Date of Patent: Aug. 30, 2016

(54) COMPOUNDS FOR THE TREATMENT OF MALARIA

(71) Applicants: The Broad Institute, Inc., Cambridge, MA (US); President and Fellows of Harvard College, Cambridge, MA (US)

(72) Inventors: Eamon Comer, Watertown, MA (US); Benito Munoz, Newtonville, MA (US); Jennifer A. Beaudoin, Holden, MA (US); Sebastian T. Le Quement, Cambridge, MA (US); Christina Scherer, Concord, MA (US); Jeremy Duvall, Wakefield, MA (US); Nobutaka Kato, Cambridge, MA (US); Micah Maetani, Cambridge, MA (US); Bertrand Braibant, Huningue (FR)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/900,245

(22) PCT Filed: Jun. 20, 2014

(86) PCT No.: PCT/US2014/043463
§ 371 (c)(1),
(2) Date: Dec. 21, 2015

(87) PCT Pub. No.: WO2015/002755
PCT Pub. Date: Jan. 8, 2015

(65) Prior Publication Data
US 2016/0152617 A1    Jun. 2, 2016

Related U.S. Application Data

(60) Provisional application No. 61/837,711, filed on Jun. 21, 2013.

(51) Int. Cl.
*A61K 31/535* (2006.01)
*C07D 471/20* (2006.01)
*C07D 498/22* (2006.01)

(52) U.S. Cl.
CPC ........... *C07D 471/20* (2013.01); *C07D 498/22* (2013.01)

(58) Field of Classification Search
None
See application file for complete search history.

(56) References Cited

U.S. PATENT DOCUMENTS

| | | |
|---|---|---|
| 2008/0009495 A1 | 1/2008 | Kokubo et al. |
| 2010/0324023 A1 | 12/2010 | Selnick et al. |
| 2013/0109699 A1 | 5/2013 | Ohata et al. |

FOREIGN PATENT DOCUMENTS

JP    EP 1142587 A1 * 10/2001 ............. A61K 31/00

OTHER PUBLICATIONS

Buinauskaite et al., "Facile synthesis of spiro[benzo[e]indole-2,2'-piperidine] derivatives and their transformation to novel fluorescent scaffolds," Tetrahedron. 68:9260-6 (2012).
International Search Report and Written Opinion for International Patent Application No. PCT/US14/43463, mailed Dec. 22, 2014 (8 pages).
Xie et al., "A convenient synthesis of 1'-H-spiro-(indoline-3,4'-piperidine) and its derivatives," Tetrahedron. 60:4875-8 (2004).

* cited by examiner

*Primary Examiner* — Dennis Heyer
*Assistant Examiner* — Daniel M Podgorski
(74) *Attorney, Agent, or Firm* — Melissa Hunter-Ensor; Elbert C. Chiang; Greenberg Traurig, LLP

(57) ABSTRACT

Provided herein are compounds of the formula (I): as well as pharmaceutically acceptable salts thereof, wherein the substituents are as those disclosed in the specification. These compounds, and the pharmaceutical compositions containing them, are useful for the treatment of malaria.

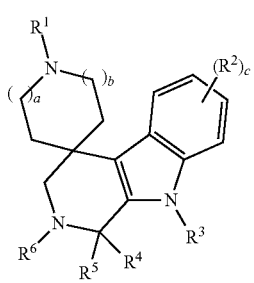

(I)

21 Claims, 1 Drawing Sheet

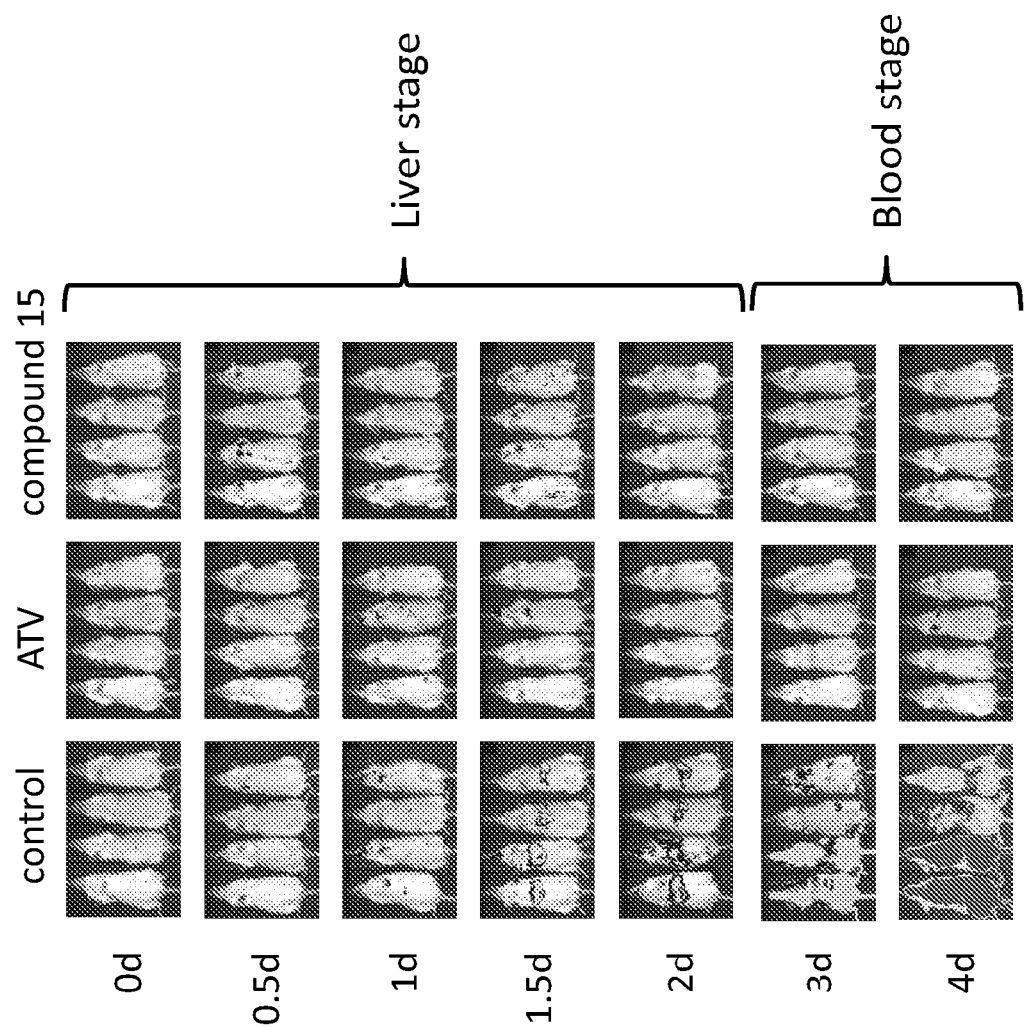

COMPOUNDS FOR THE TREATMENT OF MALARIA

CROSS-REFERENCE TO RELATED APPLICATIONS

This application claims benefit of U.S. Provisional Application No. 61/837,711, filed Jun. 21, 2013, which is incorporated herein by reference in its entirety.

BACKGROUND OF THE INVENTION

Malaria is a vector-borne infectious disease caused by protozoan parasites and is widespread in tropical and sub-tropical regions, including parts of the Americas, Asia, and Africa. Of the five *Plasmodium* parasite species that can infect humans (*P. falciparum, P. vivax, P. ovale, P. malariae*, and *P. knowlesi*), the most serious forms of the disease are caused by *P. falciparum* and *P. vivax*. Of the approximately 515 million people infected yearly, between one and three million people, the majority of whom are young children in Sub-Saharan Africa, die from the disease. The current armament of approved anti-malarial drugs, such as chloroquine, atovaquone, pyrimethamine, and sulfadoxine, is limited to only a few targets within the human malaria parasite, and growing widespread resistance to current drugs is prompting the development of new antimalarial agents that have new biological targets.

SUMMARY OF THE INVENTION

The invention features a compound having the structure:

Formula I wherein a and b are independently 0, 1, or 2;

c is 0, 1, 2, 3, or 4;

$R^1$ is hydrogen, $C_1$-$C_6$ alkyl, $C_2$-$C_9$ heteroaryl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, —C(O)NR$^7$R$^8$, —C(O)OR$^9$, —C(O)R$^{10}$, or —S(O)$_2$R$^{11}$;

each $R^2$ is independently hydroxyl, halogen, or —OR$^{12}$;

$R^3$ is hydrogen or $C_1$-$C_6$ alkyl;

$R^4$ is hydrogen or $C_1$-$C_6$ alkyl;

$R^5$ is $C_1$-$C_6$ alkyl, or —(CH$_2$)$_n$X$^1$R$^{13}$, or $R^5$ and $R^6$ together with the carbon and nitrogen atoms to which they are respectively attached, combine to form a 5-8-membered heterocycle;

$R^6$ is hydrogen, $C_1$-$C_6$ alkyl, $C_1$-$C_6$ perfluoroalkyl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, $C_2$-$C_9$ heterocyclyl $C_1$-$C_6$ alkyl, N-protecting group, —C(O)R$^{15}$, —C(O)NR$^{16}$R$^{17}$, or —S(O)$_2$R$^{18}$;

$R^7$ is hydrogen or $C_1$-$C_6$ alkyl;

$R^8$ is $C_6$-$C_{10}$ aryl, $C_2$-$C_9$ heteroaryl, $C_2$-$C_9$ heterocyclyl, or $C_3$-$C_{10}$ carbocyclyl;

$R^9$ is $C_1$-$C_6$ alkyl or $C_6$-$C_{10}$ aryl;

$R^{10}$ is $C_1$-$C_6$ alkyl, $C_6$-$C_{10}$ aryl, $C_2$-$C_9$ heterocyclyl, $C_6$-$C_{10}$ aryl $C_1$-$C_6$ alkyl, or $C_2$-$C_9$ heteroaryl $C_1$-$C_6$ alkyl;

$R^{11}$ is $C_1$-$C_6$ alkyl, $C_6$-$C_{10}$ aryl, or $C_6$-$C_{10}$ aryl $C_1$-$C_6$ alkyl;

each $R^{12}$ is $C_1$-$C_6$ alkyl or $C_1$-$C_6$ acyl;

n is 1, 2, 3, 4, 5, or 6;

$X^1$ is absent, O, or NR$^{14}$;

$R^{13}$ is hydrogen, $C_1$-$C_6$ alkyl, $C_1$-$C_6$ heteroalkyl, $C_1$-$C_6$ perfluoroalkyl, $C_1$-$C_6$ acyl, $C_6$-$C_{10}$ aryl $C_1$-$C_6$ alkyl, an O- or N-protecting group, or $R^{13}$ and $R^{14}$ combine to form a 5-8-membered heterocycle;

$R^{14}$ is hydrogen or $C_1$-$C_6$ alkyl;

$R^{15}$ is $C_1$-$C_6$ alkyl, $C_1$-$C_6$ perfluoroalkyl, $C_1$-$C_6$ heteroalkyl, $C_3$-$C_{10}$ carbocyclyl, $C_2$-$C_9$ heterocyclyl, $C_6$-$C_{10}$ aryl, $C_6$-$C_{10}$ aryl $C_1$-$C_6$ alkyl;

$R^{16}$ and $R^{17}$ are independently hydrogen, $C_1$-$C_6$ alkyl, or $C_6$-$C_{10}$ aryl; and $R^{18}$ is $C_1$-$C_6$ alkyl, $C_1$-$C_6$ perfluoroalkyl, $C_3$-$C_{10}$ carbocyclyl, or $C_6$-$C_{10}$ aryl; or a pharmaceutically acceptable salt thereof, wherein the compound is not compound 12, compound 15, or any one of compounds 78-135 of Table 1 or a pharmaceutically acceptable salt thereof.

In some embodiments, c is 1. In other embodiments, c is 2.

In certain embodiments, the compound has a structure of Formula II:

Formula II

In other embodiments, the compound has a structure of Formula III:

Formula III

In some embodiments, the compound has a structure of Formula IV:

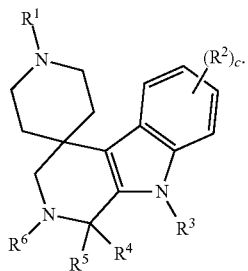

Formula IV

In certain embodiments, the compound has the structure:

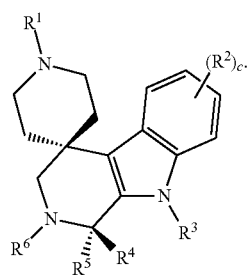

In other embodiments, the compound has a structure of Formula V:

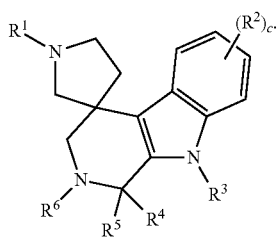

Formula V

In certain embodiments, the compound has the structure:

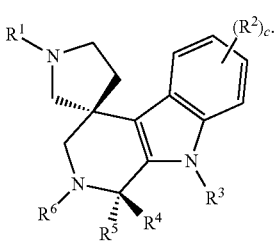

In some embodiments, the compound has a structure of Formula VI:

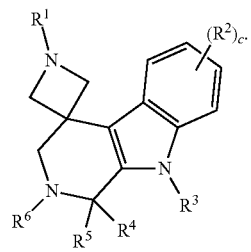

Formula VI

In certain embodiments, the compound has the structure:

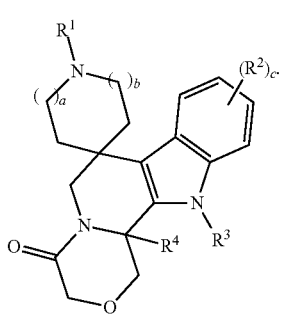

In some embodiments, $R^3$ is hydrogen. In other embodiments, $R^3$ is $C_1$-$C_6$ alkyl (e.g., methyl). In certain embodiments, $R^4$ is hydrogen. In some embodiments, $R^4$ is $C_1$-$C_6$ alkyl (e.g., methyl).

In other embodiments, $R^2$ is hydroxyl. In certain embodiments, $R^2$ is halogen (e.g., fluoro). In some embodiments, $R^2$ is —$OR^{12}$ (e.g., $R^{12}$ is $C_1$-$C_6$ alkyl, such as methyl or isopropyl or $C_1$-$C_6$ acyl, such as acetyl).

In certain embodiments, $R^5$ and $R^6$ together with the carbon and nitrogen atoms to which they are respectively attached, combine to form a 5-8-membered heterocycle (e.g., a 6-membered heterocycle substituted with an oxo).

In some embodiments, the compound has the structure of Formula VII:

Formula VII

In other embodiments, $R^5$ is $C_1$-$C_6$ alkyl (e.g., methyl).

In certain embodiments, $R^5$ is —$(CH_2)_nX^1R^{13}$. In some embodiments, n is 1. In other embodiments, n is 2. In certain embodiments, $X^1$ is absent. In some embodiments, $R^{13}$ is $C_1$-$C_6$ perfluoroalkyl (e.g., trifluoromethyl). In other embodiments, $X^1$ is O. In certain embodiments, $R^{13}$ is hydrogen, $C_1$-$C_6$ alkyl (e.g., methyl), $C_1$-$C_6$ heteroalkyl (e.g., —$CH_2OCH_3$ or —$CH_2OCH_2CH_2OCH_3$), $C_1$-$C_6$ acyl (e.g., acetyl), $C_6$-$C_{10}$ aryl $C_1$-$C_6$ alkyl (e.g., 4-methoxybenzyl), or an O-protecting group (e.g., tertbutyldimethylsilyl). In some embodiments, $X^1$ is $NR^{14}$. In other embodiments, $R^{13}$ and $R^{14}$ combine to form a 5-8-membered heterocycle (e.g., morpholino). In certain embodiments, $R^{14}$ is hydrogen. In some embodiments, $R^{14}$ is $C_1$-$C_6$ alkyl (e.g., methyl). In some embodiments, $R^{13}$ is $C_1$-$C_6$ alkyl (e.g., methyl).

In other embodiments, $R^1$ is hydrogen.

In certain embodiments, $R^1$ is $C_1$-$C_6$ alkyl (e.g., methyl, ethyl, or n-propyl).

In some embodiments, $R^1$ is $C_2$-$C_9$ heteroaryl (e.g., benzo-oxazolyl, benzo-imidazolyl, or benzo-thiazolyl).

In other embodiments, $R^1$ is $C_3$-$C_{10}$ carbocyclyl $C_1$-$C_6$ alkyl (e.g., cyclopropylmethyl, cyclopentylmethyl, or cyclohexylmethyl).

In certain embodiments, $R^1$ is $C_6$-$C_{10}$ aryl $C_1$-$C_6$ alkyl (e.g., 2-fluorophenyl-ethyl, 2-fluorobenzyl, 4-(2-pyridyl)-benzyl, 4-methoxybenzyl, or 3-fluorobenzyl).

In some embodiments, $R^1$ is $C_2$-$C_9$ heteroaryl $C_1$-$C_6$ alkyl (e.g., 2-pyridyl-methyl, 3-pyridyl-methyl, 3,5-pyrimidyl-methyl, thiazolyl-methyl, or (3-phenyl-oxazolyl)-methyl).

In other embodiments $R^1$ is —C(O)NR$^7$R$^8$. In certain embodiments, $R^7$ is hydrogen. In some embodiments, $R^7$ is $C_1$-$C_6$ alkyl (e.g., methyl). In some embodiments, $R^8$ is $C_6$-$C_{10}$ aryl (e.g., 2-chlorophenyl, 2-fluorophenyl, 2-trifluoromethylphenyl, 3-chlorophenyl, 3-fluorophenyl, 4-fluorophenyl, 4-chlorophenyl, 4-methoxyphenyl, 2,3-difluorophenyl, 2,4-difluorophenyl, 2,5-difluorophenyl, 2,6-difluorophenyl, or 3,4-difluorophenyl). In other embodiments, $R^8$ is $C_2$-$C_9$ heteroaryl (e.g., 2-pyridyl or 3-pyridyl). In certain embodiments, $R^8$ is $C_2$-$C_9$ heterocyclyl (e.g., benzodioxolyl). In some embodiments, $R^8$ is $C_3$-$C_{10}$ carbocyclyl (e.g., cyclohexyl).

In other embodiments, $R^1$ is —C(O)OR$^9$. In certain embodiments, $R^9$ is $C_1$-$C_6$ alkyl (e.g., tertbutyl). In some embodiments, $R^9$ is $C_6$-$C_{10}$ aryl (e.g., 4-nitrophenyl).

In other embodiments, $R^1$ is —C(O)R$^{10}$. In certain embodiments, $R^{10}$ is $C_1$-$C_6$ alkyl (e.g., ethyl or n-propyl). In some embodiments, $R^{10}$ is $C_6$-$C_{10}$ aryl (e.g., phenyl or 2-fluorophenyl). In other embodiments, $R^{10}$ is $C_2$-$C_9$ heterocyclyl (e.g., benzodioxolyl). In certain embodiments, $R^{10}$ is $C_6$-$C_{10}$ aryl $C_1$-$C_6$ alkyl (e.g., 2-fluorobenzyl). In some embodiments, $R^{10}$ is $C_2$-$C_9$ heteroaryl $C_1$-$C_6$ alkyl (e.g., 3-pyridylmethyl).

In other embodiments, $R^1$ is —S(O)$_2$R$^{11}$. In certain embodiments, $R^{11}$ is $C_1$-$C_6$ alkyl (e.g., ethyl).

In some embodiments, $R^1$ is $C_6$-$C_{10}$ aryl (e.g., phenyl, 2-fluorophenyl, 3-fluorophenyl, 3-methoxyphenyl, or 4-methoxyphenyl). In other embodiments, $R^{11}$ is $C_6$-$C_{10}$ aryl $C_1$-$C_6$ alkyl (e.g., 2-fluorobenzyl).

In certain embodiments, $R^6$ is hydrogen. In some embodiments, $R^6$ is $C_1$-$C_6$ alkyl (e.g., methyl, ethyl, n-propyl, or 2,2,2-trifluoroethyl). In certain embodiments, $R^6$ is $C_3$-$C_{10}$ carbocyclyl $C_1$-$C_6$ alkyl (e.g., cyclopropylmethyl or cyclohexylmethyl). In some embodiments, $R^6$ is $C_6$-$C_{10}$ aryl $C_1$-$C_6$ alkyl (e.g., benzyl, 2-methoxybenzyl, 3-methoxybenzyl, 4-chlorobenzyl, 2,5-difluorobenzyl, phenyl-ethyl, or phenyl-propyl). In other embodiments, $R^6$ is $C_2$-$C_9$ heteroaryl $C_1$-$C_6$ alkyl (e.g., 2-pyridyl-methyl). In certain embodiments, $R^6$ is $C_2$-$C_9$ heterocyclyl $C_1$-$C_6$ alkyl (e.g., benzodioxolyl-methyl). In some embodiments, $R^6$ is an N-protecting group (e.g., allyloxycarbonyl, i.e., alloc).

In other embodiments, $R^6$ is —C(O)R$^{15}$. In certain embodiments, $R^{15}$ is $C_1$-$C_6$ alkyl (e.g., methyl, ethyl, n-propyl, isopropyl, or tertbutyl). In some embodiments, $R^{15}$ is $C_1$-$C_6$ perfluoroalkyl (e.g., trifluoromethyl). In other embodiments, $R^{15}$ is $C_1$-$C_6$ heteroalkyl (e.g., —CH$_2$N(CH$_3$)$_2$). In certain embodiments, $R^{15}$ is $C_3$-$C_{10}$ carbocyclyl (e.g., cyclopropyl, cyclobutyl, cyclopentyl, or cyclohexyl). In some embodiments, $R^{15}$ is $C_2$-$C_9$ heterocyclyl (e.g., pyranyl). In other embodiments, $R^{15}$ is $C_6$-$C_{10}$ aryl (e.g., phenyl or 4-fluorophenyl). In certain embodiments, $R^{15}$ is $C_6$-$C_{10}$ aryl $C_1$-$C_6$ alkyl (e.g., benzyl).

In some embodiments, $R^6$ is —C(O)NR$^{16}$R$^{17}$. In other embodiments, $R^{16}$ is hydrogen. In certain embodiments, $R^{17}$ is $C_6$-$C_{10}$ aryl (e.g., 4-fluorophenyl).

In some embodiments, $R^6$ is —S(O)$_2$R$^{18}$. In other embodiments, $R^{18}$ is $C_1$-$C_6$ alkyl (e.g., methyl, ethyl, or n-propyl). In certain embodiments, $R^{18}$ is $C_1$-$C_6$ perfluoroalkyl (e.g., trifluoromethyl). In some embodiments, $R^{18}$ is $C_3$-$C_{10}$ carbocyclyl (e.g., cyclopropyl). In other embodiments, $R^{18}$ is $C_6$-$C_{10}$ aryl (e.g., phenyl or 4-methylphenyl).

In another aspect, the invention features a compound selected from any one of compounds 1 to 11, 13, 14, 16 to 77, and 136 to 150 of Table 1 or a pharmaceutically acceptable salt thereof.

TABLE 1

Selected Compounds of the Invention

| Example Number | Structure | Name |
|---|---|---|
| 1 | 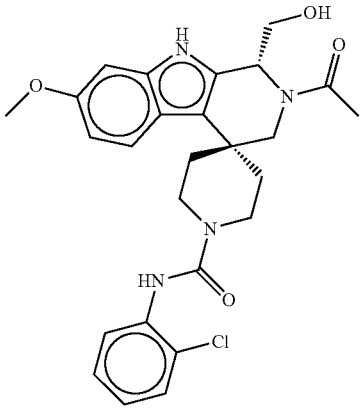 | (R)-2'-acetyl-N-(2-chlorophenyl)-1'-(hydroxymethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 2 | 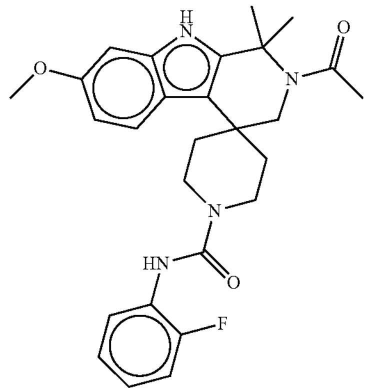 | 2'-acetyl-N-(2-fluorophenyl)-7'-methoxy-1',1'-dimethyl-1',2',3',9'-tetrahydrospiro[piperidine-4,4'-pyrido[3,4-b]indole]-1-carboxamide |
| 3 | 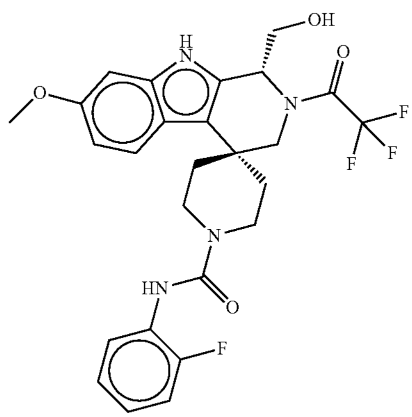 | (R)-N-(2-fluorophenyl)-1'-(hydroxymethyl)-7'-methoxy-2'-(2,2,2-trifluoroacetyl)-1',2',3',9'-tetrahydrospiro[piperidine-4,4'-pyrido[3,4-b]indole]-1-carboxamide |
| 4 | 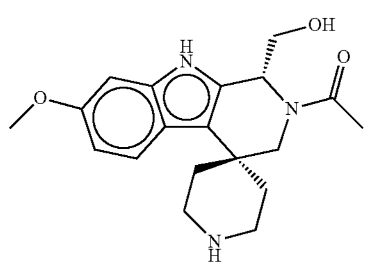 | (R)-1-(1'-(hydroxymethyl)-7'-methoxyspiro[piperidine-4,4'-pyrido[3,4-b]indol]-2'(1'H,3'H,9'H)-yl)ethanone |
| 5 | 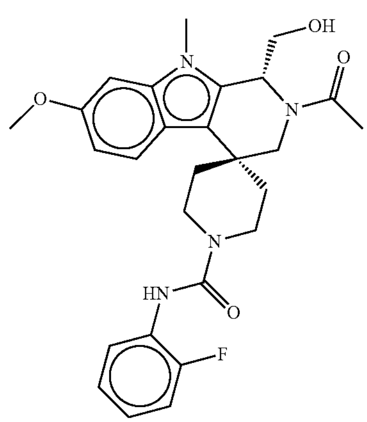 | (R)-2'-acetyl-N-(2-fluorophenyl)-1'-(hydroxymethyl)-7'-methoxy-9'-methyl-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 6 | 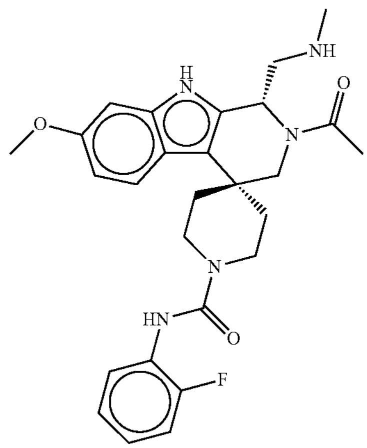 | (S)-2'-acetyl-N-(2-fluorophenyl)-7'-methoxy-1'-((methylamino)methyl)-1',2',3',9'-tetrahydrospiro[piperidine-4,4'-pyrido[3,4-b]indole]-1-carboxamide |
| 7 | 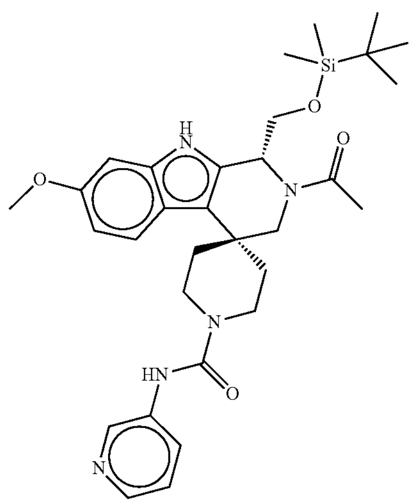 | (R)-2'-acetyl-1'-(((tert-butyldimethylsilyl)oxy)methyl)-7'-methoxy-N-(pyridin-3-yl)-1',2',3',9'-tetrahydrospiro[piperidine-4,4'-pyrido[3,4-b]indole-carboxamide |
| 8 | 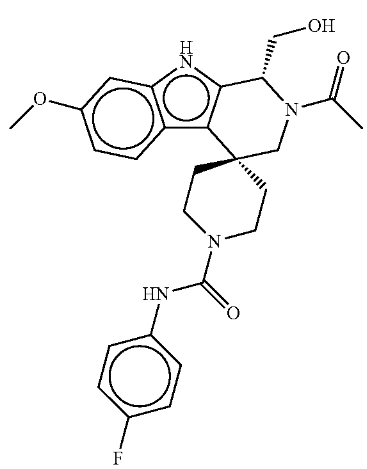 | (R)-2'-acetyl-N-(4-fluorophenyl)-1'-(hydroxymethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 9 | 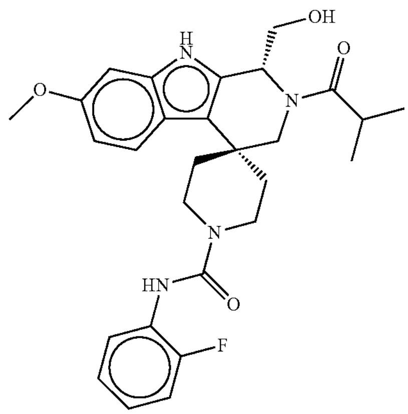 | (R)-N-(2-fluorophenyl)-1'-(hydroxymethyl)-2'-isobutyryl-7'-methoxy-1',2',3',9'-tetrahydrospiro[piperidine-4,4'-pyrido[3,4-b]indole-1-carboxamide |
| 10 | 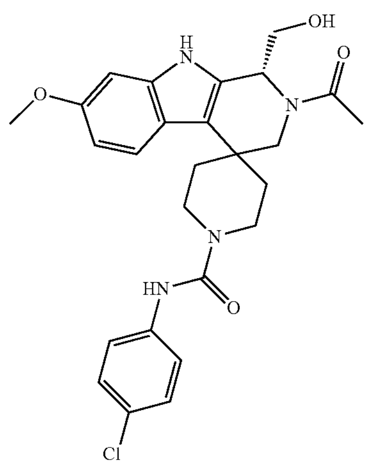 [SMILES: COc1ccc2c3c([nH]c2c1)[C@H](CO)N(C(C)=O)CC31CCN(C(=O)Nc2ccc(Cl)cc2)CC1] | (R)-2'-acetyl-N-(4-chlorophenyl)-1'-(hydroxymethyl)-7'-methoxy-1',2',3',9'-tetrahydrospiro[piperidine-4,4'-pyrido[3,4-b]indole-1-carboxamide |
| 11 | 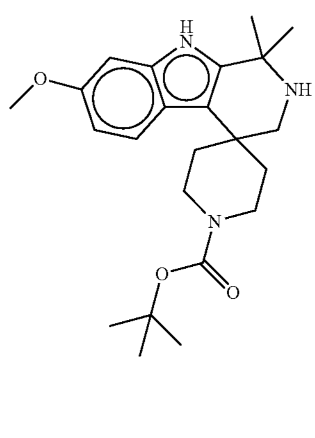 | tert-butyl 7'-methoxy-1',1'-dimethyl-1',2',3',9'-tetrahydrospiro[piperidine-4,4'-pyrido[3,4-b]indole-1-carboxylate |

TABLE 1-continued

Selected Compounds of the Invention

| Example Number | Structure | Name |
|---|---|---|
| 12 | 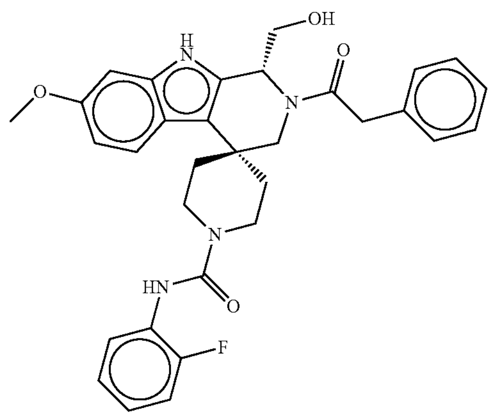 | (R)-N-(2-fluorophenyl)-1'-(hydroxymethyl)-7'-methoxy-2'-(2-phenylacetyl)-1',2',3',9'-tetrahydrospiro[piperidine-4,4'-pyrido[3,4-b]indole-1-carboxamide |
| 13 | 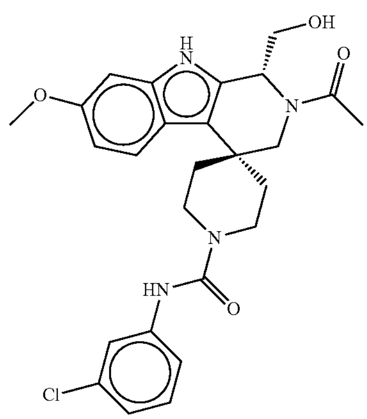 | (R)-2'-acetyl-N-(3-chlorophenyl)-1'-(hydroxymethyl)-7'-methoxy-1',2',3',9'-tetrahydrospiro[piperidine-4,4'-pyrido[3,4-b]indole]-1-carboxamide |
| 14 | 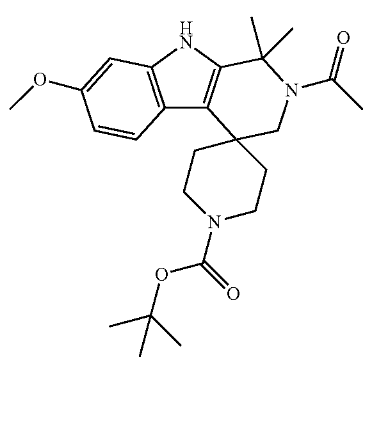 [SMILES: COc1ccc2c3c([nH]c2c1)C(C)(C)N(C(C)=O)CC31CCN(C(=O)OC(C)(C)C)CC1] | tert-butyl 2'-acetyl-7'-methoxy-1',1'-dimethyl-1',2',3',9'-tetrahydrospiro[piperidine-4,4'-pyrido[3,4-b]indole]-1-carboxylate |

TABLE 1-continued

Selected Compounds of the Invention

| Example Number | Structure | Name |
|---|---|---|
| 15 | 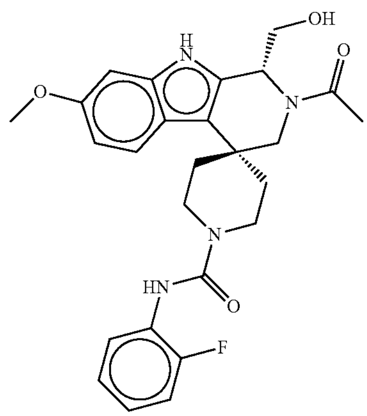 | (R)-2'-acetyl-N-(2-fluorophenyl)-1'-(hydroxymethyl)-7'-methoxy-1',2',3',9'-tetrahydrospiro[piperidine-4,4'-pyrido[3,4-b]indole]-1-carboxamide |
| 16 | 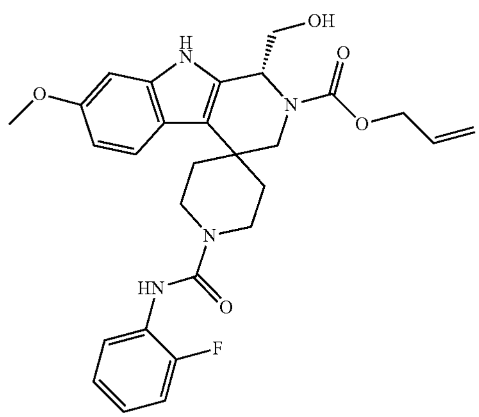 [SMILES: C=CCOC(=O)N1CC2(CCN(C(=O)Nc3ccccc3F)CC2)c2c([nH]c3cc(OC)ccc23)[C@@H]1CO] | (R)-allyl 1-((2-fluorophenyl)carbamoyl)-1'-(hydroxymethyl)-7'-methoxy-3',9'-dihydrospiro[piperidine-4,4'-pyrido[3,4-b]indole]-2'(1'H)-carboxylate |
| 17 | 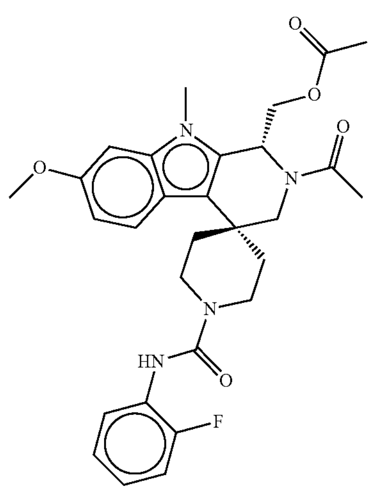 | (R)-(2'-acetyl-1-((2-fluorophenyl)carbamoyl)-7'-methoxy-9'-methyl-1',2',3',9'-tetrahydrospiro[piperidine-4,4'-pyrido[3,4-b]indol-1'-yl)methylacetate |

TABLE 1-continued

Selected Compounds of the Invention

| Example Number | Structure | Name |
|---|---|---|
| 18 | 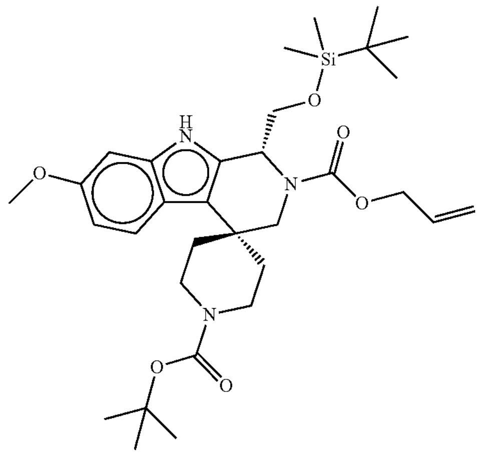 | (R)-2'-allyl 1-tert-butyl 1'-(((tert-butyldimethylsilyl)oxy)methyl)-7'-methoxy-3',9'-dihydrospiro[piperidine-4,4'-pyrido[3,4-b]indole]-1,2'(1'H)-dicarboxylate |
| 19 | 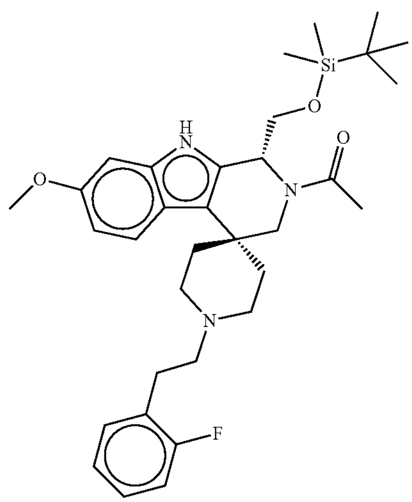 | (R)-1-(1'-(((tert-butyldimethylsilyl)oxy)methyl)-1-(2-fluorophenethyl)-7'-methoxyspiro[piperidine-4,4'-pyrido[3,4-b]indol]-2'(1'H,3'H,9'H)-yl)ethanone |
| 20 | 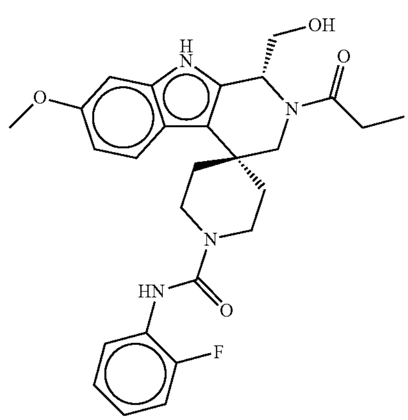 | (R)-N-(2-fluorophenyl)-1'-(hydroxymethyl)-7'-methoxy-2'-propionyl-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 21 | 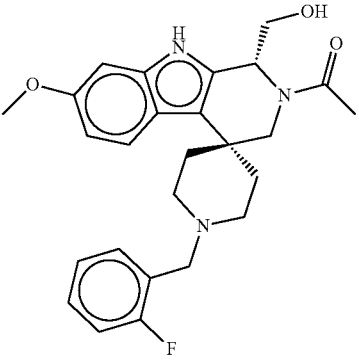 | (R)-1-(1-(2-fluorobenzyl)-1'-(hydroxymethyl)-7'-methoxyspiro[piperidine-4,4'-pyrido[3,4-b]indol]-2'(1'H,3'H,9'H)-yl)ethanone |
| 22 | 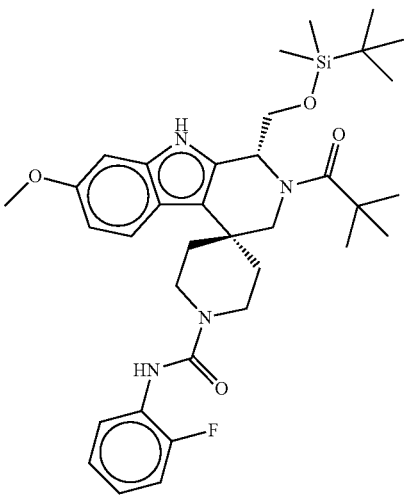 | (R)-1'-(((tert-butyldimethylsilyl)oxy)methyl)-N-(2-fluorophenyl)-7'-methoxy-2'-pivaloyl-1',2',3',9'-tetrahydrospiro[piperidine-4,4'-pyrido[3,4-b]indole]-1-carboxamide |
| 23 | 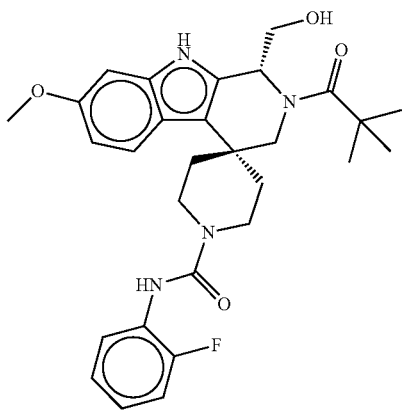 | (R)-N-(2-fluorophenyl)-1'-(hydroxymethyl)-7'-methoxy-2'-pivaloyl-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 24 | 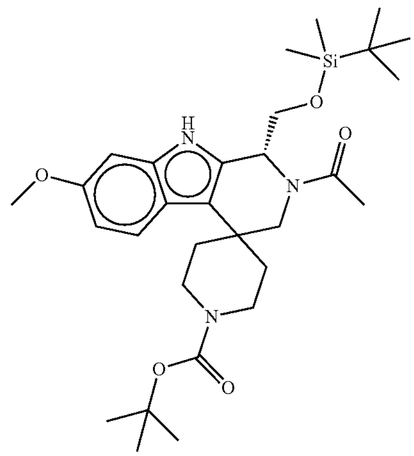 | (R)-tert-butyl 2'-acetyl-1'-(((tert-butyldimethylsilyl)oxy)methyl)-7'-methoxy-1',2',3',9'-tetrahydrospiro[piperidine-4,4'-pyrido[3,4-b]indole]-1-carboxylate |
| 25 | 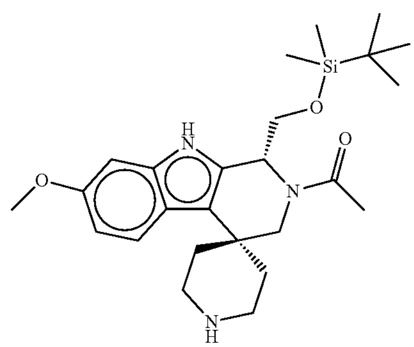 | (R)-1-(1'-(((tert-butyldimethylsilyl)oxy)methyl)-7'-methoxyspiro[piperidine-4,4'-pyrido[3,4-b]indol]-2'(1'H,3'H,9'H)-yl)ethanone |
| 26 | 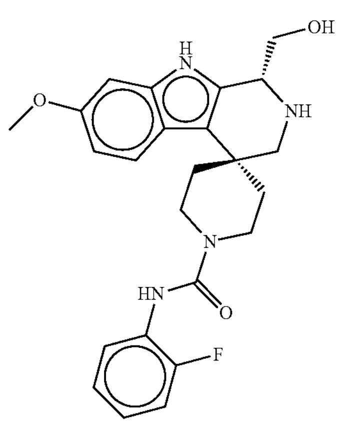 | (R)-N-(2-fluorophenyl)-1'-(hydroxymethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 27 | 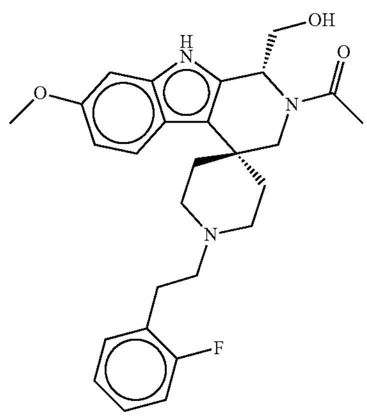 | (R)-1-(1-(2-fluorophenethyl)-1'-(hydroxymethyl)-7'-methoxyspiro[piperidine-4,4'-pyrido[3,4-b]indol]-2'(1'H,3'H,9'H)-yl)ethanone |
| 28 | 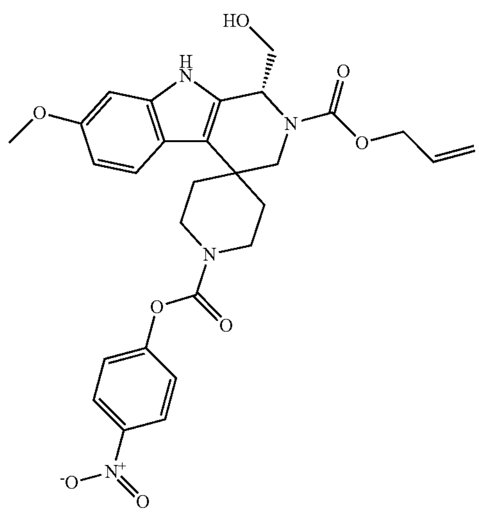 | (R)-2'-allyl 1-(4-nitrophenyl) 1'-(hydroxymethyl)-7'-methoxy-3',9'-dihydrospiro[piperidine-4,4'-pyrido[3,4-b]indole]-1,2'(1'H)-dicarboxylate |
| 29 | 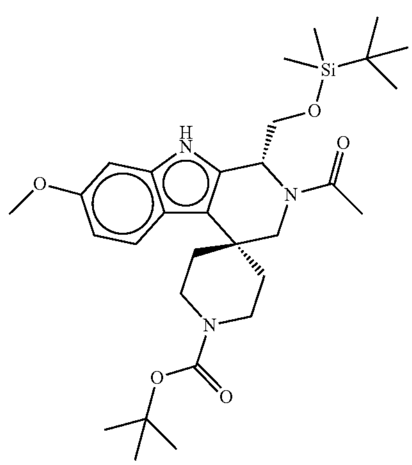 | (R)-tert-butyl 2'-acetyl-1'-(((tert-butyldimethylsilyl)oxy)methyl)-7'-methoxy-1',2',3',9'-tetrahydrospiro[piperidine-4,4'-pyrido[3,4-b]indole]-1-carboxylate |

TABLE 1-continued

Selected Compounds of the Invention

| Example Number | Structure | Name |
|---|---|---|
| 30 | 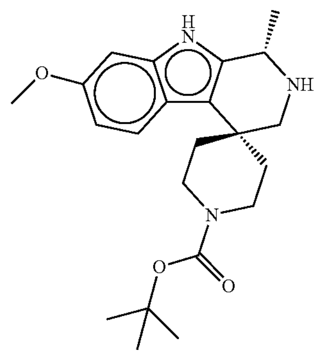 | (S)-tert-butyl 7'-methoxy-1'-methyl-1',2',3',9'-tetrahydrospiro[piperidine-4,4'-pyrido[3,4-b]indole]-1-carboxylate |
| 31 | 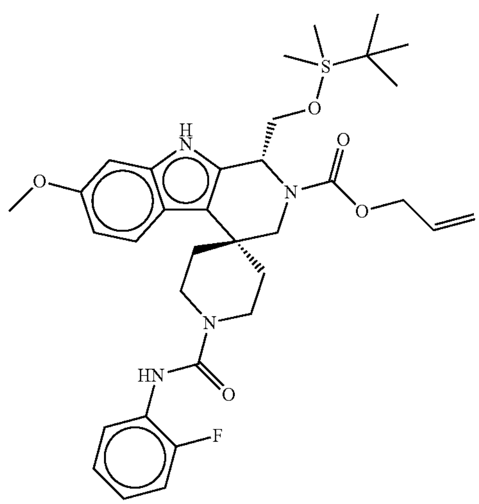 | (R)-allyl 1'-(((tert-butyldimethylsilyoxy)methyl)-1-((2-fluorophenyl)carbamoyl)-7'-methoxy-3',9'-dihydrospiro[piperidine-4,4'-pyrido[3,4-b]indole]-2'(1'H)-carboxylate |
| 32 | 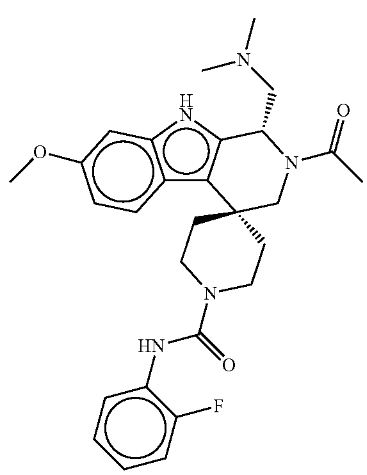 | (S)-2'-acetyl-1'-((dimethylamino)methyl)-N-(2-fluorophenyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 33 | 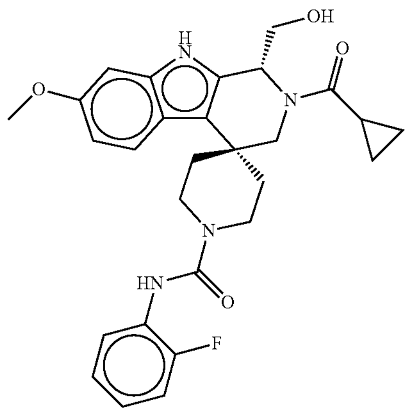 | (R)-2'-(cyclopropanecarbonyl)-N-(2-fluorophenyl)-1'-(hydroxymethyl)-7'-methoxy-1',2',3',9'-tetrahydrospiro[piperidine-4,4'-pyrido[3,4-b]indole]-1-carboxamide |
| 34 | 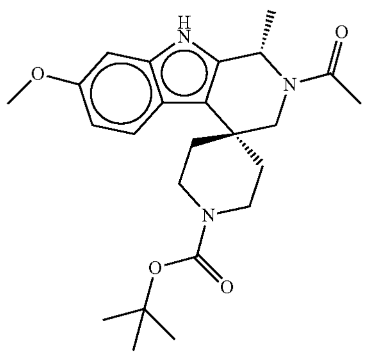 | (S)-tert-butyl 2'-acetyl-7'-methoxy-1'-methyl-1',2',3',9'-tetrahydrospiro[piperidine-4,4'-pyrido[3,4-b]indole]-1-carboxylate |
| 35 | 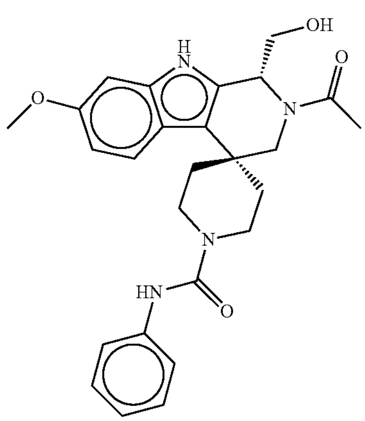 | (R)-2'-acetyl-1'-(hydroxymethyl)-7'-methoxy-N-phenyl-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 36 | 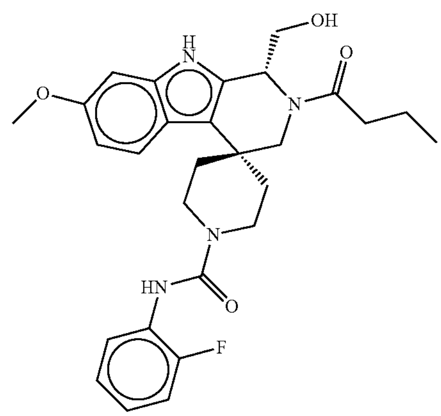 | (R)-2'-butyryl-N-(2-fluorophenyl)-1'-(hydroxymethyl)-7'-methoxy-1',2',3',9'-tetrahydrospiro[piperidine-4,4'-pyrido[3,4-b]indole]-1-carboxamide |
| 37 | 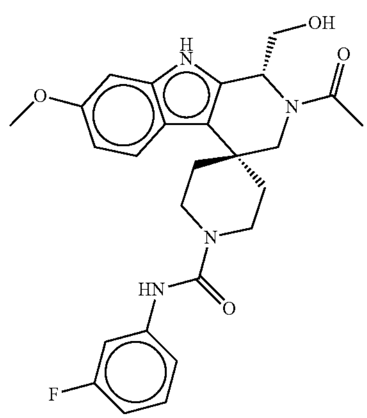 | (R)-2'-acetyl-N-(3-fluorophenyl)-1'-(hydroxymethyl)-7'-methoxy-1',2',3',9'-tetrahydrospiro[piperidine-4,4'-pyrido[3,4-b]indole]-1-carboxamide |
| 38 | 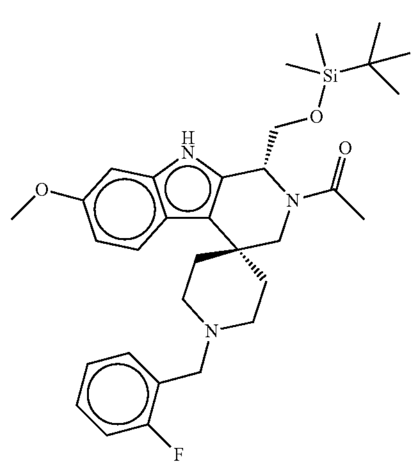 | (R)-1-(1'-(((tert-butyldimethylsilyl)oxy)methyl)-1-(2-fluorobenzyl)-7'-methoxyspiro[piperidine-4,4'-pyrido[3,4-b]indol]-2'(1'H,3'H,9'H)-yl)ethanone |

TABLE 1-continued

Selected Compounds of the Invention

| Example Number | Structure | Name |
|---|---|---|
| 39 | 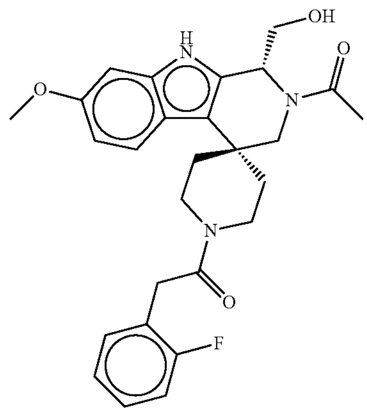 | (R)-1-(2'-acetyl-1'-(hydroxymethyl)-7'-methoxy-1',2',3',9'-tetrahydrospiro[piperidine-4,4'-pyrido[3,4-b]indol]-1-yl)-2-(2-fluorophenyl)ethanone |
| 40 | 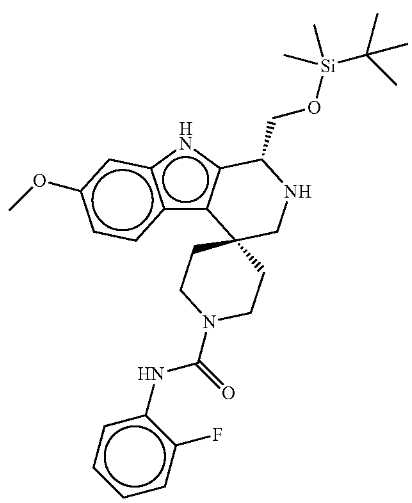 | (R)-1'-(((tert-butyldimethylsilyl)oxy)methyl)-N-(2-fluorophenyl)-7'-methoxy-1',2',3',9'-tetrahydrospiro[piperidine-4,4'-pyrido[3,4-b]indole]-1-carboxamide |
| 41 | 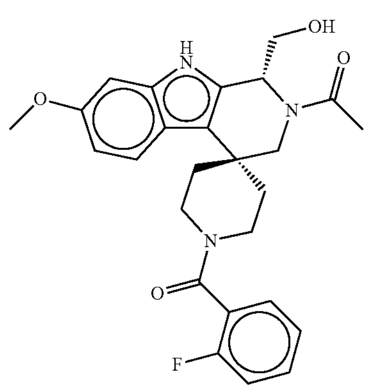 | (R)-1-(1-(2-fluorobenzoyl)-1'-(hydroxymethyl)-7'-methoxyspiro[piperidine-4,4'-pyrido[3,4-b]indol]-2'(1'H,3'H,9'H)-yl)ethanone |

TABLE 1-continued

Selected Compounds of the Invention

| Example Number | Structure | Name |
|---|---|---|
| 42 | 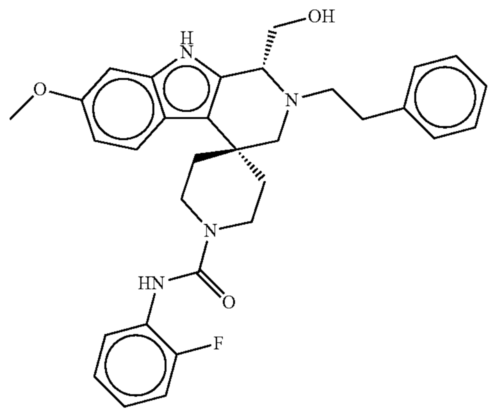 | (R)-N-(2-fluorophenyl)-1'-(hydroxymethyl)-7'-methoxy-2'-phenethyl-1',2',3',9'-tetrahydrospiro[piperidine-4,4'-pyrido[3,4-b]indole]-1-carboxamide |
| 43 | 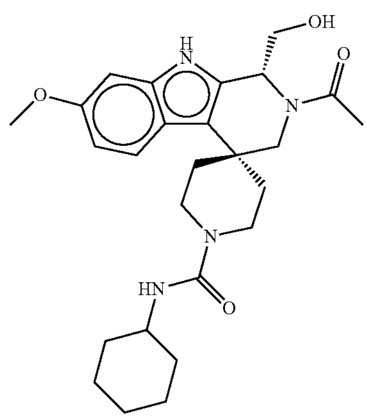 | (R)-2'-acetyl-N-cyclohexyl-1'-(hydroxymethyl)-7'-methoxy-1',2',3',9'-tetrahydrospiro[piperidine-4,4'-pyrido[3,4-b]indole]-1-carboxamide |
| 44 | 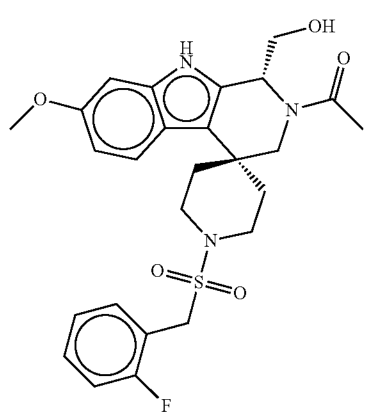 | (R)-1-(1-((2-fluorobenzyl)sulfonyl)-1'-(hydroxymethyl)-7'-methoxyspiro[piperidine-4,4'-pyrido[3,4-b]indol]-2'(1'H,3'H,9'H)-yl)ethanone |

TABLE 1-continued

Selected Compounds of the Invention

| Example Number | Structure | Name |
|---|---|---|
| 45 | 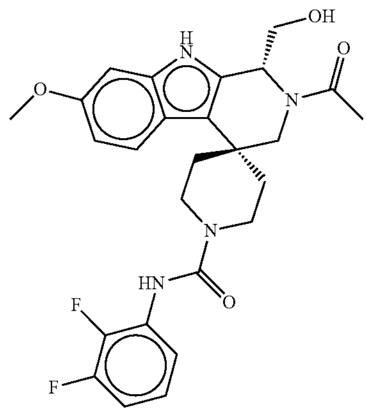 | (R)-2'-acetyl-N-(2,3-difluorophenyl)-1'-(hydroxymethyl)-7'-methoxy-1',2',3',9'-tetrahydrospiro[piperidine-4,4'-pyrido[3,4-b]indole]-1-carboxamide |
| 46 | 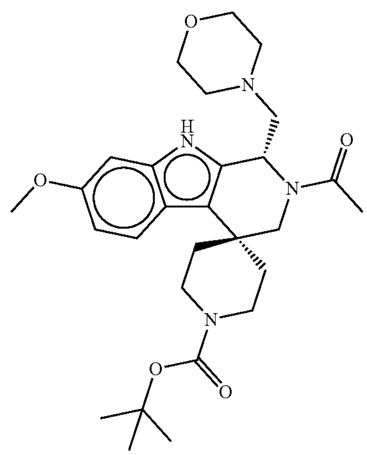 | (S)-tert-butyl 2'-acetyl-7'-methoxy-1'-(morpholinomethyl)-1',2',3',9'-tetrahydrospiro[piperidine-4,4'-pyrido[3,4-b]indole]-1-carboxylate |
| 47 | 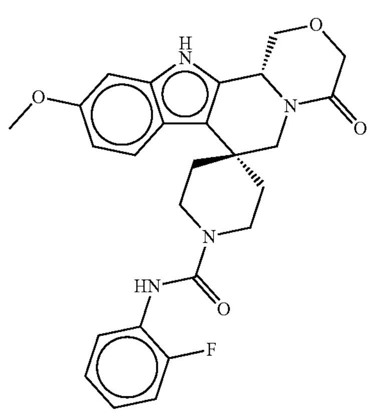 | (R)-N-(2-fluorophenyl)-10-methoxy-4-oxo-1,3,4,6,12,12b-hexahydrospiro[[1,4]oxazino[4',3':1,2]pyrido[3,4-b]indole-7,4'-piperidine]-1'-carboxamide |

TABLE 1-continued

Selected Compounds of the Invention

| Example Number | Structure | Name |
|---|---|---|
| 48 | 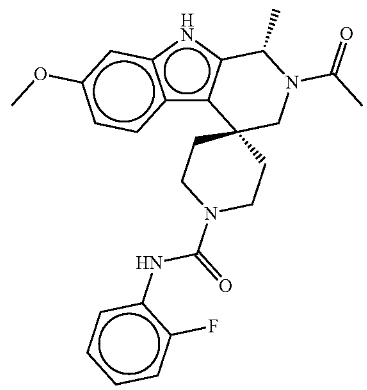 | (S)-2-acetyl-N-(2-fluorophenyl)-7'-methoxy-1'-methyl-1',2',3',9'-tetrahydrospiro[piperidine-4,4'-pyrido[3,4-b]indole]-1-carboxamide |
| 49 | 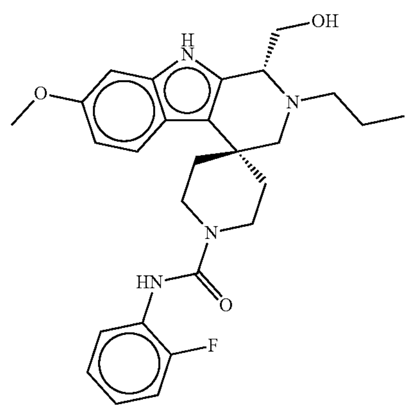 | (R)-N-(2-fluorophenyl)-1'-(hydroxymethyl)-7'-methoxy-2'-propyl-1',2',3',9'-tetrahydrospiro[piperidine-4,4'-pyrido[3,4-b]indole]-1-carboxamide |
| 50 | 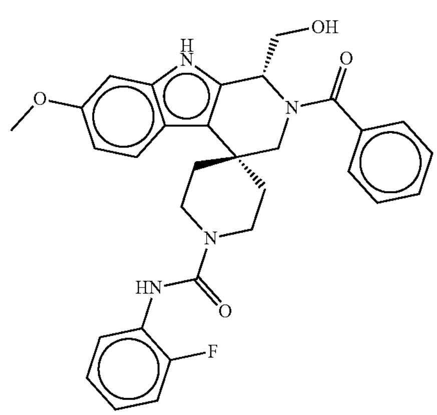 | (R)-2'-benzoyl-N-(2-fluorophenyl)-1'-(hydroxymethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 51 | 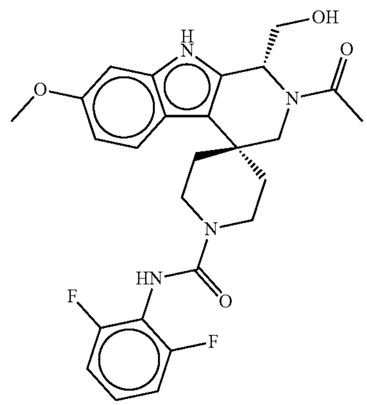 | (R)-2'-acetyl-N-(2,6-difluorophenyl)-1'-(hydroxymethyl)-7'-methoxy-1',2',3',9'-tetrahydrospiro[piperidine-4,4'-pyrido[3,4-b]indole]-1-carboxamide |
| 52 | 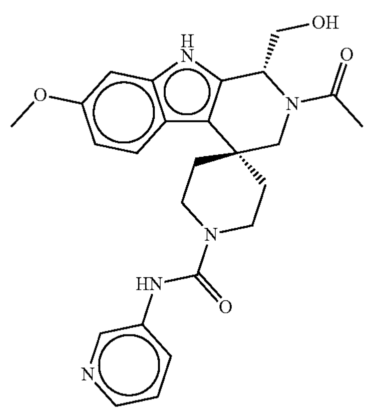 | (R)-2'-acetyl-1'-(hydroxymethyl)-7'-methoxy-N-(pyridin-3-yl)-1',2',3',9'-tetrahydrospiro[piperidine-4,4'-pyrido[3,4-b]indole]-1-carboxamide |
| 53 | 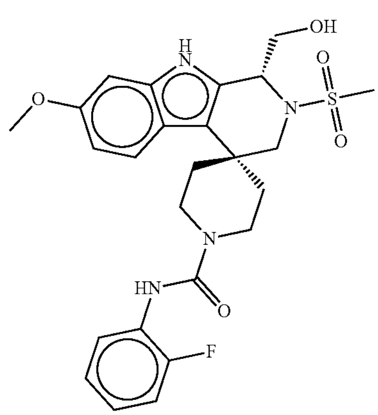 | (R)-N-(2-fluorophenyl)-1'-(hydroxymethyl)-7'-methoxy-2'-(methylsulfonyl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 54 | 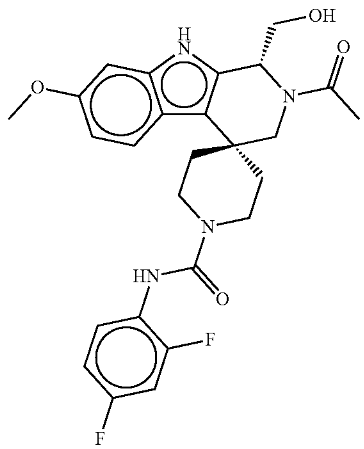 | (R)-2'-acetyl-N-(2,4-difluorophenyl)-1'-(hydroxymethyl)-7'-methoxy-1',2',3',9'-tetrahydrospiro[piperidine-4,4'-pyrido[3,4-b]indole]-1-carboxamide |
| 55 | 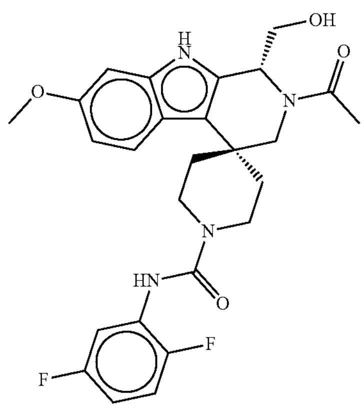 | (R)-2'-acetyl-N-(2,5-difluorophenyl)-1'-(hydroxymethyl)-7'-methoxy-1',2',3',9'-tetrahydrospiro[piperidine-4,4'-pyrido[3,4-b]indole]-1-carboxamide |
| 56 | 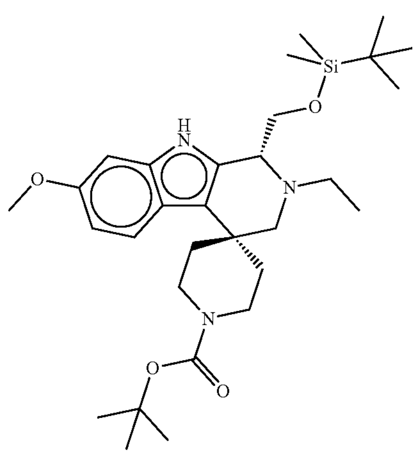 | (R)-tert-butyl 1'-(((tert-butyldimethylsilyl)oxy)methyl)-2'-ethyl-7'-methoxy-1',2',3',9'-tetrahydrospiro[piperidine-4,4'-pyrido[3,4-b]indole]-1-carboxylate |

TABLE 1-continued

Selected Compounds of the Invention

| Example Number | Structure | Name |
|---|---|---|
| 57 | 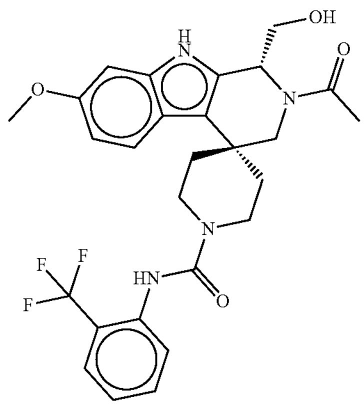 | (R)-2'-acetyl-1'-(hydroxymethyl)-7'-methoxy-N-(2-(trifluoromethyl)phenyl)-1',2',3',9'-tetrahydrospiro[piperidine-4,4'-pyrido[3,4-b]indole]-1-carboxamide |
| 58 | 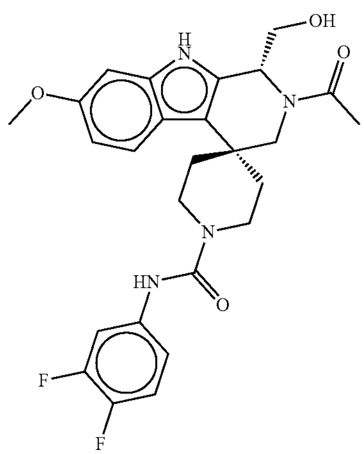 | (R)-2'-acetyl-N-(3,4-difluorophenyl)-1'-(hydroxymethyl)-7'-methoxy-1',2',3',9'-tetrahydrospiro[piperidine-4,4'-pyrido[3,4-b]indole]-1-carboxamide |
| 59 | 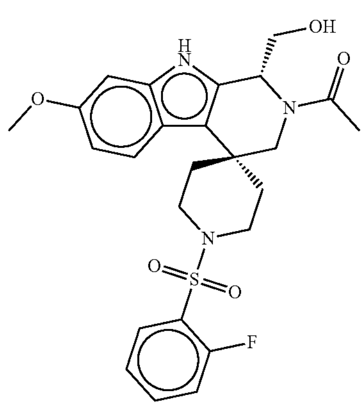 | (R)-1-(1-((2-fluorophenyl)sulfonyl)-1'-(hydroxymethyl)-7'-methoxyspiro[piperidine-4,4'-pyrido[3,4-b]indol]-2'(1'H,3'H,9'H)-yl)ethanone |

TABLE 1-continued

Selected Compounds of the Invention

| Example Number | Structure | Name |
|---|---|---|
| 60 | 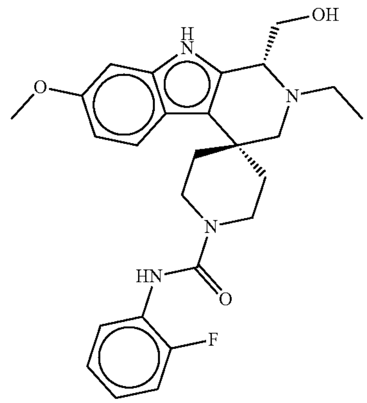 | (R)-2'-ethyl-N-(2-fluorophenyl)-1'-(hydroxymethyl)-7'-methoxy-1',2',3',9'-tetrahydrospiro[piperidine-4,4'-pyrido[3,4-b]indole]-1-carboxamide |
| 61 | 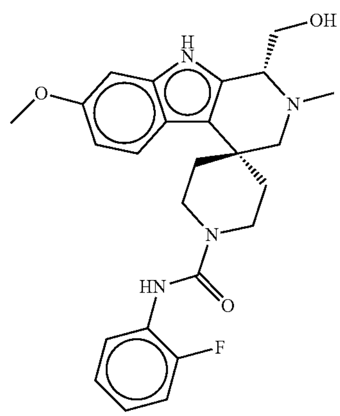 | (R)-N-(2-fluorophenyl)-1'-(hydroxymethyl)-7'-methoxy-2'-methyl-1',2',3',9'-tetrahydrospiro[piperidine-4,4'-pyrido[3,4-b]indole]-1-carboxamide |
| 62 | 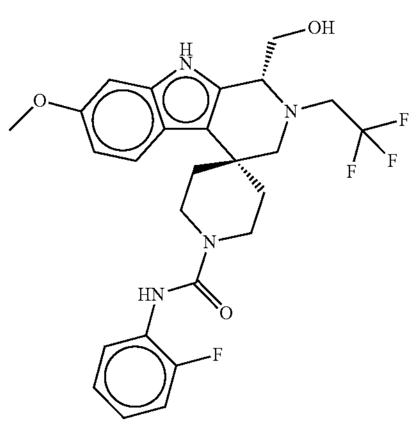 | (R)-N-(2-fluorophenyl)-1'-(hydroxymethyl)-7'-methoxy-2'-(2,2,2-trifluoroethyl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 63 | 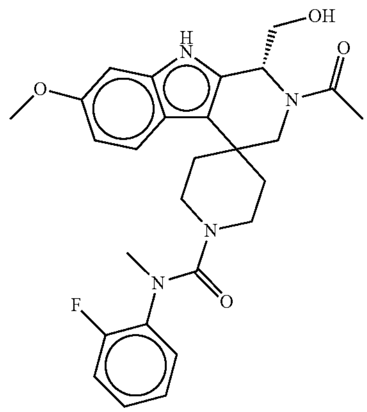 | (R)-2'-acetyl-N-(2-fluorophenyl)-1'-(hydroxymethyl)-7'-methoxy-N-methyl-1',2',3',9'-tetrahydrospiro[piperidine-4,4'-pyrido[3,4-b]indole]-1-carboxamide |
| 64 | 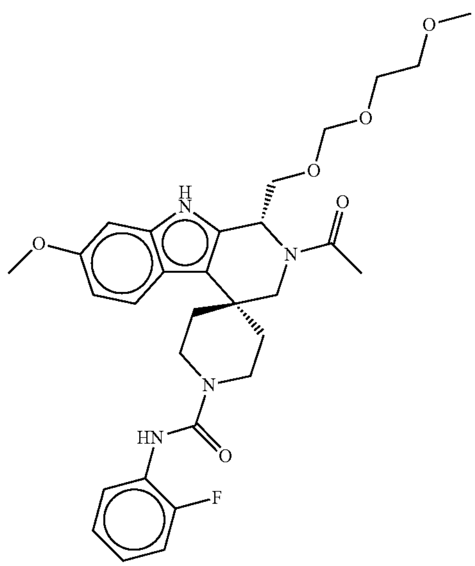 | (R)-2'-acetyl-N-(2-fluorophenyl)-7'-methoxy-1'-(((2-methoxyethoxy)methoxy)methyl)-1',2',3',9'-tetrahydrospiro[piperidine-4,4'-pyrido[3,4-b]indole]-1-carboxamide |
| 65 | 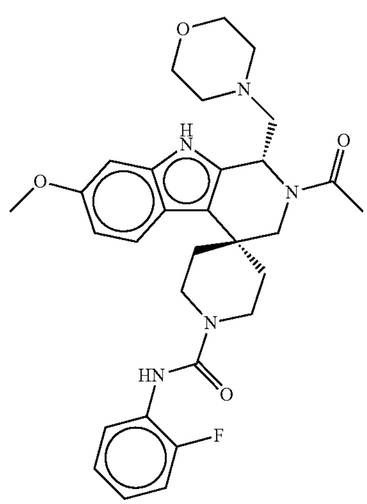 | (S)-2'-acetyl-N-(2-fluorophenyl)-7'-methoxy-1'-(morpholinomethyl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 66 | 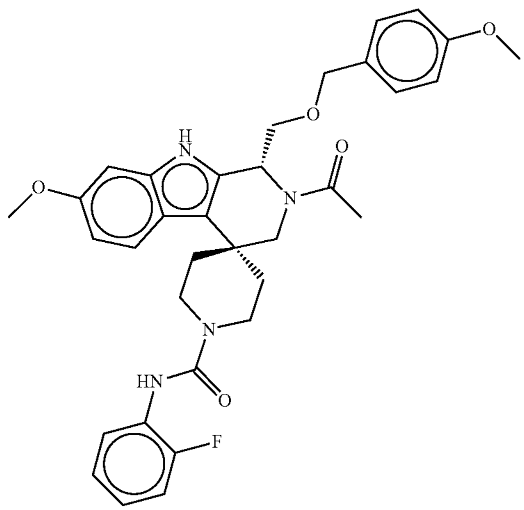 | (R)-2'-acetyl-N-(2-fluorophenyl)-7'-methoxy-1'-(((4-methoxybenzyl)oxy)methyl)-1',2',3',9'-tetrahydrospiro[piperidine-4,4'-pyrido[3,4-b]indole]-1-carboxamide |
| 67 | 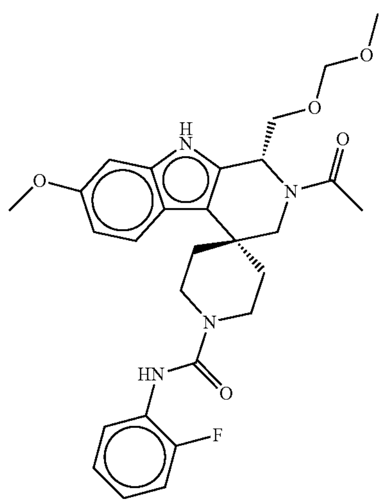 | (R)-2'-acetyl-N-(2-fluorophenyl)-7'-methoxy-1'-((methoxymethoxy)methyl)-1',2',3',9'-tetrahydrospiro[piperidine-4,4'-pyrido[3,4-b]indole]-1-carboxamide |
| 68 | 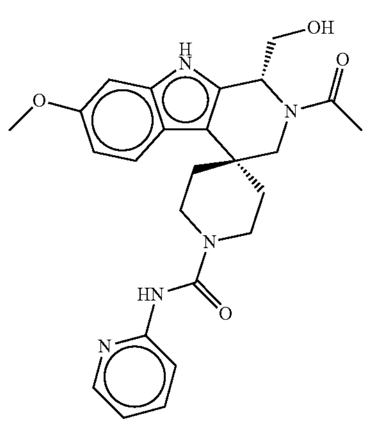 | (R)-2'-acetyl-1'-(hydroxymethyl)-7'-methoxy-N-(pyridin-2-yl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 69 | 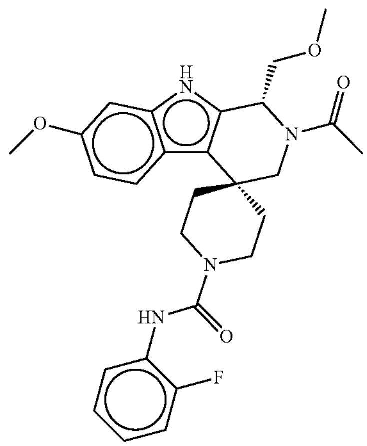 | (R)-2'-acetyl-N-(2-fluorophenyl)-7'-methoxy-1'-(methoxymethyl)-1',2',3',9'-tetrahydrospiro[piperidine-4,4'-pyrido[3,4-b]indole]-1-carboxamide |
| 70 | 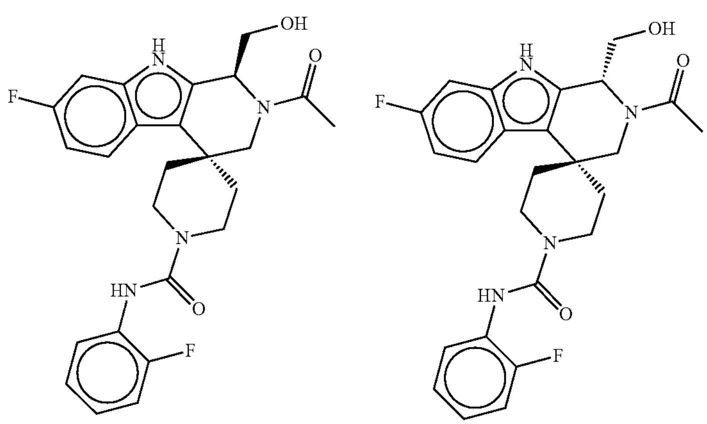 | (R)-2'-acetyl-7'-fluoro-N-(2-fluorophenyl)-1'-(hydroxymethyl)-1',2',3',9'-tetrahydrospiro[piperidine-4,4'-pyrido[3,4-b]indole]-1-carboxamide compound with (S)-Mixture of 2'-acetyl-7'-fluoro-N-(2-fluorophenyl)-1'-(hydroxymethyl)-1',2',3',9'-tetrahydrospiro[piperidine-4-4'-pyrido[3,4-b]indole]-1-carboxamide (1:1) and (R)-2'-acetyl-7'-fluoro-N-(2-fluorophenyl)-1'-(hydroxymethyl)-1',2',3',9'-tetrahydrospiro[piperidine-4,4'-pyrido[3,4-b]indole]-1-carboxamide compound with (S)-2'-acetyl-7'-fluoro-N-(2-fluorophenyl)-1'-(hydroxmethyl)-1',2',3',9'-tetrahydrospiro[piperidine-4,4'-pyrido[3,4-b]indole]-1-carboxamide (1:1) |

TABLE 1-continued

Selected Compounds of the Invention

| Example Number | Structure | Name |
|---|---|---|
| 71 | 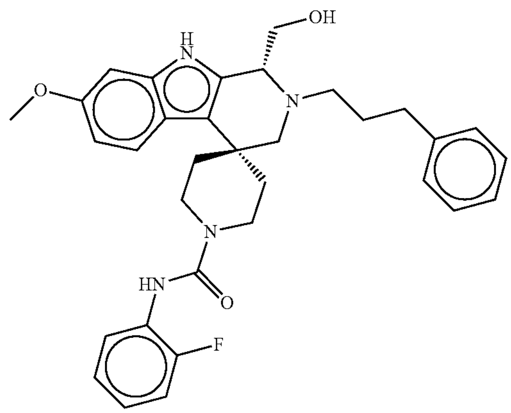 | (R)-N-(2-fluorophenyl)-1'-(hydroxymethyl)-7'-methoxy-2'-(3-phenylpropyl)-1',2',3',9'-tetrahydrospiro[piperidine-4,4'-pyrido[3,4-b]indole]-1-carboxamide |
| 72 | | Mixture of (1R,3'R) and (1R,3's)-2-acetyl-N-(2-fluorophenyl)-1-(hydroxymethyl)-7-methoxy-1,2,3,9-tetrahydrospiro[pyrido[3,4-b]indole-4,3'-pyrrolidine]-1'-carboxamide compound with (1R,3'S)-2-acetyl-N-(2-fluorophenyl)-1-(hydroxymethyl)-7-methoxy-1,2,3,9-tetrahydrospiro[pyrido[3,4-b]indole-4,3'-pyrrolidine]-1'-carboxamide (1:1) |
| 73 | 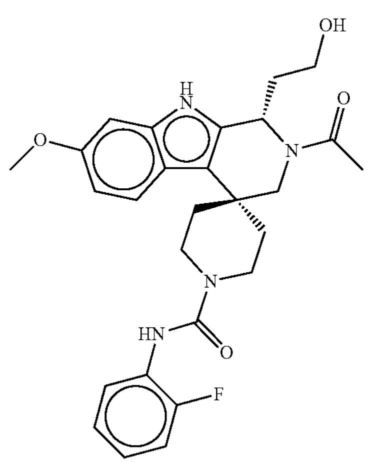 | (S)-2'-acetyl-N-(2-fluorophenyl)-1'-(2-hydroxyethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 74 | 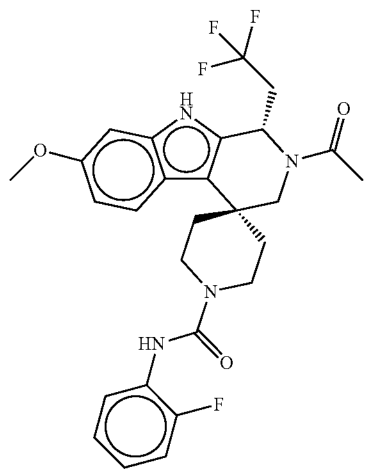 | (S)-2'-acetyl-N-(2-fluorophenyl)-7'-methoxy-1'-(2,2,2-trifluoroethyl)-1',2',3',9'-tetrahydrospiro[piperidine-4,4'-pyrido[3,4-b]indole]-1-carboxamide |
| 75 | 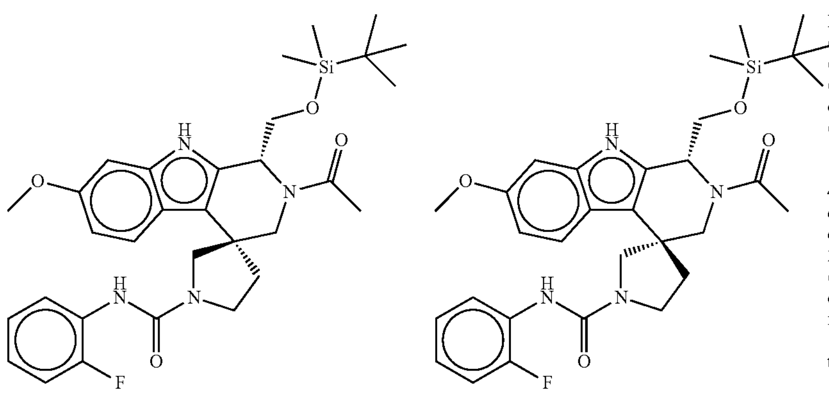 | Mixture of (1R,3'R) and (1R,3'S)-2-acetyl-1-(((tert-butyldimethylsilyl)oxy)methyl)-N-(2-fluorophenyl)-7-methoxy-1,2,3,9-tetrahydrospiro[pyrido[3,4-b]indole-4,3'-pyrrolidine]-1'-carboxamide compound with (1R,3'S)-2-acetyl-1-(((tert-butyldimethylsilyl)oxy)methyl)-N-(2-fluorophenyl)-7-methoxy-1,2,3,9-tetrahydrospiro[pyrido[3,4-b]indole-4-3'-pyrrolidine]-1'-carboxamide (1:1) |
| 76 | 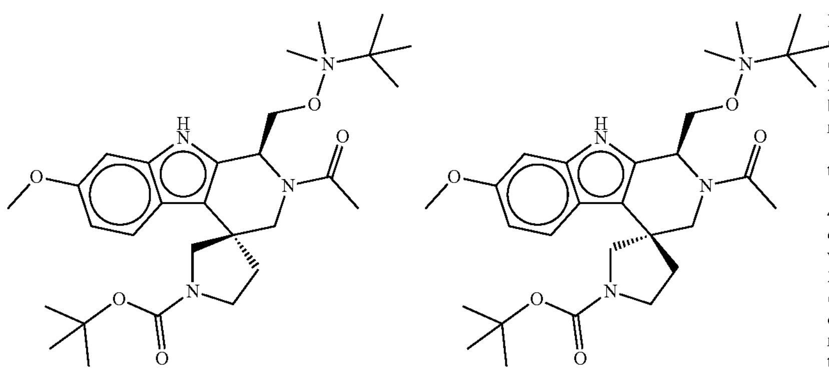 | Mixture of (1R,3'R) and (1R,3'S)-tert-butyl 2-acetyl-1-(((tert-butyldimethylsilyl)oxy)methyl)-7-methoxy-1,2,3,9-tetrahydrospiro[pyrido[3,4-b]indole-4,3'-pyrrolidine]-1'-carboxylate compound with (1R,3'S)-tert-butyl 2-acetyl-1-(((tert-butyldimethylsilyl)oxy)methyl)-7-methoxy-1,2,3,9-tetrahydrospiro[pyrido[3,4-b]indole-4,3'-pyrrolidine]-1'-carboxylate (1:1) |

TABLE 1-continued

Selected Compounds of the Invention

| Example Number | Structure | Name |
| --- | --- | --- |
| 77 | 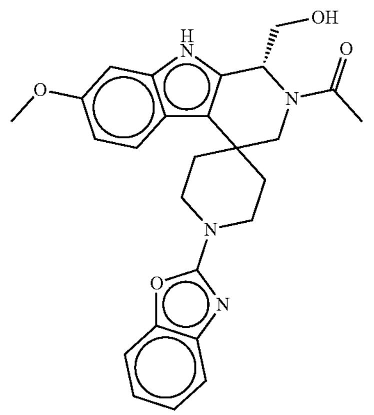 | (R)-1-(1-(benzo[d]oxazol-2-yl)-1'-(hydroxymethyl)-7'-methoxyspiro[piperidine-4,4'-pyrido[3,4-b]indol]-2'(1'H,3'H,9'H)-yl)ethanone |
| 78 | 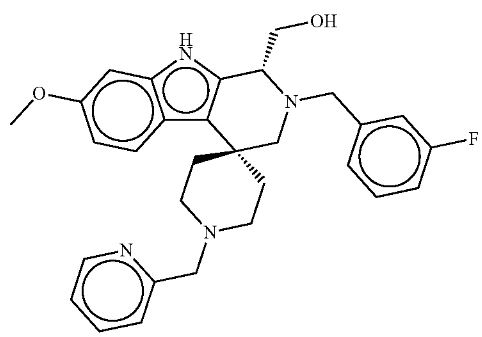 | (R)-(2'-(3-fluorobenzyl)-7'-methoxy-1-(pyridin-2-ylmethyl)-1',2',3',9'-tetrahydrospiro[piperidine-4,4'-pyrido[3,4-b]indol]-1'-yl)methanol |
| 79 | 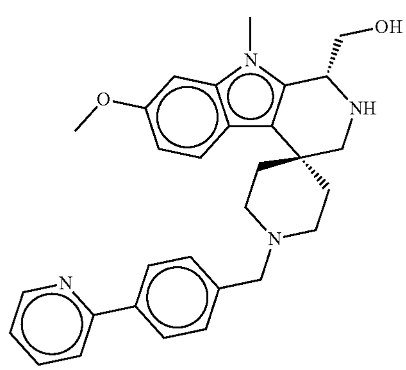 | (R)-(7'-methoxy-9'-methyl-1-(4-(pyridin-2-yl)benzyl)-1',2',3',9'-tetrahydrospiro[piperidine-4,4'-pyrido[3,4-b]indol]-1'-yl)methanol |
| 80 | 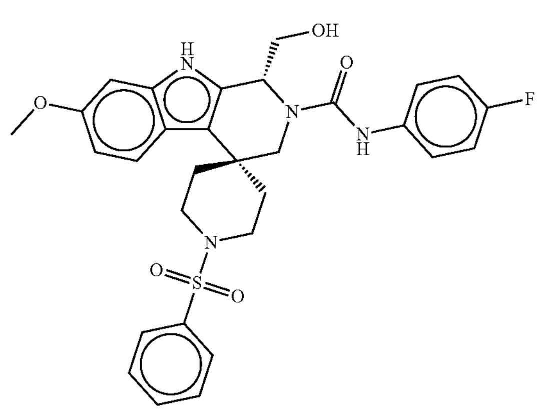 | (R)-N-(4-fluorophenyl)-1'-(hydroxymethyl)-7'-methoxy-1-(phenylsulfonyl)-3',9'-dihydrospiro[piperidine-4,4'-pyrido[3,4-b]indole]-2'(1'H)-carboxamide |

TABLE 1-continued

Selected Compounds of the Invention

| Example Number | Structure | Name |
|---|---|---|
| 81 | 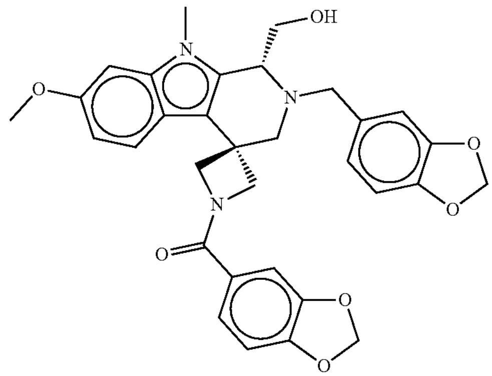 | (R)-benzo[d][1,3]dioxol-5-yl(2'-(benzo[d][1,3]dioxol-5-ylmethyl)-1'-(hydroxymethyl)-7'-methoxy-9'-methyl-1',2',3',9'-tetrahydrospiro[azetidine-3,4'-pyrido[3,4-b]indol]-1-yl)methanone |
| 82 | 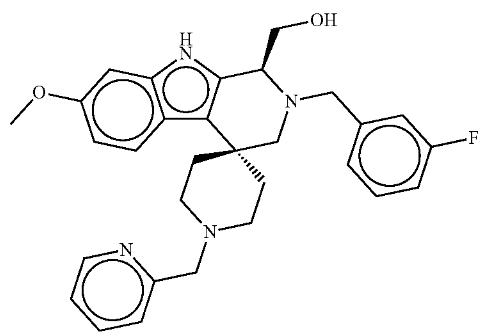 | (S)-(2'-(3-fluorobenzyl)-7'-methoxy-1-(pyridin-2-ylmethyl)-1',2',3',9'-tetrahydrospiro[piperidine-4,4'-pyrido[3,4-b]indol]-1'-yl)methanol |
| 83 | 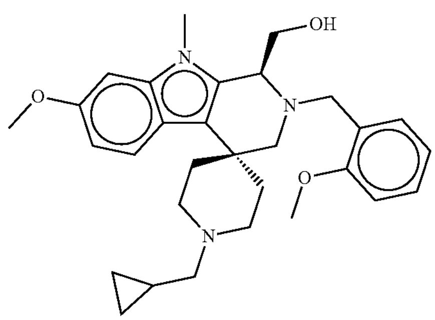 | (S)-(1-(cyclopropylmethyl)-7'-methoxy-2'-(2-methoxybenzyl)-9'-methyl-1',2',3',9'-tetrahydrospiro[piperidine-4,4'-pyrido[3,4-b]indol]-1'-yl)methanol |
| 84 | 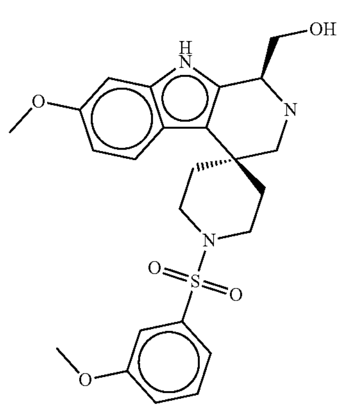 | (S)-(7'-methoxy-1-((3-methoxyphenyl)sulfonyl)-1',2',3',9'-tetrahydrospiro[piperidine-4,4'-pyrido[3,4-b]indol]-1'-yl)methanol |

| Example Number | Structure | Name |
|---|---|---|
| 85 | 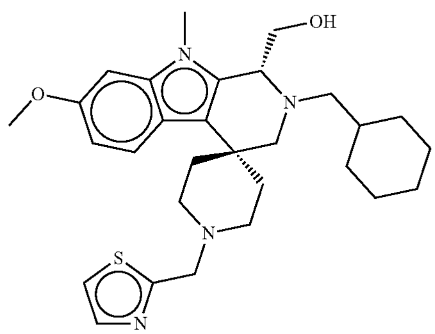 | (R)-(2'-(cyclohexylmethyl)-7'-methoxy-9'-methyl-1-(thiazol-2-ylmethyl)-1',2',3',9'-tetrahydrospiro[piperidine-4,4'-pyrido[3,4-b]indol]-1'-yl)methanol |
| 86 | 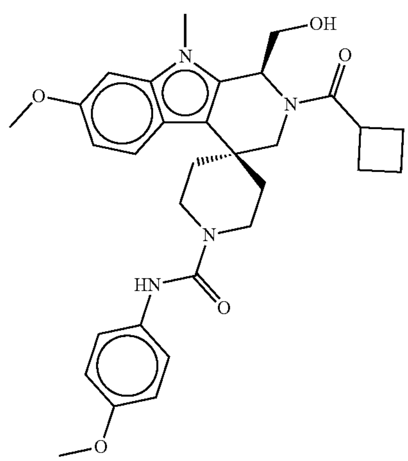 | (S)-2'-(cyclobutanecarbonyl)-1'-(hydroxymethyl)-7'-methoxy-N-(4-methoxyphenyl)-9'-methyl-1',2',3',9'-tetrahydrospiro[piperidine-4,4'-pyrido[3,4-b]indole]-1-carboxamide |
| 87 | 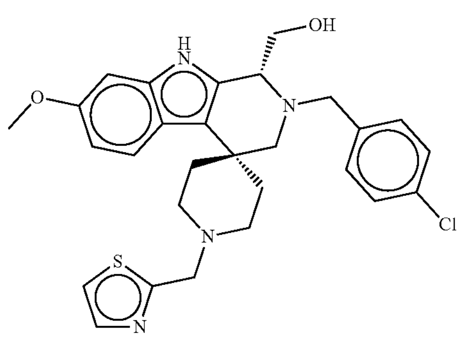 | (R)-(2'-(4-chlorobenzyl)-7'-methoxy-1-(thiazol-2-ylmethyl)-1',2',3',9'-tetrahydrospiro[piperidine-4,4'-pyrido[3,4-b]indol]-1'-yl)methanol |
| 88 | 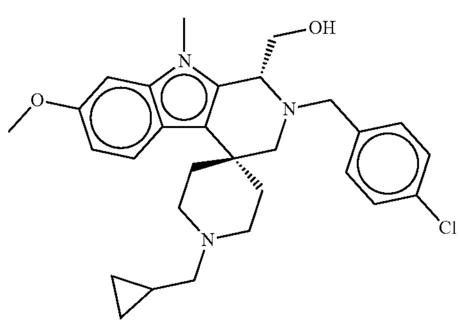 | (R)-(2'-(4-chlorobenzyl)-1-(cyclopropylmethyl)-7'-methoxy-9'-methyl-1',2',3',9'-tetrahydrospiro[piperidine-4,4'-pyrido[3,4-b]indol]-1'-yl)methanol |

TABLE 1-continued

Selected Compounds of the Invention

| Example Number | Structure | Name |
|---|---|---|
| 89 | 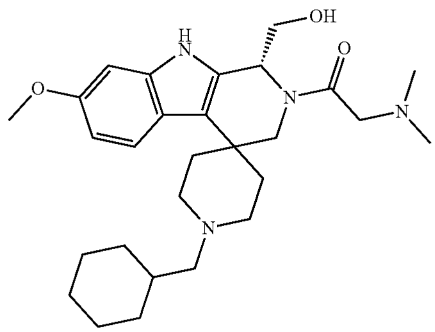 | (R)-1-(1-(cyclohexylmethyl)-1'-(hydroxymethyl)-7'-methoxyspiro[piperidine-4,4'-pyrido[3,4-b]indol]-2'(1'H,3'H,9'H)-yl)-2-(dimethylamino)ethanone |
| 90 | 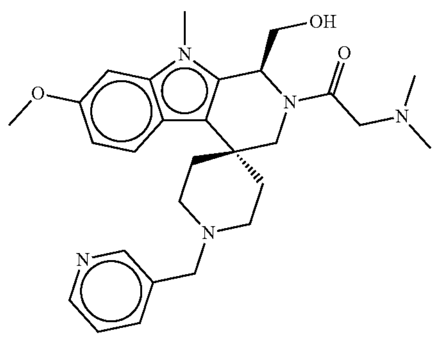 | (S)-2-(dimethylamino)-1-(1'-(hydroxymethyl)-7'-methoxy-9'-methyl-1-(pyridin-3-ylmethyl)spiro[piperidine-4,4'-pyrido[3,4-b]indol]-2'(1'H,3'H,9'H)-yl)ethanone |
| 91 | 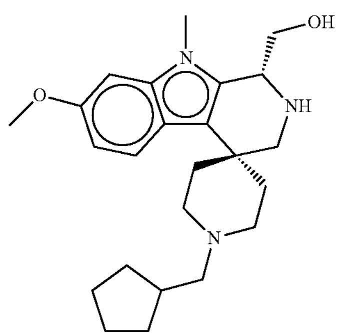 | (R)-(1-(cyclopentylmethyl)-7'-methoxy-9'-methyl-1',2',3',9'-tetrahydrospiro[piperidine-4,4'-pyrido[3,4-b]indol]-1'-yl)methanol |
| 92 | 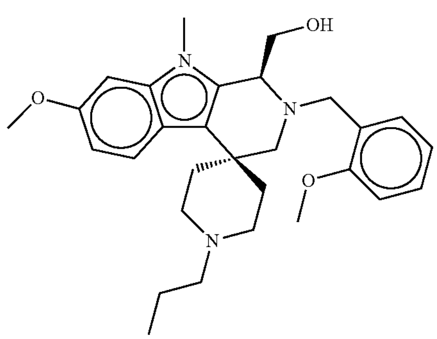 | (S)-(7'-methoxy-2'-(2-methoxybenzyl)-9'-methyl-1-propyl-1',2',3',9'-tetrahydrospiro[piperidine-4,4'-pyrido[3,4-b]indol]-1'-yl)methanol |

TABLE 1-continued

Selected Compounds of the Invention

| Example Number | Structure | Name |
|---|---|---|
| 93 | 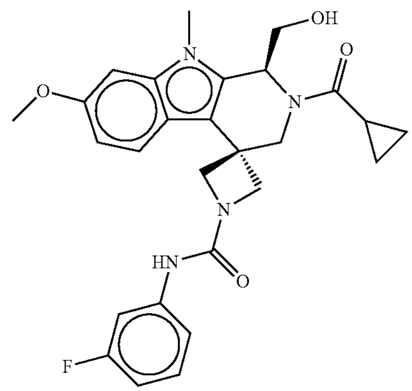 | (S)-2'-(cyclopropanecarbonyl)-N-(3-fluorophenyl)-1'-(hydroxymethyl)-7'-methoxy-9'-methyl-1',2',3',9'-tetrahydrospiro[azetidine-3,4'-pyrido[3,4-b]indole]-1-carboxamide |
| 94 | 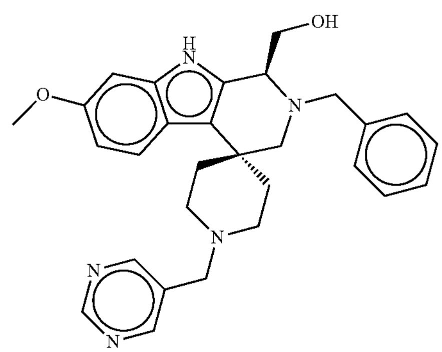 | (S)-(2'-benzyl-7'-methoxy-1-(pyrimidin-5-ylmethyl)-1',2',3',9'-tetrahydrospiro[piperidine-4,4'-pyrido[3,4-b]indol]-1'-yl)methanol |
| 95 | 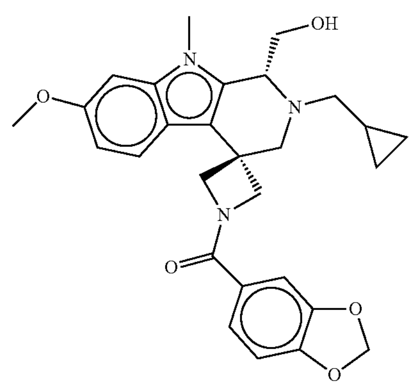 | (R)-benzo[d][1,3]dioxol-5-yl(2'-(cyclopropylmethyl)-1'-(hydroxymethyl)-7'-methoxy-9'-methyl-1',2',3',9'-tetrahydrospiro[azetidine-3,4'-pyrido[3,4-b]indol]-1-yl)methanone |
| 96 | 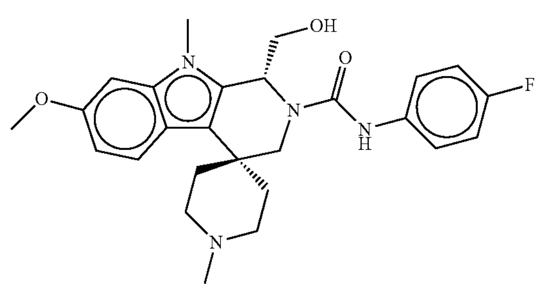 | (R)-N-(4-fluorophenyl)-1'-(hydroxymethyl)-7'-methoxy-1,9'-dimethyl-3',9'-dihydrospiro[piperidine-4,4'-pyrido[3,4-b]indole]-2'(1'H)-carboxamide |

TABLE 1-continued

Selected Compounds of the Invention

| Example Number | Structure | Name |
|---|---|---|
| 97 | 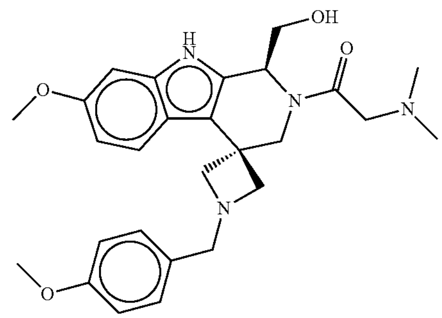 | (S)-2-(dimethylamino)-1-(1'-(hydroxymethyl)-7'-methoxy-1-(4-methoxybenzyl)spiro[azetidine-3,4'-pyrido[3,4-b]indol]-2'(1'H,3'H,9'H)-yl)ethanone |
| 98 | 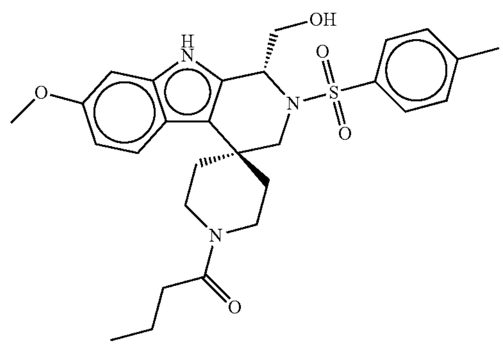 | (R)-1-(1'-(hydroxymethyl)-7'-methoxy-2'-tosyl-1',2',3',9'-tetrahydrospiro[piperidine-4,4'-pyrido[3,4-b]indol]-1-yl)butan-1-one |
| 99 | 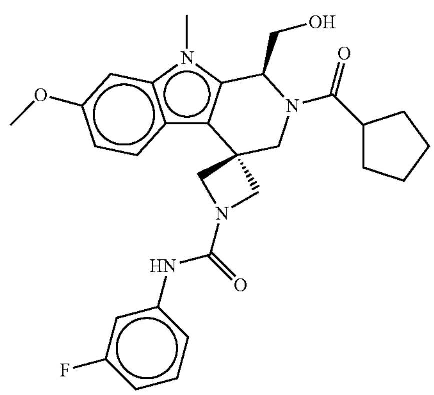 | (S)-2'-(cyclopentanecarbonyl)-N-(3-fluorophenyl)-1'-(hydroxymethyl)-7'-methoxy-9'-methyl-1',2',3',9'-tetrahydrospiro[azetidine-3,4'-pyrido[3,4-b]indole]-1-carboxamide |
| 100 | 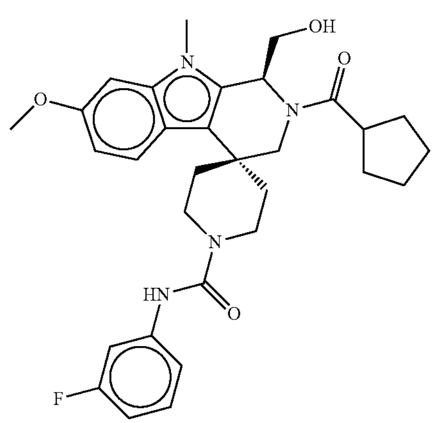 | (S)-2'-(cyclopentanecarbonyl)-N-(3-fluorophenyl)-1'-(hydroxymethyl)-7'-methoxy-9'-methyl-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 101 | 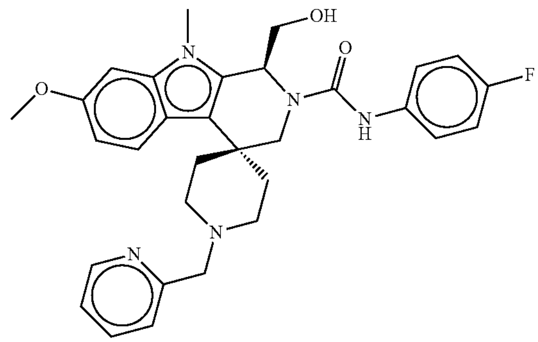 | (S)-N-(4-fluorophenyl)-1'-(hydroxymethyl)-7'-methoxy-9'-methyl-1-(pyridin-2-ylmethyl)-3',9'-dihydrospiro[piperidine-4,4'-pyrido[3,4-b]indole]-2'(1'H)-carboxamide |
| 102 | 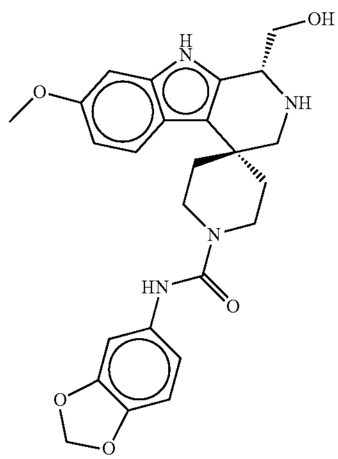 | (R)-N-(benzo[d][1,3]dioxol-5-yl)-1'-(hydroxymethyl)-7'-methoxy-1',2',3',9'-tetrahydrospiro[piperidine-4,4'-pyrido[3,4-b]indole]-1-carboxamide |
| 103 | 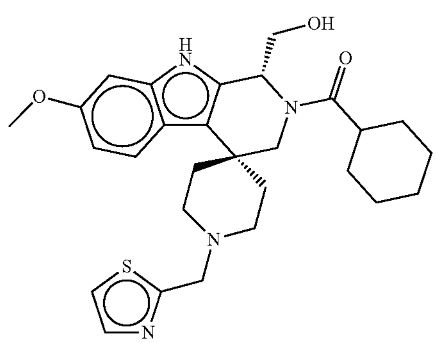 | (R)-cyclohexyl(1'-(hydroxymethyl)-7'-methoxy-1-(thiazol-2-ylmethyl)spiro[piperidine-4,4'-pyrido[3,4-b]indol]-2'(1'H,3'H,9'H)-yl)methanone |
| 104 | 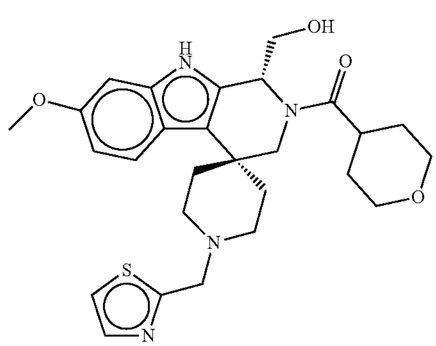 | (R)-(1'-(hydroxymethyl)-7'-methoxy-1-(thiazol-2-ylmethyl)spiro[piperidine-4,4'-pyrido[3,4-b]indol]-2'(1'H,3'H,9'H)-yl)(tetrahydro-2H-pyran-4-yl)methanone |

TABLE 1-continued

Selected Compounds of the Invention

| Example Number | Structure | Name |
| --- | --- | --- |
| 105 | 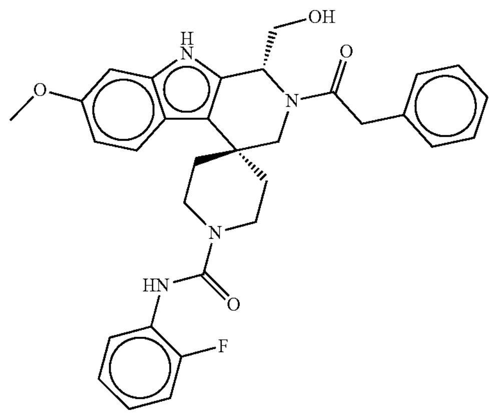 | (R)-N-(2-fluorophenyl)-1'-(hydroxymethyl)-7'-methoxy-2'-(2-phenylacetyl)-1',2',3',9'-tetrahydrospiro[piperidine-4,4'-pyrido[3,4-b]indole]-1-carboxamide |
| 106 | 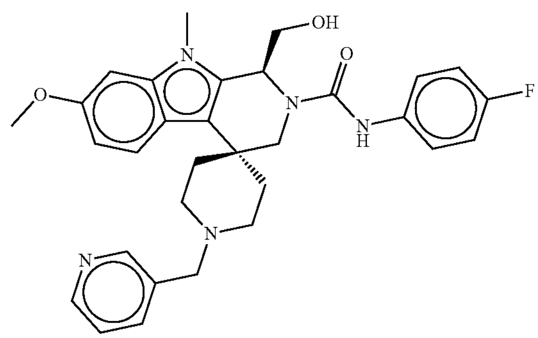 | (S)-N-(4-fluorophenyl)-1'-(hydroxymethyl)-7'-methoxy-9'-methyl-1-(pyridin-3-ylmethyl)-3',9'-dihydrospiro[piperidine-4,4'-pyrido[3,4-b]indole]-2'(1'H)-carboxamide |
| 107 | 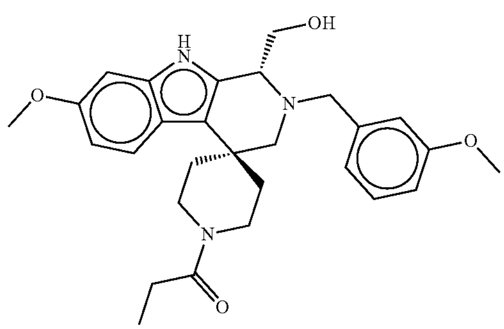 | (R)-1-(1'-(hydroxymethyl)-7'-methoxy-2'-(3-methoxybenzyl)-1',2',3',9'-tetrahydrospiro[piperidine-4,4'-pyrido[3,4-b]indol]-1-yl)propan-1-one |
| 108 | 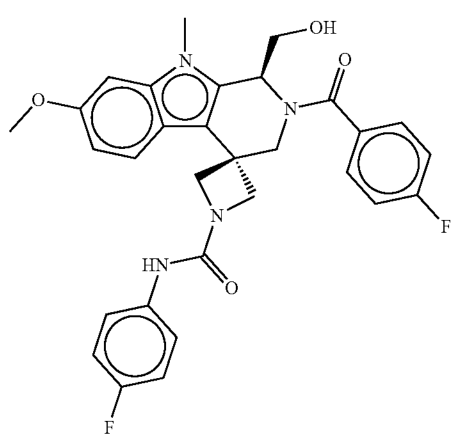 | (S)-2'-(4-fluorobenzoyl)-N-(4-fluorophenyl)-1'-(hydroxymethyl)-7'-methoxy-9'-methyl-1',2',3',9'-tetrahydrospiro[azetidine-3,4'-pyrido[3,4-b]indole]-1-carboxamide |

TABLE 1-continued

Selected Compounds of the Invention

| Example Number | Structure | Name |
|---|---|---|
| 109 | 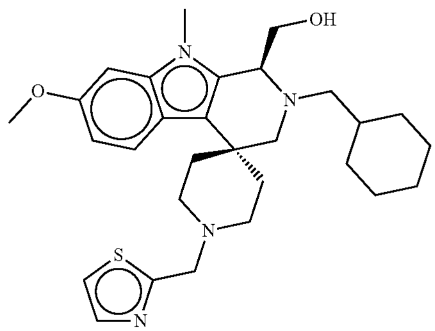 | (S)-(2'-(cyclohexylmethyl)-7'-methoxy-9'-methyl-1-(thiazol-2-ylm ethyl)-1',2',3',9'-tetrahydrospiro[piperidine-4,4'-pyrido[3,4-b]indol]-1'-yl)methanol |
| 110 | 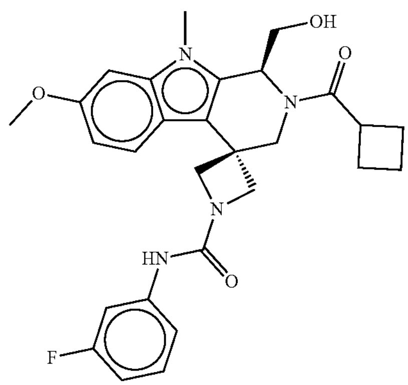 | (S)-2'-(cyclobutanecarbonyl)-N-(3-fluorophenyl)-1'-(hydroxymethyl)-7'-methoxy-9'-methyl-1',2',3',9'-tetrahydrospiro[azetidine-3,4'-pyrido[3,4-b]indole]-1-carboxamide |
| 111 | 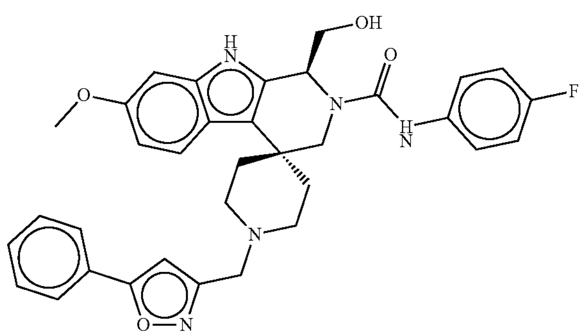 | (R)-N-(4-fluorophenyl)-1'-(hydroxymethyl)-7'-methoxy-1-((5-phenylisoxazol-3-yl)methyl)-3',9'-dihydrospiro[piperidine-4,4'-pyrido[3,4-b]indole]-2'(1'H)-carboxamide |
| 112 | 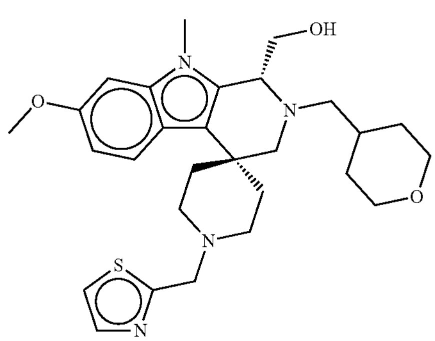 | (R)-(7'-methoxy-9'-methyl0-2'-((tetrahydro-2H-pyran-4-yl)methyl)-1-(thiazol-2-ylmethyl)-1',2',3',9'-tetrahydrospiro[piperidine-4,4'-pyrido[3,4-b]indol]-1'-yl)methanol |

TABLE 1-continued

Selected Compounds of the Invention

| Example Number | Structure | Name |
| --- | --- | --- |
| 113 | 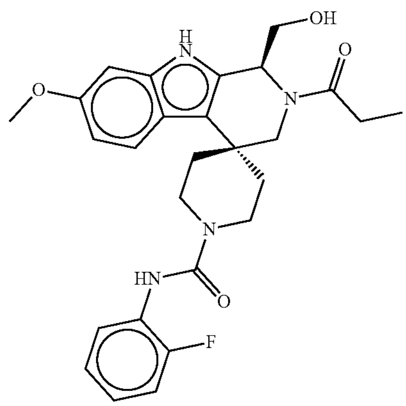 | (S)-N-(2-fluorophenyl)-1'-(hydroxymethyl)-7'-methoxy-2'-propionyl-1',2',3',9'-tetrahydrospiro[piperidine-4,4'-pyrido[3,4-b]indole]-1-carboxamide |
| 114 | 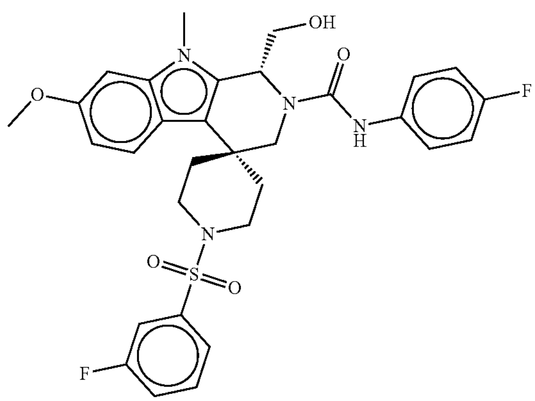 | (R)-N-(4-fluorophenyl)-1-((3-fluorophenyl)sulfonyl)-1'-(hydroxymethyl)-7'-methoxy-9'-methyl-3',9'-dihydrospiro[piperidine-4,4'-pyrido[3,4-b]indole]-2'(1'H)-carboxamide |
| 115 | 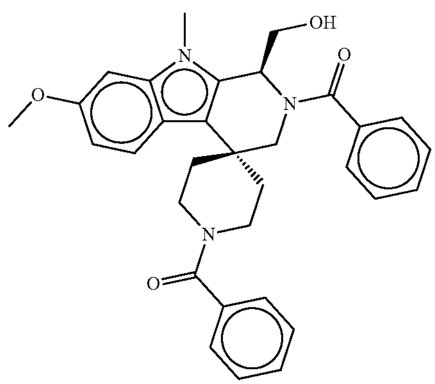 | (S)-(1'-(hydroxymethyl)-7'-methoxy-9'-methylspiro[piperidine-4,4'-pyrido[3,4-b]indol]-1,2'(1'H,3'H,9'H)-diyl)bis(phenylmethanone) |
| 116 | 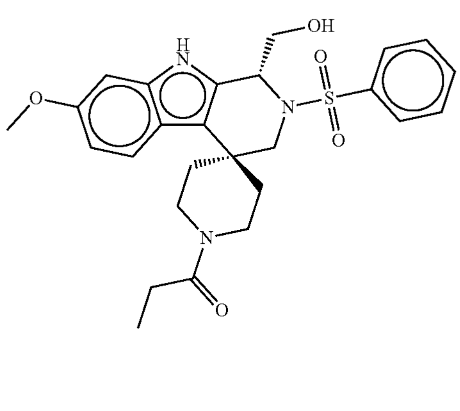 | (R)-1-(1'-(hydroxymethyl)-7'-methoxy-2'-(phenylsulfonyl)-1',2',3',9'-tetrahydrospiro[piperidine-4,4'-pyrido[3,4-b]indol]-1-yl)propan-1-one |

TABLE 1-continued

Selected Compounds of the Invention

| Example Number | Structure | Name |
|---|---|---|
| 117 | 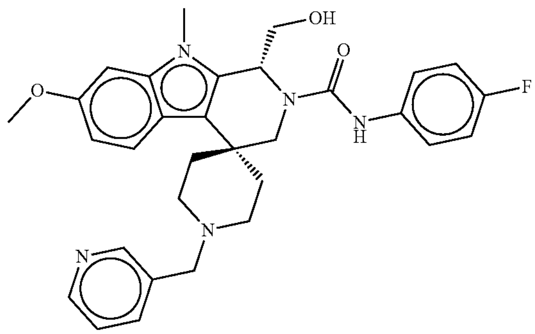 | (R)-N-(4-fluorophenyl)-1'-(hydroxymethyl)-7'-methoxy-9'-methyl-1-(pyridin-3-ylmethyl)-3',9'-dihydrospiro[piperidine-4,4'-pyrido[3,4-b]indole]-2'(1'H)-carboxamide |
| 118 | 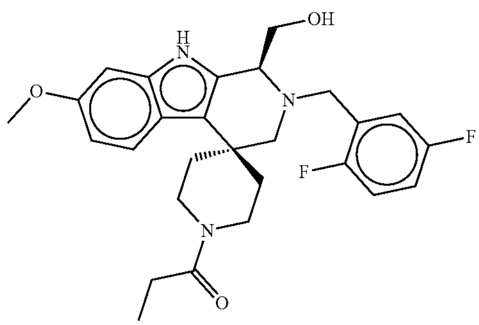 | (S)-1-(2'-(2,5-difluorobenzyl)-1'-(hydroxymethyl)-7'-methoxy-1',2',3',9'-tetrahydrospiro[piperidine-4,4'-pyrido[3,4-b]indol]-1-yl)propan-1-one |
| 119 | 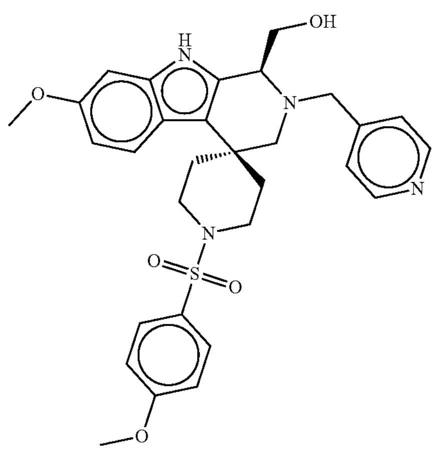 | (S)-(7'-methoxy-1-((4-methoxyphenyl)sulfonyl)-2'-(pyridin-4-ylmethyl)-1',2',3',9'-tetrahydrospiro[piperidine-4,4'-pyrido[3,4-b]indol]-1'-yl)methanol |
| 120 | 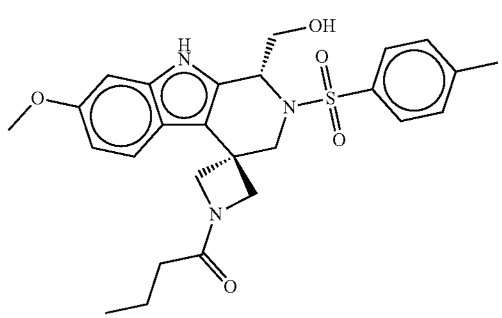 | (R)-1-(1'-(hydroxymethyl)-7'-methoxy-2'-tosyl-1',2',3',9'-tetrahydrospiro[azetidine-3,4'-pyrido[3,4-b]indol]-1-yl)butan-1-one |

TABLE 1-continued

Selected Compounds of the Invention

| Example Number | Structure | Name |
|---|---|---|
| 121 | 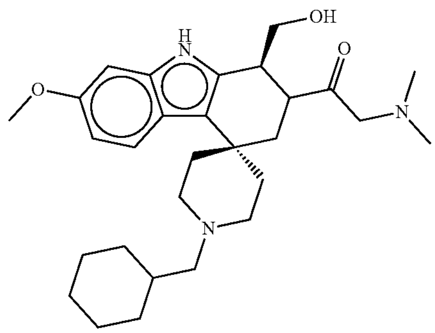 | (S)-1-(1-(cyclohexylmethyl)-1'-(hydroxymethyl)-7'-methoxyspiro[piperidine-4,4'-pyrido[3,4-b]indol]-2'(1'H,3'H,9'H)-yl)-2-(dimethylamino)ethanone |
| 122 | 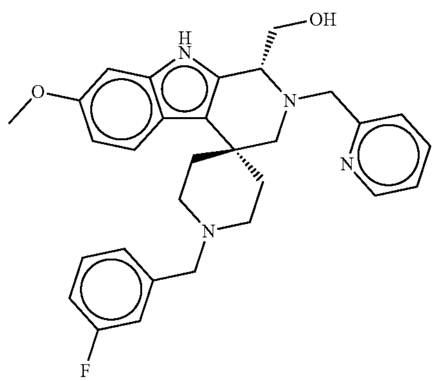 | (R)-(1-(3-fluorobenzyl)-7'-methoxy-2'-(pyridin-2-ylmethyl)-1',2',3',9'-tetrahydrospiro[piperidine-4,4'-pyrido[3,4-b+indol]-1'-yl)methanol |
| 123 | 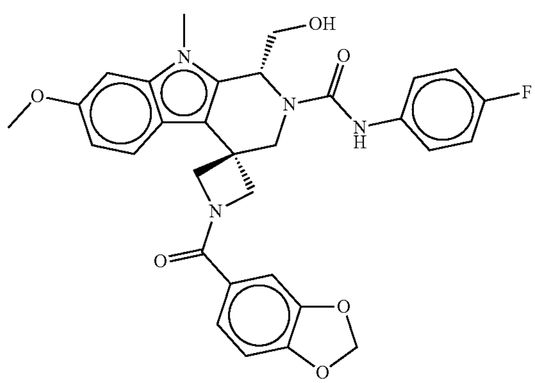 | (R)-1-(benzo[d][1,3]dioxole-5-carbonyl)-N-(4-fluorophenyl)-1'-(hydroxymethyl)-7'-methoxy-9'-methyl-3',9'-dihydrospiro[azetidine-3,4'-pyrido[3,4-b]indole]-2'(1'H)-carboxamide |
| 124 | 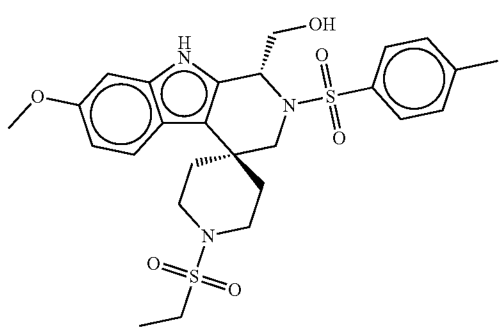 | (R)-(1-(ethylsulfony1)-7'-methoxy-2'-tosyl-1',2',3',9'-tetrahydrospiro[piperidine-4,4'-pyrido[3,4-b]indol]-1'-yl)methanol |

TABLE 1-continued

Selected Compounds of the Invention

| Example Number | Structure | Name |
|---|---|---|
| 125 | 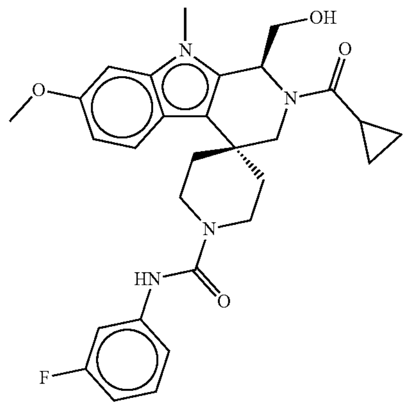 | (S)-2'-(cyclopropanecarbonyl)-N-(3-fluorophenyl)-1'-(hydroxymethyl)-7'-methoxy-9'-methyl-1',2',3',9'-tetrahydrospiro[piperidine-4,4'-pyrido[3,4-b]indole]-1-carboxamide |
| 126 | 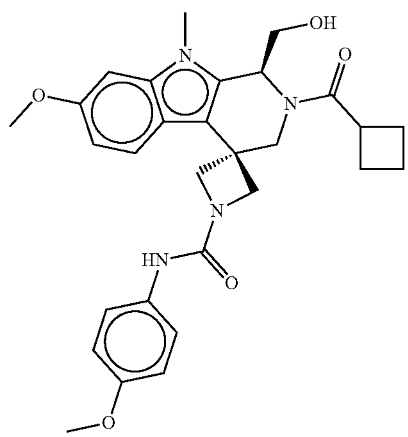 | (S)-2'-(cyclobutanecarbonyl)-1'-(hydroxymethyl)-7'-methoxy-N-(4-methoxyphenyl)-9'-methyl-1',2',3',9'-tetrahydrospiro[azetidine-3,4'-pyrido[3,4-b]indole]-1-carboxamide |
| 127 | 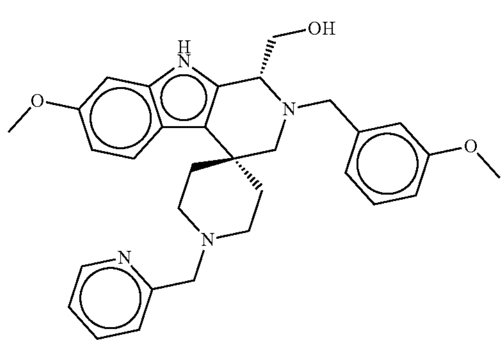 | (R)-(7'-methoxy-2'-(3-methoxybenzyl)-1'-(pyridin-2-ylmethyl)-1',2',3',9'-tetrahydrospiro[pipendine-4,4'-pyrido[3,4-b]indol]-1'-yl)methanol |

TABLE 1-continued

Selected Compounds of the Invention

| Example Number | Structure | Name |
|---|---|---|
| 128 | 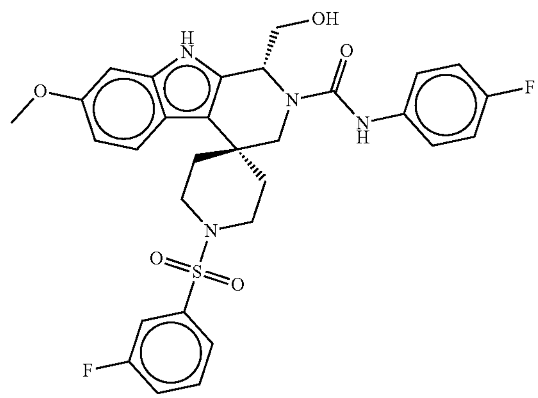 | (R)-N-(4-fluorophenyl)-1-((3-fluorophenyl)sulfonyl)-1'-(hydroxymethyl)-7'-methoxy-3',9'-dihydrospiro[piperidine-4,4'-pyrido[3,4-b]indole]-2'(1'H)-carboxamide |
| 129 | 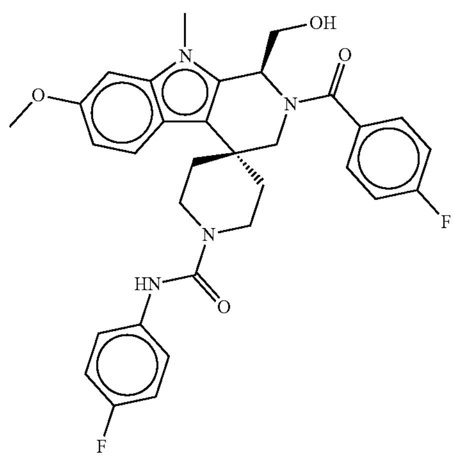 | (S)-2'-(4-fluorobenzoyl)-N-(4-fluorophenyl)-1'-(hydroxymethyl)-7'-methoxy-9'-methyl-1',2',3',9'-tetrahydrospiro[piperidine-4,4'-pyrido[3,4-b]indole]-1-carboxamide |
| 130 | 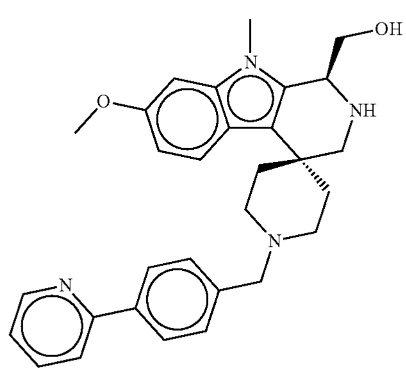 | (S)-(7'-methoxy-9'-methyl-1-(4-(pyridin-2-yl)benzyl)-1',2',3',9'-tetrahydrospiro[piperidine-4,4'-pyrido[3,4-b]indol]-1'-yl)methanol |

TABLE 1-continued

Selected Compounds of the Invention

| Example Number | Structure | Name |
|---|---|---|
| 131 | 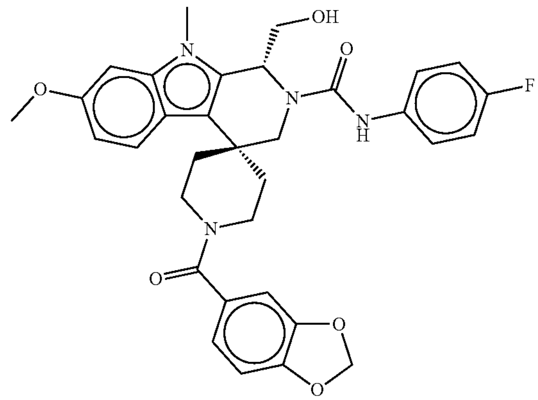 | (R)-1-(benzo[d][1,3]dioxole-5-carbonyl)-N-(4-fluorophenyl)-1'-(hydroxymethyl)-7'-methoxy-9'-methyl-3',9'-dihydrospiro[piperidine-4,4'-pyrido[3,4-b]indole]-2'(1'H)-carboxamide |
| 132 | 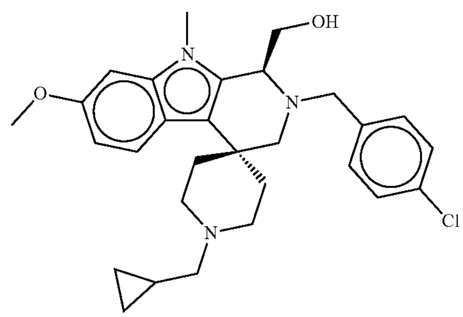 | (S)-(2'-(4-chlorobenzyl)-1-(cyclopropylmethyl)-7'-methoxy-9'-methyl-1',2',3',9'-tetrahydrospiro[piperidine-4,4'-pyrido[3,4-b]indol]-1'-yl)methanol |
| 133 | 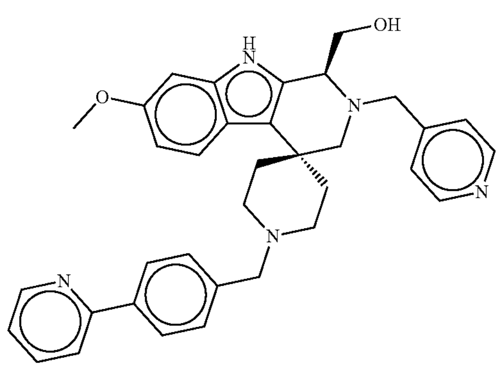 | (S)-(7'-methoxy-1-(4-(pyridin-2-yl)benzyl)-2'-(pyridin-4-ylmethyl)-1',2',3',9'-tetrahydrospiro[piperidine-4,4'-pyrido[3,4-b]indol]-1'-yl)methanol |
| 134 | 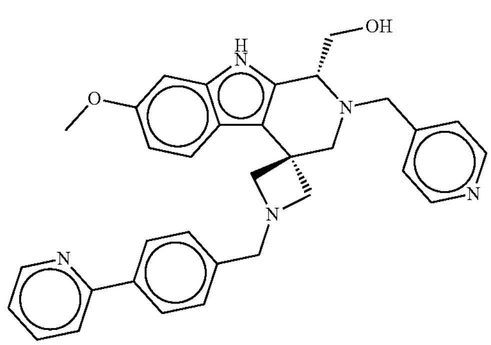 | (R)-(7'-methoxy-1-(4-(pyridin-2-yl)benzyl)-2'-(pyridin-4-ylmethyl)-1',2',3',9'-tetrahydrospiro[azetidine-3,4'-pyrido[3,4-b]indol]-1'-yl)methanol |

TABLE 1-continued

Selected Compounds of the Invention

| Example Number | Structure | Name |
|---|---|---|
| 135 | 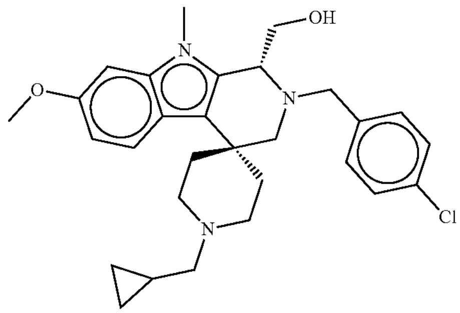 | (R)-(2'-(4-chlorobenzyl)-1-(cyclopropylmethyl)-7'-methoxy-9'-methyl-1',2',3',9'-tetrahydrospiro[piperidine-4,4'-pyrido[3,4-b]indol]-1'-yl)methanol |
| 136 | 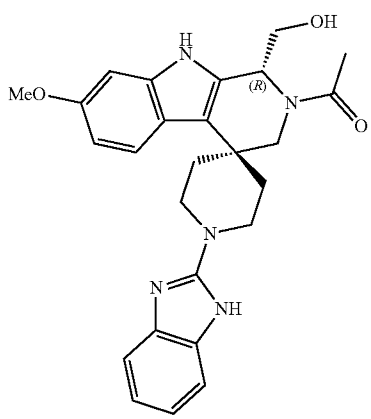 | (R)-1-(1-(1H-benzo[d]imidazol-2-yl)-1'-(hydroxymethyl)-7'-methoxyspiro[piperidine-4,4'-pyrido[3,4-b]indol]-2'(1'H,3'H,9'H)-yl)ethanone |
| 137 | 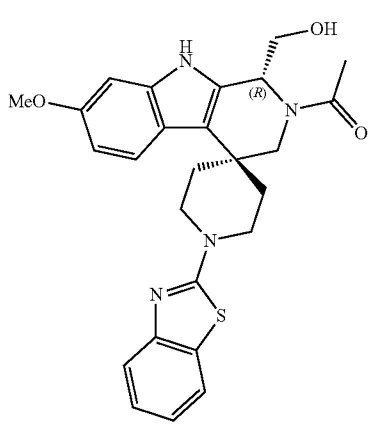 | (R)-1-(1-(benzo[d]thiazol-2-yl)-1'-(hydroxymethyl)-7'-methoxyspiro[piperidine-4,4'-pyrido[3,4-b]indol]-2'(1'H,3'H,9'H)-yl)ethanone |

TABLE 1-continued

Selected Compounds of the Invention

| Example Number | Structure | Name |
|---|---|---|
| 138 | 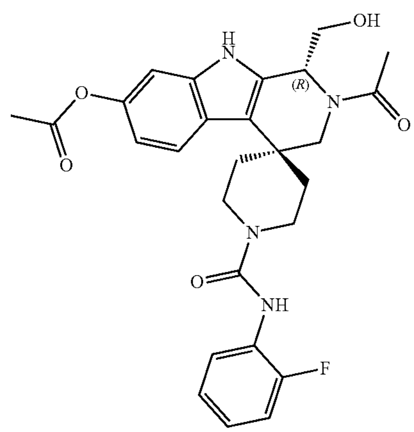 | (R)-1-(1-(benzo[d]thiazol-2-yl)-1'-(hydroxymethyl)-7'-methoxyspiro[piperidine-4,4'-py(R)-2'-acetyl-1-((2-fluorophenyl)carbamoyl)-1'-(hydroxymethyl)-1',2',3',9'-tetrahydrospiro[piperidine-4,4'-pyrido[3,4-b]indol]-7'-yl acetaterido[3,4-b]indol]-2'(1'H,3'H,9'H)-yl)ethanone |
| 139 | 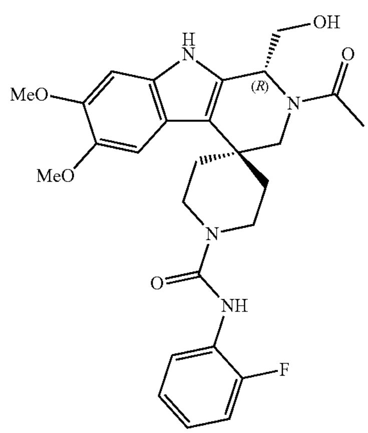 | (R)-2'-acetyl-N-(2-fluorophenyl)-1'-(hydroxymethyl)-6',7'-d imethoxy-1',2',3',9'-tetrahydrospiro[piperidine-4,4'-pyrido[3,4-b]indole]-1-carboxamide |
| 140 | 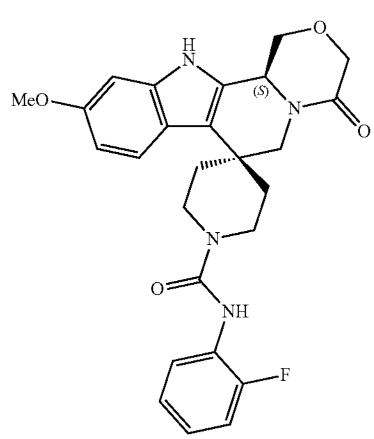 | (S)-N-(2-fluorophenyl)-10-methoxy-4-oxo-1,3,4,6,12,12b-hexahydrospiro[[1,4]oxazino[4',3':1,2]pyrido[3,4-b]indole-7,4'-piperidine]-1'-carboxamide |

TABLE 1-continued

Selected Compounds of the Invention

| Example Number | Structure | Name |
|---|---|---|
| 141 | 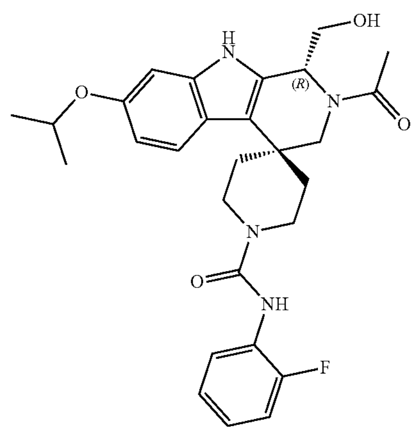 | (R)-2'-acetyl-N-(2-fluorophenyl)-1'-(hydroxymethyl)-7'-isopropoxy-1',2',3',9'-tetrahydrospiro[piperidine-4,4'-pyrido[3,4-b]indole]-1-carboxamide |
| 142 | 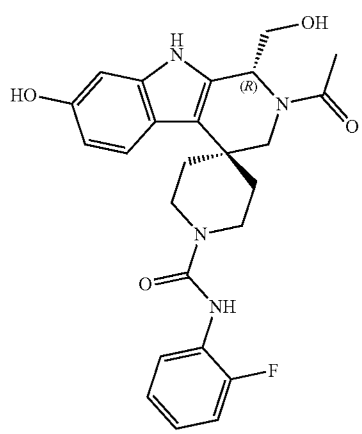 | (R)-2'-acetyl-N-(2-fluorophenyl)-7'-hydroxy-1'-(hydroxymethyl)-1',2',3',9'-tetrahydrospiro[piperidine-4,4'-pyrido[3,4-b]indole]-1-carboxamide |
| 143 | 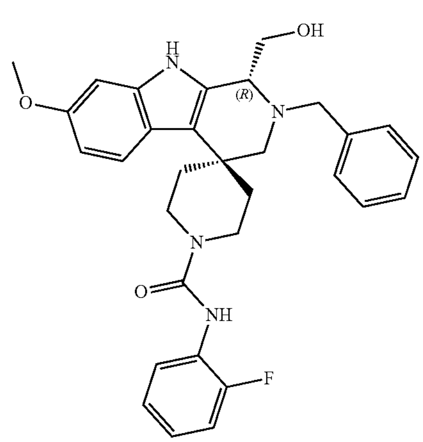 | (R)-2'-benzyl-N-(2-fluorophenyl)-1'-(hydroxymethyl)-7'-methoxy-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 144 | 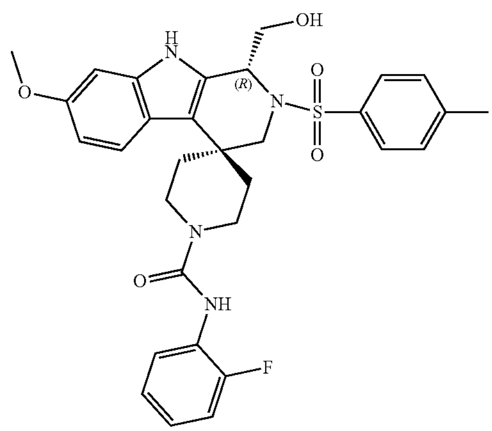 | (R)-N-(2-fluorophenyl)-1'-(hydroxymethyl)-7'-methoxy-2'-tosyl-1',2',3',9'-tetrahydrospiro[piperidine-4,4'-pyrido[3,4-b]indole]-1-carboxamide |
| 145 | 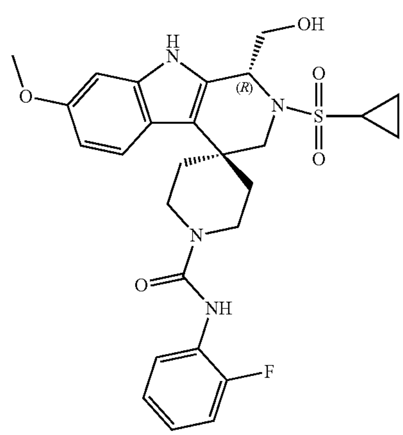 | (R)-2'-(cyclopropylsulfonyl)-N-(2-fluorophenyl)-1'-(hydroxymethyl)-7'-methoxy-1',2',3',9'-tetrahydrospiro[piperidine-4,4'-pyrido[3,4-b]indole]-1-carboxamide |
| 146 | 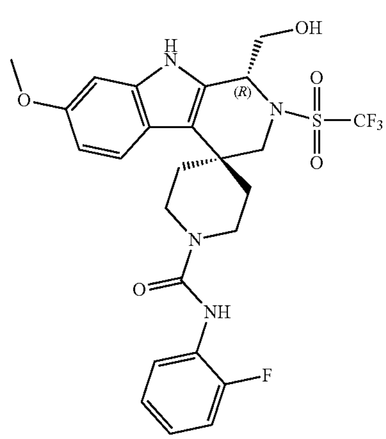 | (R)-N-(2-fluorophenyl)-1'-(hydroxymethyl)-7'-methoxy-2'-((trifluoromethyl)sulfonyl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 147 | 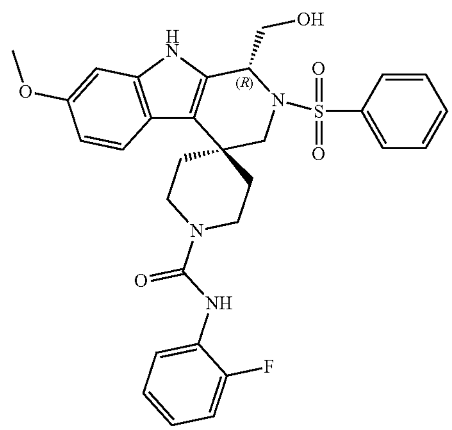 | (R)-N-(2-fluorophenyl)-1'-(hydroxymethyl)-7'-methoxy-2'-(phenylsulfonyl)-1',2',3',9'-tetrahydrospiro[piperidine-4,4'-pyrido+[,4-b]indole]-1-carboxamide |
| 148 | 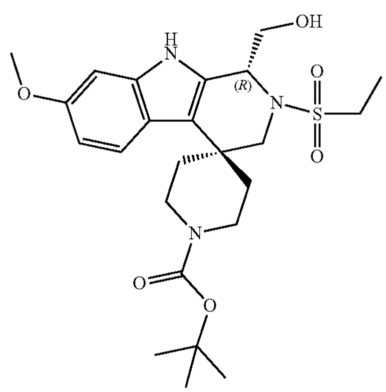 | (R)-tert-butyl 2'-(ethylsulfonyl)-1'-(hydroxymethyl)-7'-methoxy-1',2',3',9'-tetrahydrospiro[piperidine-4,4'-pyrido[3,4-b]indole]-1-carboxylate |
| 149 | 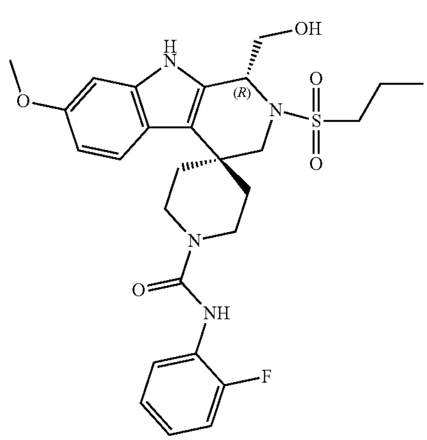 | (R)-N-(2-fluorophenyl)-1'-(hydroxymethyl)-7'-methoxy-2'-(propylsulfonyl)-1',2',3',9'-tetrahydrospiro[piperidine-4,4'-pyrido[3,4-b]indole]-1-carboxamide |

TABLE 1-continued

Selected Compounds of the Invention

| Example Number | Structure | Name |
|---|---|---|
| 150 | 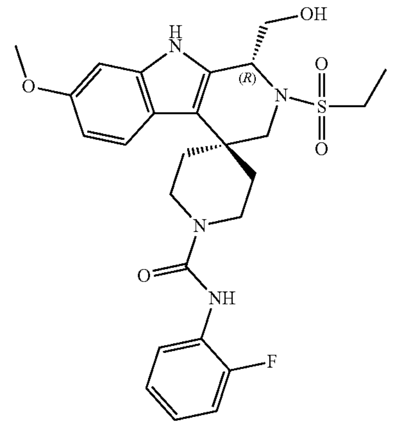 | (R)-2'-(ethylsulfonyl)-N-(2-fluorophenyl)-1'-(hydroxymethyl)-7'-methoxy-1',2',3',9'-tetrahydrospiro[piperidine-4,4'-pyrido[3,4-b]indole]-1-carboxamide |

In some embodiments, the compound of Formula I has a structure of Formula Ia:

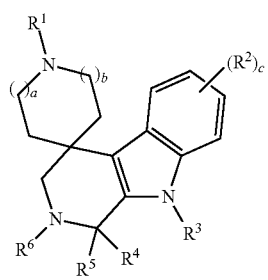

Formula Ia wherein:
a and b, independently of each other, are 0, 1 or 2;
c is 0, 1, 2, 3, or 4;
$R^1$ is—hydrogen,
unsubstituted lower alkyl,
lower alkyl substituted with unsubstituted phenyl or phenyl mono- or di-substituted with halogen,
C(O)—$R^{10}$
S(O)$_2$—$R^{11}$,
benzo-oxazolyl
benzo-imidazolyl
benzo-thiazolyl or
CH$_2$—$R^{19}$;
$R^2$ is—alkoxy
hydroxyl or
halogen;
$R^3$ is—hydrogen or
methyl;
one of $R^4$ or $R^5$ is hydrogen or methyl and the other is hydrogen, methyl, —CH$_2$OH, —CH$_2$NHCH$_3$, —OSi(CH$_3$)$_2$C(CH$_3$)$_3$, —CH$_2$OC(O)CH$_3$, —CH$_2$N(CH$_3$)$_2$, —CH$_2$-morpholinyl, —CH$_2$CH$_3$, —CH$_2$OCH$_2$OCHCH$_2$CHOCH$_3$, —OCH$_2$-phenylmethoxy, —CH$_2$OCH$_2$OCH$_3$, —CH$_2$OCH$_3$, —CH$_2$CH$_2$OH or CH$_2$CF$_3$;
$R^6$ is—hydrogen,
lower alkyl, unsubstituted or substituted with phenyl or halophenyl,
C(O)-lower alkyl,
C(O)CF$_3$,
C(O)CH$_2$-phenyl,
C(O)OCH$_2$C═CH$_2$,
C(O)-cycloalkyl,
S(O)$_2$CH$_3$,
CH$_2$OSi(CH$_3$)$_2$C(CH$_3$)$_3$,
CH$_2$CF$_3$,
C(O)NH-halophenyl,
CH$_2$-benzodioxolyl,
CH$_2$-phenylalkoxy,
CH$_2$-cycloalkyl,
C(O)CH$_2$N(CH$_3$)$_2$,
S(O)$_2$-phenylmethyl,
C(O)-heterocyclyl,
C(O)-halophenyl,
CH$_2$-heterocyclyl,
C(O)-phenyl,
S(O)$_2$-phenyl,
CH$_2$-difluorophenyl
S(O)$_2$-cyclopropyl
S(O)$_2$-trifluoromethyl
S(O)$_2$-ethyl or
CH$_2$-heteroaryl,
or $R^5$ and $R^6$, together with the carbon and nitrogen atoms to which they are respectively attached, combine to form a six-membered heterocyclyl ring optionally substituted with an oxo group,
$R^{10}$ is—unsubstituted lower alkyl,
lower alkyl substituted with heteroaryl,
unsubstituted phenyl,
phenyl mono or bi-substituted with halogen,
benzodioxolyl,
cycloalkyl,
NR$^7$R$^8$ or
OR$^9$;
one of $R^7$ or $R^8$ is hydrogen or lower alkyl and the other is heteroaryl, cycloalkyl, benzodioxolyl, unsubstituted phenyl or phenyl mono- or di-substituted independently with halogen, trifluoromethyl or alkoxy,
$R^9$ is—lower alkyl or
nitrophenyl;
$R^{11}$ is—lower alkyl, CH$_2$-phenyl,
unsubstituted phenyl or
phenyl mono or bi-substituted with halogen; and
R$^{19}$ is—cycloalkyl,
unsubstituted heteroaryl,
heteroaryl substituted with phenyl,
unsubstituted phenyl or
phenyl substituted with heteroaryl or alkoxy;
or a pharmaceutically acceptable salt thereof.

In other embodiments, the compound of Formula I has a structure of Formula IIa:

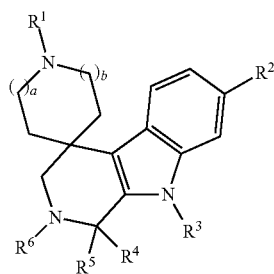

Formula IIa wherein:
a and b, independently of each other, are 0, 1 or 2;
R$^1$ is—hydrogen,
unsubstituted lower alkyl,
lower alkyl substituted with unsubstituted phenyl or phenyl mono- or di-substituted with halogen,
C(O)—R$^{10}$
—S(O)$_2$—R$^{11}$,
benzo-oxazolyl or
CH$_2$—R$^{19}$;
R$^2$ is—alkoxy or
halogen;
R$^3$ is—hydrogen or
methyl;
one of R$^4$ or R$^5$ is hydrogen or methyl and the other is hydrogen, methyl, —CH$_2$OH, —CH$_2$NHCH$_3$, —OSi(CH$_3$)$_2$C(CH$_3$)$_3$, —CH$_2$OC(O)CH$_3$, —CH$_2$N(CH$_3$)$_2$, —CH$_2$-morpholinyl, —CH$_2$CH$_3$, —CH$_2$OCH$_2$OCH$_2$CH$_2$OCH$_3$, —OCH$_2$-phenylmethoxy, —CH$_2$OCH$_2$OCH$_3$, —CH$_2$OCH$_3$, —CH$_2$CH$_2$OH or CH$_2$CF$_3$;
R$^6$ is—hydrogen,
lower alkyl, unsubstituted or substituted with phenyl or halophenyl,
C(O)-lower alkyl,
C(O)CF$_3$,
C(O)CH$_2$-phenyl,
C(O)OCH$_2$C=CH$_2$,
C(O)-cycloalkyl,
S(O)$_2$CH$_3$,
CH$_2$OSi(CH$_3$)$_2$C(CH$_3$)$_3$,
CH$_2$CF$_3$,
C(O)NH-halophenyl,
CH$_2$-benzodioxolyl,
CH$_2$-phenylalkoxy,
CH$_2$-cycloalkyl,
C(O)CH$_2$N(CH$_3$)$_2$,
S(O)$_2$-phenylmethyl,
C(O)-heterocyclyl,
C(O)-halophenyl,
CH$_2$-heterocyclyl,
C(O)-phenyl,
S(O)$_2$-phenyl,
CH$_2$-difluorophenyl or
CH$_2$-heteroaryl,
or R$^5$ and R$^6$, together with the carbon and nitrogen atoms to which they are respectively attached, combine to form a six-membered heterocyclyl ring optionally substituted with an oxo group,
R$^{10}$ is—unsubstituted lower alkyl,
lower alkyl substituted with heteroaryl,
unsubstituted phenyl,
phenyl mono or bi-substituted with halogen,
benzodioxolyl,
cycloalkyl,
NR$^7$R$^8$ or
OR$^9$;
one of R$^7$ or R$^8$ is hydrogen or lower alkyl and the other is heteroaryl, cycloalkyl, benzodioxolyl, unsubstituted phenyl or phenyl mono- or di-substituted independently with halogen, trifluoromethyl or alkoxy,
R$^9$ is—lower alkyl or
nitrophenyl;
R$^{11}$ is—lower alkyl,
CH$_2$-phenyl,
unsubstituted phenyl or
phenyl mono or di-substituted with halogen; and
R$^{19}$ is—cycloalkyl,
unsubstituted heteroaryl,
heteroaryl substituted with phenyl,
unsubstituted phenyl or
phenyl substituted with heteroaryl or alkoxy;
or a pharmaceutically acceptable salt thereof.

In some embodiments of the compounds of Formula Ia or Formula IIa, R$^1$ is hydrogen, benzo-oxazolyl, benzo-imidazolyl, benzo-thiazolyl, unsubstituted lower alkyl, or lower alkyl substituted with unsubstituted phenyl or phenyl mono- or di-substituted with halogen.

In other embodiments of the compounds of Formula Ia or Formula IIa, R$^1$ is hydrogen, benzo-oxazolyl, unsubstituted lower alkyl, or lower alkyl substituted with unsubstituted phenyl or phenyl mono- or di-substituted with halogen.

In certain embodiments of the compounds of Formula Ia or Formula IIa, R$^1$ is —C(O)—R$^{10}$, —S(O)$_2$—R, or —CH$_2$—R$^{19}$, wherein:
R$^{10}$ is—unsubstituted lower alkyl,
lower alkyl substituted with heteroaryl,
unsubstituted phenyl,
phenyl mono or di-substituted with halogen,
benzodioxolyl,
cycloalkyl,
NR$^7$R$^8$ or
OR$^9$;
one of R$^7$ or R$^8$ is hydrogen or lower alkyl and the other is heteroaryl, cycloalkyl, benzodioxolyl, unsubstituted phenyl or phenyl mono- or di-substituted independently with halogen, trifluoromethyl or alkoxy,
R$^9$ is—lower alkyl or
nitrophenyl;
R$^{11}$ is—lower alkyl,
CH$_2$-phenyl,
unsubstituted phenyl or
phenyl mono or di-substituted with halogen; and
R$^{19}$ is—cycloalkyl,
unsubstituted heteroaryl,
heteroaryl substituted with phenyl,
unsubstituted phenyl or
phenyl substituted with heteroaryl or alkoxy.

In some embodiments of the compounds of Formula Ia or Formula IIa, $R^2$ is methoxy, hydroxyl, or fluoro. In other embodiments of the compounds of Formula Ia or Formula IIa, $R^2$ is methoxy or fluoro.

In certain embodiments of the compounds of Formula Ia or Formula IIa, $R^3$ is hydrogen.

In certain embodiments of the compounds of Formula Ia or Formula IIa, $R^6$ is hydrogen or lower alkyl, unsubstituted or substituted with phenyl or halophenyl.

In some embodiments of the compounds of Formula Ia or Formula IIa, $R^6$ is:
C(O)-lower alkyl,
C(O)CF$_3$,
C(O)CH$_2$-phenyl,
C(O)OCH$_2$C=CH$_2$,
C(O)-cycloalkyl,
C(O)NH-halophenyl,
C(O)CH$_2$N(CH$_3$)$_2$,
C(O)-heterocyclyl,
C(O)-halophenyl,
CH$_2$-heterocyclyl
S(O)$_2$-cyclopropyl
S(O)$_2$-trifluoromethyl
S(O)$_2$-ethyl or
C(O)-phenyl.

In other embodiments of the compounds of Formula Ia or Formula IIa, $R^6$ is:
C(O)-lower alkyl,
C(O)CF$_3$,
C(O)CH$_2$-phenyl,
C(O)OCH$_2$C=CH$_2$,
C(O)-cycloalkyl,
C(O)NH-halophenyl,
C(O)CH$_2$N(CH$_3$)$_2$,
C(O)-heterocyclyl,
C(O)-halophenyl,
CH$_2$-heterocyclyl or
C(O)-phenyl.

In certain embodiments of the compounds of Formula Ia or Formula IIa, $R^6$ is:
CH$_2$OSi(CH$_3$)$_2$C(CH$_3$)$_3$,
CH$_2$CF$_3$,
CH$_2$-benzodioxolyl,
CH$_2$-phenylalkoxy,
CH$_2$-cycloalkyl,
CH$_2$-difluorophenyl or
CH$_2$-heteroaryl.

In some embodiments of the compounds of Formula Ia or Formula IIa, $R^6$ is:
S(O)$_2$CH$_3$,
S(O)$_2$-phenylmethyl
S(O)$_2$-cyclopropyl
S(O)$_2$-trifluoromethyl
S(O)$_2$-ethyl or
S(O)$_2$-phenyl.

In other embodiments of the compounds of Formula Ia or Formula IIa, $R^6$ is:
S(O)$_2$CH$_3$,
S(O)$_2$-ethyl or
S(O)$_2$-phenyl.

In certain embodiments of the compounds of Formula Ia or Formula IIa, $R^{10}$ is:
unsubstituted lower alkyl,
lower alkyl substituted with heteroaryl,
unsubstituted phenyl,
phenyl mono or di-substituted with halogen,
benzodioxolyl or
cycloalkyl.

In some embodiments of the compounds of Formula Ia or Formula IIa, $R^{10}$ is —NR$^7$R$^8$ or —OR$^9$.

In some embodiments of the compounds of Formula Ia or Formula IIa, $R^9$ is lower alkyl.

In other embodiments of the compounds of Formula Ia or Formula IIa, $R^{11}$ is lower alkyl or —CH$_2$-phenyl.

In certain embodiments of the compounds of Formula Ia or Formula IIa, $R^{11}$ is unsubstituted phenyl or phenyl mono or di-substituted with halogen.

In some embodiments of the compounds of Formula Ia or Formula IIa, $R^{19}$ is cycloalkyl, unsubstituted heteroaryl or heteroaryl substituted with phenyl.

In other embodiments of the compounds of Formula Ia or Formula IIa, $R^{19}$ is unsubstituted phenyl or phenyl substituted with heteroaryl or alkoxy.

In certain embodiments of the compounds of Formula Ia or Formula IIa, a is 1. In some embodiments of the compounds of Formula Ia or Formula IIa, b is 1. In other embodiments of the compounds of Formula Ia or Formula IIa, a is 0. In certain embodiments of the compounds of Formula Ia or Formula IIa, b is 0. In some embodiments of the compounds of Formula Ia or Formula IIa, both a and b are 1. In other embodiments of the compounds of Formula Ia or Formula IIa, both a and b are 0. In certain embodiments of the compounds of Formula Ia or Formula IIa, a is 1 and b is 0.

In another aspect, the invention features a pharmaceutical composition, including a therapeutically effective amount of a compound of Formula VIII:

Formula VIII

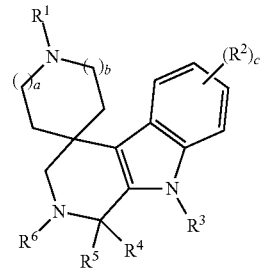

wherein a and b are independently 0, 1, or 2;
c is 0, 1, 2, 3, or 4;
$R^1$ is hydrogen, $C_1$-$C_6$ alkyl, $C_2$-$C_9$ heteroaryl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, —C(O)NR$^7$R$^8$, —C(O)OR$^9$, —C(O)R$^{10}$, or —S(O)$_2$R$^{11}$;
each $R^2$ is independently hydroxyl, halogen, or —OR$^{12}$;
$R^3$ is hydrogen or $C_1$-$C_6$ alkyl;
$R^4$ is hydrogen or $C_1$-$C_6$ alkyl;
$R^5$ is $C_1$-$C_6$ alkyl, or —(CH$_2$)$_n$X$^1$R$^{13}$, or $R^5$ and $R^6$ together with the carbon and nitrogen atoms to which they are respectively attached, combine to form a 5-8-membered heterocycle;
$R^6$ is hydrogen, $C_1$-$C_6$ alkyl, $C_1$-$C_6$ perfluoroalkyl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, $C_2$-$C_9$ heterocyclyl $C_1$-$C_6$ alkyl, N-protecting group, —C(O)R$^{15}$, —C(O)NR$^{16}$R$^{17}$, or —S(O)$_2$R$^{18}$;
$R^7$ is hydrogen or $C_1$-$C_6$ alkyl;
$R^8$ is $C_6$-$C_{10}$ aryl, $C_2$-$C_9$ heteroaryl, $C_2$-$C_9$ heterocyclyl, or $C_3$-$C_{10}$ carbocyclyl;
$R^9$ is $C_1$-$C_6$ alkyl or $C_6$-$C_{10}$ aryl;

$R^{10}$ is $C_1$-$C_6$ alkyl, $C_6$-$C_{10}$ aryl, $C_2$-$C_9$ heterocyclyl, $C_6$-$C_{10}$ aryl $C_1$-$C_6$ alkyl, or $C_2$-$C_9$ heteroaryl $C_1$-$C_6$ alkyl;

$R^{11}$ is $C_1$-$C_6$ alkyl, $C_6$-$C_{10}$ aryl, or $C_6$-$C_{10}$ aryl $C_1$-$C_6$ alkyl;

each $R^{12}$ is $C_1$-$C_6$ alkyl or $C_1$-$C_6$ acyl;

n is 1, 2, 3, 4, 5, or 6;

$X^1$ is absent, O, or $NR^{14}$;

$R^{13}$ is hydrogen, $C_1$-$C_6$ alkyl, $C_1$-$C_6$ heteroalkyl, $C_1$-$C_6$ perfluoroalkyl, $C_1$-$C_6$ acyl, $C_6$-$C_{10}$ aryl $C_1$-$C_6$ alkyl, an O- or N-protecting group, or $R^{13}$ and $R^{14}$ combine to form a 5-8-membered heterocycle;

$R^{14}$ is hydrogen or $C_1$-$C_6$ alkyl;

$R^{15}$ is $C_1$-$C_6$ alkyl, $C_1$-$C_6$ perfluoroalkyl, $C_1$-$C_6$ heteroalkyl, $C_3$-$C_{10}$ carbocyclyl, $C_2$-$C_9$ heterocyclyl, $C_6$-$C_{10}$ aryl, $C_6$-$C_{10}$ aryl $C_1$-$C_6$ alkyl;

$R^{16}$ and $R^{17}$ are independently hydrogen, $C_1$-$C_6$ alkyl, or $C_6$-$C_{10}$ aryl; and $R^{18}$ is $C_1$-$C_6$ alkyl, $C_1$-$C_6$ perfluoroalkyl, $C_3$-$C_{10}$ carbocyclyl, or $C_6$-$C_{10}$ aryl; or a pharmaceutically acceptable salt thereof and a pharmaceutically acceptable carrier.

In another aspect, the invention features a method of treating malaria (e.g., malaria caused by P. falciparum, P. vivax, P. ovale, P. malariae, or P. knowles) in a subject. This method includes the step of administering to the subject a therapeutically effective amount of any of the foregoing compositions or a compound of Formula VIII:

Formula VIII

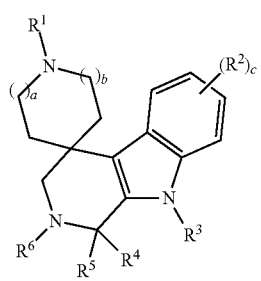

wherein a and b are independently 0, 1, or 2;

c is 0, 1, 2, 3, or 4;

$R^1$ is hydrogen, $C_1$-$C_6$ alkyl, $C_2$-$C_9$ heteroaryl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, —C(O)$NR^7R^8$, —C(O)$OR^9$, —C(O)$R^{10}$, or —S(O)$_2R^{11}$;

each $R^2$ is independently hydroxyl, halogen, or —$OR^{12}$;

$R^3$ is hydrogen or $C_1$-$C_6$ alkyl;

$R^4$ is hydrogen or $C_1$-$C_6$ alkyl;

$R^5$ is $C_1$-$C_6$ alkyl, or —$(CH_2)_nX^1R^{13}$, or $R^5$ and $R^6$ together with the carbon and nitrogen atoms to which they are respectively attached, combine to form a 5-8-membered heterocycle;

$R^6$ is hydrogen, $C_1$-$C_6$ alkyl, $C_1$-$C_6$ perfluoroalkyl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, $C_2$-$C_9$ heterocyclyl $C_1$-$C_6$ alkyl, N-protecting group, —C(O)$R^{15}$, —C(O)$NR^{16}R^{17}$, or —S(O)$_2R^{18}$;

$R^7$ is hydrogen or $C_1$-$C_6$ alkyl;

$R^8$ is $C_6$-$C_{10}$ aryl, $C_2$-$C_9$ heteroaryl, $C_2$-$C_9$ heterocyclyl, or $C_3$-$C_{10}$ carbocyclyl;

$R^9$ is $C_1$-$C_6$ alkyl or $C_6$-$C_{10}$ aryl;

$R^{10}$ is $C_1$-$C_6$ alkyl, $C_6$-$C_{10}$ aryl, $C_2$-$C_9$ heterocyclyl, $C_6$-$C_{10}$ aryl $C_1$-$C_6$ alkyl, or $C_2$-$C_9$ heteroaryl $C_1$-$C_6$ alkyl;

$R^{11}$ is $C_1$-$C_6$ alkyl, $C_6$-$C_{10}$ aryl, or $C_6$-$C_{10}$ aryl $C_1$-$C_6$ alkyl;

each $R^{12}$ is $C_1$-$C_6$ alkyl or $C_1$-$C_6$ acyl;

n is 1, 2, 3, 4, 5, or 6;

$X^1$ is absent, O, or $NR^{14}$;

$R^{13}$ is hydrogen, $C_1$-$C_6$ alkyl, $C_1$-$C_6$ heteroalkyl, $C_1$-$C_6$ perfluoroalkyl, $C_1$-$C_6$ acyl, $C_6$-$C_{10}$ aryl $C_1$-$C_6$ alkyl, an O- or N-protecting group, or $R^{13}$ and $R^{14}$ combine to form a 5-8-membered heterocycle;

$R^{14}$ is hydrogen or $C_1$-$C_6$ alkyl;

$R^{15}$ is $C_1$-$C_6$ alkyl, $C_1$-$C_6$ perfluoroalkyl, $C_1$-$C_6$ heteroalkyl, $C_3$-$C_{10}$ carbocyclyl, $C_2$-$C_9$ heterocyclyl, $C_6$-$C_{10}$ aryl, $C_6$-$C_{10}$ aryl $C_1$-$C_6$ alkyl;

$R^{16}$ and $R^{17}$ are independently hydrogen, $C_1$-$C_6$ alkyl, or $C_6$-$C_{10}$ aryl; and $R^{18}$ is $C_1$-$C_6$ alkyl, $C_1$-$C_6$ perfluoroalkyl, $C_3$-$C_{10}$ carbocyclyl, or $C_6$-$C_{10}$ aryl;

or a pharmaceutically acceptable salt thereof to a patient in need thereof.

In some embodiments of any of the foregoing methods or compositions, the compound of Formula VIII is not compound 12, compound 15, or any one of compounds 78-135 of Table 1.

In some embodiments of any of the foregoing methods or compositions, c is 1. In other embodiments of any of the foregoing methods or compositions, c is 2.

In certain embodiments of any of the foregoing methods or compositions, the compound has a structure of Formula IX:

Formula IX

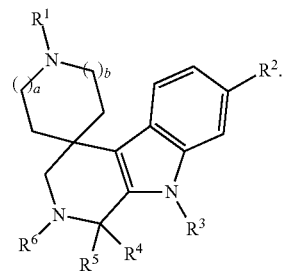

In other embodiments of any of the foregoing methods or compositions, the compound has a structure of Formula X:

Formula X

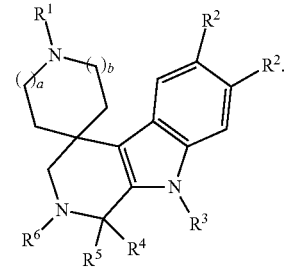

In some embodiments of any of the foregoing methods or compositions, the compound has a structure of Formula XI:

Formula XI

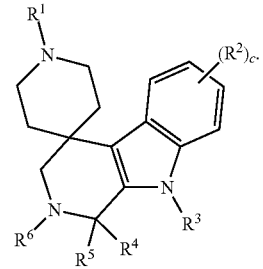

In certain embodiments of any of the foregoing methods or compositions, the compound has the structure:

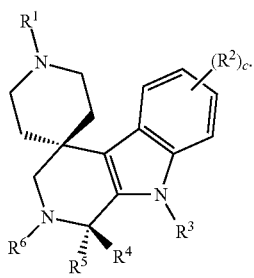

In other embodiments of any of the foregoing methods or compositions, the compound has a structure of Formula XII:

Formula XII

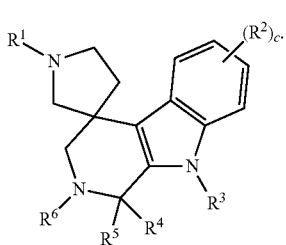

In certain embodiments of any of the foregoing methods or compositions, the compound has the structure:

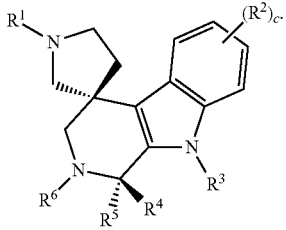

In some embodiments of any of the foregoing methods or compositions, the compound has a structure of Formula XIII:

Formula XIII

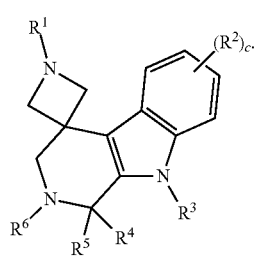

In certain embodiments of any of the foregoing methods or compositions, the compound has the structure:

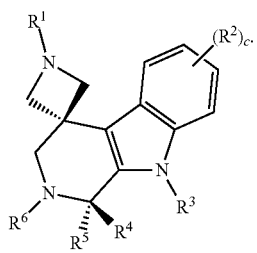

In some embodiments of any of the foregoing methods or compositions, $R^3$ is hydrogen. In other embodiments of any of the foregoing methods or compositions, $R^3$ is $C_1$-$C_6$ alkyl (e.g., methyl). In certain embodiments of any of the foregoing methods or compositions, $R^4$ is hydrogen. In some embodiments of any of the foregoing methods or compositions, $R^4$ is $C_1$-$C_6$ alkyl (e.g., methyl).

In other embodiments of any of the foregoing methods or compositions, $R^2$ is hydroxyl. In certain embodiments of any of the foregoing methods or compositions, $R^2$ is halogen (e.g., fluoro). In some embodiments of any of the foregoing methods or compositions, $R^2$ is —$OR^{12}$ (e.g., $R^{12}$ is $C_1$-$C_6$ alkyl, such as methyl or isopropyl or $C_1$-$C_6$ acyl, such as acetyl).

In certain embodiments of any of the foregoing methods or compositions, $R^5$ and $R^6$ together with the carbon and nitrogen atoms to which they are respectively attached, combine to form a 5-8-membered heterocycle (e.g., a 6-membered heterocycle substituted with an oxo).

In some embodiments of any of the foregoing methods or compositions, the compound has the structure of Formula XIV:

Formula XVI

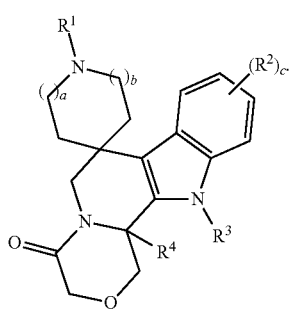

In other embodiments of any of the foregoing methods or compositions, $R^5$ is $C_1$-$C_6$ alkyl (e.g., methyl).

In certain embodiments of any of the foregoing methods or compositions, $R^5$ is —$(CH_2)_nX^1R^{13}$. In some embodiments of any of the foregoing methods or compositions, n is 1. In other embodiments of any of the foregoing methods or compositions, n is 2. In certain embodiments of any of the foregoing methods or compositions, $X^1$ is absent. In some embodiments of any of the foregoing methods or compositions, $R^{13}$ is $C_1$-$C_6$ perfluoroalkyl (e.g., trifluoromethyl). In other embodiments of any of the foregoing methods or compositions, $X^1$ is O. In certain embodiments of any of the foregoing methods or compositions, $R^{13}$ is hydrogen, $C_1$-$C_6$ alkyl (e.g., methyl), $C_1$-$C_6$ heteroalkyl (e.g., —$CH_2OCH_3$ or —$CH_2$, $OCHCH_2CH_2OCH_3$), $C_1$-$C_6$ acyl (e.g., acetyl), $C_6$-$C_{10}$ aryl $C_1$-$C_6$ alkyl (e.g., 4-methoxybenzyl), or an O-protecting group (e.g., tertbutyldimethylsilyl). In some embodiments of any of the foregoing methods or compositions, $X^1$ is $NR^{14}$. In other embodiments of any of the foregoing methods or compositions, $R^{13}$ and $R^{14}$ combine to form a 5-8-membered heterocycle (e.g., morpholino). In certain embodiments of any of the foregoing methods or compositions, $R^{14}$ is hydrogen. In some embodiments of any of the foregoing methods or compositions, $R^{14}$ is $C_1$-$C_6$ alkyl (e.g., methyl). In some embodiments of any of the foregoing methods or compositions, $R^{13}$ is $C_1$-$C_6$ alkyl (e.g., methyl).

In other embodiments of any of the foregoing methods or compositions, $R^1$ is hydrogen.

In certain embodiments of any of the foregoing methods or compositions, $R^1$ is $C_1$-$C_6$ alkyl (e.g., methyl, ethyl, or n-propyl).

In some embodiments of any of the foregoing methods or compositions, $R^1$ is $C_2$-$C_9$ heteroaryl (e.g., benzo-oxazolyl, benzo-imidazolyl, or benzo-thiazolyl).

In other embodiments of any of the foregoing methods or compositions, $R^1$ is $C_3$-$C_{10}$ carbocyclyl $C_1$-$C_6$ alkyl (e.g., cyclopropylmethyl, cyclopentylmethyl, or cyclohexylmethyl).

In certain embodiments of any of the foregoing methods or compositions, $R^1$ is $C_6$-$C_{10}$ aryl $C_1$-$C_6$ alkyl (e.g., 2-fluorophenyl-ethyl, 2-fluorobenzyl, 4-(2-pyridyl)-benzyl, 4-methoxybenzyl, or 3-fluorobenzyl).

In some embodiments of any of the foregoing methods or compositions, $R^1$ is $C_2$-$C_9$ heteroaryl $C_1$-$C_6$ alkyl (e.g., 2-pyridyl-methyl, 3-pyridyl-methyl, 3,5-pyrimidyl-methyl, thiazolyl-methyl, or (3-phenyl-oxazolyl)-methyl).

In other embodiments of any of the foregoing methods or compositions, $R^1$ is —C(O)$NR^7R^8$. In certain embodiments of any of the foregoing methods or compositions, $R^7$ is hydrogen. In some embodiments of any of the foregoing methods or compositions, $R^7$ is $C_1$-$C_6$ alkyl (e.g., methyl). In some embodiments of any of the foregoing methods or compositions, $R^8$ is $C_6$-$C_{10}$ aryl (e.g., 2-chlorophenyl, 2-fluorophenyl, 2-trifluoromethylphenyl, 3-chlorophenyl, 3-fluorophenyl, 4-fluorophenyl, 4-chlorophenyl, 4-methoxyphenyl, 2,3-difluorophenyl, 2,4-difluorophenyl, 2,5-difluorophenyl, 2,6-difluorophenyl, or 3,4-difluorophenyl). In other embodiments of any of the foregoing methods or compositions, $R^8$ is $C_2$-$C_9$ heteroaryl (e.g., 2-pyridyl or 3-pyridyl). In certain embodiments of any of the foregoing methods or compositions, $R^8$ is $C_2$-$C_9$ heterocyclyl (e.g., benzodioxolyl). In some embodiments of any of the foregoing methods or compositions, $R^8$ is $C_3$-$C_{10}$ carbocyclyl (e.g., cyclohexyl).

In other embodiments of any of the foregoing methods or compositions, $R^1$ is —C(O)$OR^9$. In certain embodiments of any of the foregoing methods or compositions, $R^9$ is $C_1$-$C_6$ alkyl (e.g., tertbutyl). In some embodiments of any of the foregoing methods or compositions, $R^9$ is $C_6$-$C_{10}$ aryl (e.g., 4-nitrophenyl).

In other embodiments of any of the foregoing methods or compositions, $R^1$ is —C(O)$R^{10}$. In certain embodiments of any of the foregoing methods or compositions, $R^{10}$ is $C_1$-$C_6$ alkyl (e.g., ethyl or n-propyl). In some embodiments of any of the foregoing methods or compositions, $R^{10}$ is $C_6$-$C_{10}$ aryl (e.g., phenyl or 2-fluorophenyl). In other embodiments of any of the foregoing methods or compositions, $R^{10}$ is $C_2$-$C_9$ heterocyclyl (e.g., benzodioxolyl). In certain embodiments of any of the foregoing methods or compositions, $R^{10}$ is $C_6$-$C_{10}$ aryl $C_1$-$C_6$ alkyl (e.g., 2-fluorobenzyl). In some embodiments of any of the foregoing methods or compositions, $R^{10}$ is $C_2$-$C_9$ heteroaryl $C_1$-$C_6$ alkyl (e.g., 3-pyridyl-methyl).

In other embodiments of any of the foregoing methods or compositions, $R^1$ is —S(O)$_2R^{11}$. In certain embodiments of any of the foregoing methods or compositions, $R^{11}$ is $C_1$-$C_6$ alkyl (e.g., ethyl). In some embodiments of any of the foregoing methods or compositions, $R^1$ is $C_6$-$C_{10}$ aryl (e.g., phenyl, 2-fluorophenyl, 3-fluorophenyl, 3-methoxyphenyl, or 4-methoxyphenyl). In other embodiments of any of the foregoing methods or compositions, $R^{11}$ is $C_6$-$C_{10}$ aryl $C_1$-$C_6$ alkyl (e.g., 2-fluorobenzyl).

In certain embodiments of any of the foregoing methods or compositions, $R^6$ is hydrogen. In some embodiments of any of the foregoing methods or compositions, $R^6$ is $C_1$-$C_6$ alkyl (e.g., methyl, ethyl, n-propyl, or 2,2,2-trifluoroethyl). In certain embodiments of any of the foregoing methods or compositions, $R^6$ is $C_3$-$C_{10}$ carbocyclyl $C_1$-$C_6$ alkyl (e.g., cyclopropylmethyl or cyclohexylmethyl). In some embodiments of any of the foregoing methods or compositions, $R^6$ is $C_6$-$C_{10}$ aryl $C_1$-$C_6$ alkyl (e.g., benzyl, 2-methoxybenzyl, 3-methoxybenzyl, 4-chlorobenzyl, 2,5-difluorobenzyl, phenyl-ethyl, or phenyl-propyl). In other embodiments of any of the foregoing methods or compositions, $R^6$ is $C_2$-$C_9$ heteroaryl $C_1$-$C_6$ alkyl (e.g., 2-pyridyl-methyl). In certain embodiments of any of the foregoing methods or compositions, $R^6$ is $C_2$-$C_9$ heterocyclyl $C_1$-$C_6$ alkyl (e.g., benzodioxolyl-methyl). In some embodiments of any of the foregoing methods or compositions, $R^6$ is an N-protecting group (e.g., allyloxycarbonyl, i.e., alloc.

In other embodiments of any of the foregoing methods or compositions, $R^6$ is —C(O)$R^{15}$. In certain embodiments of any of the foregoing methods or compositions, $R^{15}$ is $C_1$-$C_6$ alkyl (e.g., methyl, ethyl, n-propyl, isopropyl, or tertbutyl). In some embodiments of any of the foregoing methods or compositions, $R^{15}$ is $C_1$-$C_6$ perfluoroalkyl (e.g., trifluoromethyl). In other embodiments of any of the foregoing methods or compositions, $R^{15}$ is $C_1$-$C_6$ heteroalkyl (e.g., —CH$_2$N(CH$_3$)$_2$). In certain embodiments of any of the foregoing methods or compositions, $R^{15}$ is $C_3$-$C_{10}$ carbocyclyl (e.g., cyclopropyl, cyclobutyl, cyclopentyl, or cyclohexyl). In some embodiments of any of the foregoing methods or compositions, $R^{15}$ is $C_2$-$C_9$ heterocyclyl (e.g., pyranyl). In other embodiments of any of the foregoing methods or compositions, $R^{15}$ is $C_6$-$C_{10}$ aryl (e.g., phenyl or 4-fluorophenyl). In certain embodiments of any of the foregoing methods or compositions, $R^{15}$ is $C_6$-$C_{10}$ aryl $C_1$-$C_6$ alkyl (e.g., benzyl).

In some embodiments of any of the foregoing methods or compositions, $R^6$ is —C(O)$NR^{16}R^{17}$. In other embodiments of any of the foregoing methods or compositions, $R^{16}$ is hydrogen. In certain embodiments of any of the foregoing methods or compositions, $R^{17}$ is $C_6$-$C_{10}$ aryl (e.g., 4-fluorophenyl).

In some embodiments of any of the foregoing methods or compositions, $R^6$ is —S(O)$_2R^{18}$. In other embodiments of any of the foregoing methods or compositions, $R^{18}$ is $C_1$-$C_6$ alkyl (e.g., methyl, ethyl, or n-propyl). In certain embodiments of any of the foregoing methods or compositions, $R^{18}$ is $C_1$-$C_6$ perfluoroalkyl (e.g., trifluoromethyl). In some embodiments of any of the foregoing methods or compositions, $R^{18}$ is $C_3$-$C_{10}$ carbocyclyl (e.g., cyclopropyl). In other embodiments of any of the foregoing methods or compositions, $R^{18}$ is $C_6$-$C_{10}$ aryl (e.g., phenyl or 4-methylphenyl).

In some embodiments of any of the foregoing compositions or methods, the compound is selected from any one of compounds 1 to 150 of Table 1 or a pharmaceutically acceptable salt thereof.

In some embodiments of any of the foregoing methods, the malaria is drug resistant (e.g., the malaria is resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof).

In some embodiments, the malaria is liver stage.

Chemical Terms

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

The term "acyl," as used herein, represents a hydrogen or an alkyl group, as defined herein, that is attached to the parent molecular group through a carbonyl group, as defined herein, and is exemplified by formyl (i.e., a carboxaldehyde group), acetyl, trifluoroacetyl, propionyl, and butanoyl. Exemplary unsubstituted acyl groups include from 1 to 6, from 1 to 11, or from 1 to 21 carbons. In some embodiments, the alkyl group is further substituted with 1, 2, 3, or 4 substituents as described herein.

As used herein, the term "alkyl", alone or in combination with other groups, refers to a branched or straight-chain monovalent saturated aliphatic hydrocarbon radical of one to twenty carbon atoms (e.g., one to sixteen carbon atoms, one to ten carbon atoms, one to six carbon atoms).

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, and 2-ethylbutyl.

As used herein, the term "alkenyl", alone or in combination with other groups, refers to a straight-chain or branched hydrocarbon residue having an olefinic bond.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or heterocyclylalkyl (e.g., heteroarylalkyl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or —NHR$^{N1}$, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, C$_{1-20}$ alkyl (e.g., C$_{1-6}$ alkyl), or C$_{6-10}$ aryl.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, and 1H-indenyl.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as C$_{1-6}$ alk-C$_{6-10}$ aryl, C$_{1-10}$ alk-C$_{6-10}$ aryl, or C$_{1-20}$ alk-C$_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a C$_{1-6}$ alkylene, unless otherwise noted, and the attached chemical structure is as defined herein.

The alkyl, lower alkyl, carbocyclic, and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, aryloxy, alkoxyalkyl, aryloxyalkyl, more preferably, for example, methoxy and ethoxy), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "azido" represents an —N$_3$ group, which can also be represented as —N=N=N.

The terms "carbocyclic" and "carbocyclyl," as used herein, refer to an optionally substituted non-aromatic C$_{3-12}$ monocyclic, bicyclic, or tricyclic structure in which the rings are formed by carbon atoms. Carbocyclic structures include cycloalkyl, cycloalkenyl, and cycloalkynyl groups.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, and indanyl. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, and optionally substituted cycloheptyl, or those which are specifically exemplified herein.

The "carbocyclylalkyl" group, which as used herein, represents a carbocyclyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "carbonyl," as used herein, represents a C(O) group, which can also be represented as C=O.

The term "carboxy," as used herein, means —$CO_2H$.

The term "cyano," as used herein, represents an —CN group.

As used herein, the term "halogen" means a fluorine (fluoro), chlorine (chloro), bromine (bromo) or iodine (iodo) radical.

The term "heteroalkyl," as used herein, refers to an alkyl group, as defined herein, in which one or more of the constituent carbon atoms have each been replaced by nitrogen, oxygen, or sulfur. In some embodiments, the heteroalkyl group can be further substituted with 1, 2, 3, or 4 substituent groups as described herein for alkyl groups. The term "heteroalkenyl," as used herein refers to alkenyl groups, as defined herein, respectively, in which one or more of the constituent carbon atoms have each been replaced by nitrogen, oxygen, or sulfur. In some embodiments, the heteroalkenyl groups can be further substituted with 1, 2, 3, or 4 substituent groups as described herein for alkyl groups. Examples of heteroalkyl groups are an "alkoxy" which, as used herein, refers alkyl-O—; and "alkoyl" which, as used herein, refers to alkyl-CO—. Alkoxy substituent groups or alkoxy-containing substituent groups may be substituted by, for example, one or more alkyl groups.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are benzooxazolyl, benzoimidazolyl, and benzothiazolyl.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl" denotes a mono- or polycyclic alkyl ring, wherein one, two or three of the carbon ring atoms is replaced by a heteroatom such as N, O or S. Examples of hetereocyclyl groups include, but are not limited to, morpholinyl, thiomorpholinyl, piperazinyl, piperidinyl, pyrrolidinyl, tetrahydropyranyl, tetrahydrofuranyl, and 1,3-dioxanyl. The heterocyclyl groups may be unsubstituted or substituted, and attachment may be through their carbon frame or through their heteroatom(s) where appropriate.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-12}$ heterocyclyl $C_{1-6}$ alkyl, $C_{1-12}$ heterocyclyl $C_{1-10}$ alkyl, or $C_{1-12}$ heterocyclyl) $C_{1-20}$ alkyl. In some embodiments, the alkylene and the heterocyclyl each can be further substituted with 1, 2, 3, or 4 substituent groups as defined herein for the respective group.

The heterocyclyl, heterocyclyl, and heteroaryl groups described above may be substituted independently with one, two, three, or more substituents. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, aryloxy, alkoxyalkyl, aryloxyalkyl), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazolyl and carbolinyl).

The term "hydroxyl," as used herein, represents an —OH group. In some embodiments, the hydroxyl group can be substituted with a O-protecting group as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

The term "oxo" as used herein, represents=O.

The term "perfluoroalkyl," as used herein, represents alkyl group, as defined herein, where each hydrogen radical bound to the alkyl group has been replaced by a fluoride radical. For example, perfluoroalkyl groups are exemplified by trifluoromethyl and pentafluoroethyl.

The term "sulfonyl," as used herein, represents an —S(O)$_2$— group.

The term "thiol," as used herein, represents an —SH group.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

DEFINITIONS

In the practice of the method of the present invention, an "effective amount" of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

As used herein, the term "patient" refers to any organism to which a composition in accordance with the invention may be administered, e.g., for experimental, diagnostic, prophylactic, and/or therapeutic purposes. Typical patients include any animal (e.g., mammals such as mice, rats, rabbits, non-human primates, and humans). A subject may seek or be in need of treatment, require treatment, be receiving treatment, may be receiving treatment in the future, or a human or animal who is under care by a trained professional for a particular disease or condition.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Useful pharmaceutical carriers for the preparation of the compositions hereof, can be solids, liquids or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, and various amines for forming basic salts. Methods for preparation of the appropriate salts are well-established in the art.

Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, and p-toluenesulfonic. Particularly preferred are fumaric, hydrochloric, hydrobromic, phosphoric, succinic, sulfuric and methanesulfonic acids. Acceptable base salts include alkali metal (e.g., sodium, potassium), alkaline earth metal (e.g., calcium, magnesium) and aluminum salts.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, and as well understood in the art, "to treat" a condition or "treatment" of the condition (e.g., the conditions described herein such as malaria) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver, preventing systemic disease, preventing the symptomatic stage of malaria, and/or preventing establishment of *Plasmodium* infection); delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup.

BRIEF DESCRIPTION OF THE DRAWING

FIG. 1 is an image illustrating the results of a liver stage in vivo assay utilizing transgenic parasites (*P. berghei* (ANKA GFP-luc) sporozoites), atovaquone (ATV), and compound 15.

DETAILED DESCRIPTION OF THE INVENTION

Compounds

The invention features compounds that are useful in the prevention and treatment of malaria. Exemplary compounds described herein include compounds 1-150 shown above in Table 1 and compounds having a structure according to any of Formulae I-VII or a pharmaceutically acceptable salt thereof.

Formula I
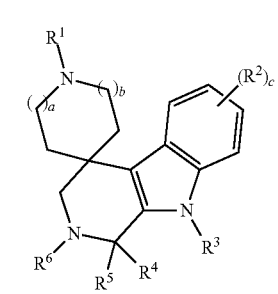

Formula II
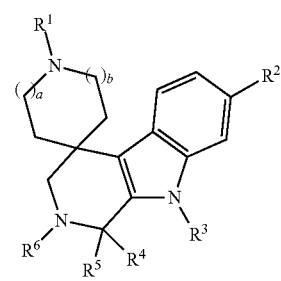

Formula III
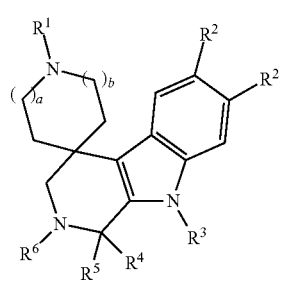

Formula IV
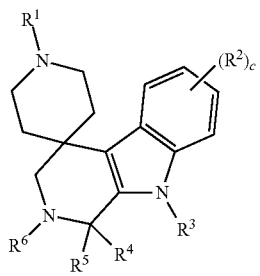

Formula V
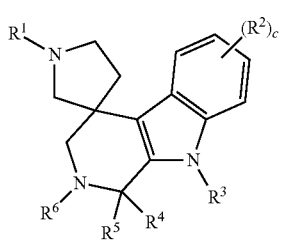

Formula VI
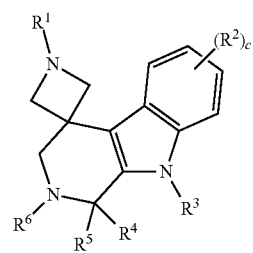

Formula VII
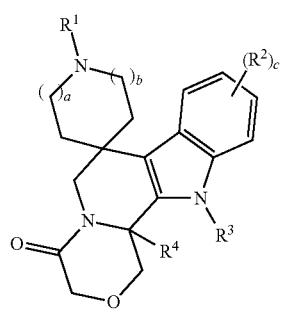

Other embodiments, as well as exemplary methods for the synthesis or production of these compounds, are described herein.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

Utility and Administration

The compounds described herein are useful in the methods of the invention and, while not bound by theory, are believed to exert their desirable effects through their ability to inhibit the growth of or kill the parasitic protozoan which causes malaria (e.g., *P. falciparum, P. vivax, P. ovale, P. malariae, P. knowlesi*). In some embodiments, the treatment of malaria includes causative prophylaxis, such as preventing the spread of plasmodium infection beyond the liver, preventing systemic disease, preventing the symptomatic stage of malaria, and/or preventing the establishment of the infection. In some embodiments, the treatment of malaria refers to treatment intended to achieve cure (e.g., of *P. vivax* or *P. malariae*), e.g., treatment for radical cure (i.e., clearing hypnozoites from the liver). In various examples, the methods include preventing spread of infection of a malaria-causing parasite as described herein from the liver.

The compounds of the invention may be useful in the treatment of drug resistant malaria, such as malaria resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, and any combination thereof.

For use as treatment of human and animal subjects, the compounds of the invention can be formulated as pharmaceutical or veterinary compositions. Depending on the subject to be treated, the mode of administration, and the type of treatment desired (e.g., prevention, prophylaxis, or therapy) the compounds are formulated in ways consonant with these parameters. A summary of such techniques is found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

The compounds described herein may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, the compounds described herein may be used alone, as mixtures of two or more compounds or in combination with other pharmaceuticals. An example of other pharmaceuticals to combine with the compounds described herein would include pharmaceuticals for the treatment of the same indication. Another example of a potential pharmaceutical to combine with the compounds described herein would include pharmaceuticals for the treatment of different yet associated or related symptoms or indications. Depending on the mode of administration, the compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

The compounds of the invention may be prepared and used as pharmaceutical compositions comprising an effective amount of a compound described herein and a pharmaceutically acceptable carrier or excipient, as is well known in the art. In some embodiments, the composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, and preservatives. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, and glycerol. Such compositions may also contain amounts of nontoxic auxiliary substances such as wetting or emulsifying agents, and pH buffering agents, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, or two topical creams. The kit can include optional components that aid in the administration of the unit dose to subjects, such as vials for reconstituting powder forms, syringes for injection, customized IV delivery systems, or inhalers. Additionally, the unit dose kit can contain instructions for preparation and administration of the compositions. The kit may be manufactured as a single use unit dose for one subject, multiple uses for a particular subject (at a constant dose or in which the individual compounds may vary in potency as therapy progresses); or the kit may contain multiple doses suitable for administration to multiple subjects ("bulk packaging"). The kit components may be assembled in cartons, blister packs, bottles, and tubes.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the subject. Chronic, long-term administration may be indicated.

Combination Therapies

In some embodiments, the pharmaceutical composition may further comprise an additional compound having anti-malarial activity. The additional compound having anti-malarial activity can be selected from any compound having anti-malarial activity, such as chloroquine, quinine, prymethamine, sulfadoxine, mefloquine, artemether, lumefantrine, artesunate, amodiaquine, dihydroartemisinin, piperaquine, proguanil, doxycycline, clindamycin, artemisinin, and atovaquone.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

EXAMPLES

The following Examples are intended to illustrate the synthesis of a representative number of compounds and the use of these compounds in the treatment of malaria. Accordingly, the Examples are intended to illustrate but not to limit the invention. Additional compounds not specifically exemplified may be synthesized using conventional methods in combination with the methods described herein.

Example 1

Synthesis of Compounds

The compounds of formula I can be prepared according to Schemes 1 to 9:

Compounds 1, 3, 5, 8-10, 12-13, 15, 16, 20-21, 23, 27, 33, 35-37, 39, 41-45, 49-55, 57-62, 68, 71, 78-135, 138, 139, and 141-150 can be prepared by the reactions shown in Scheme 1:

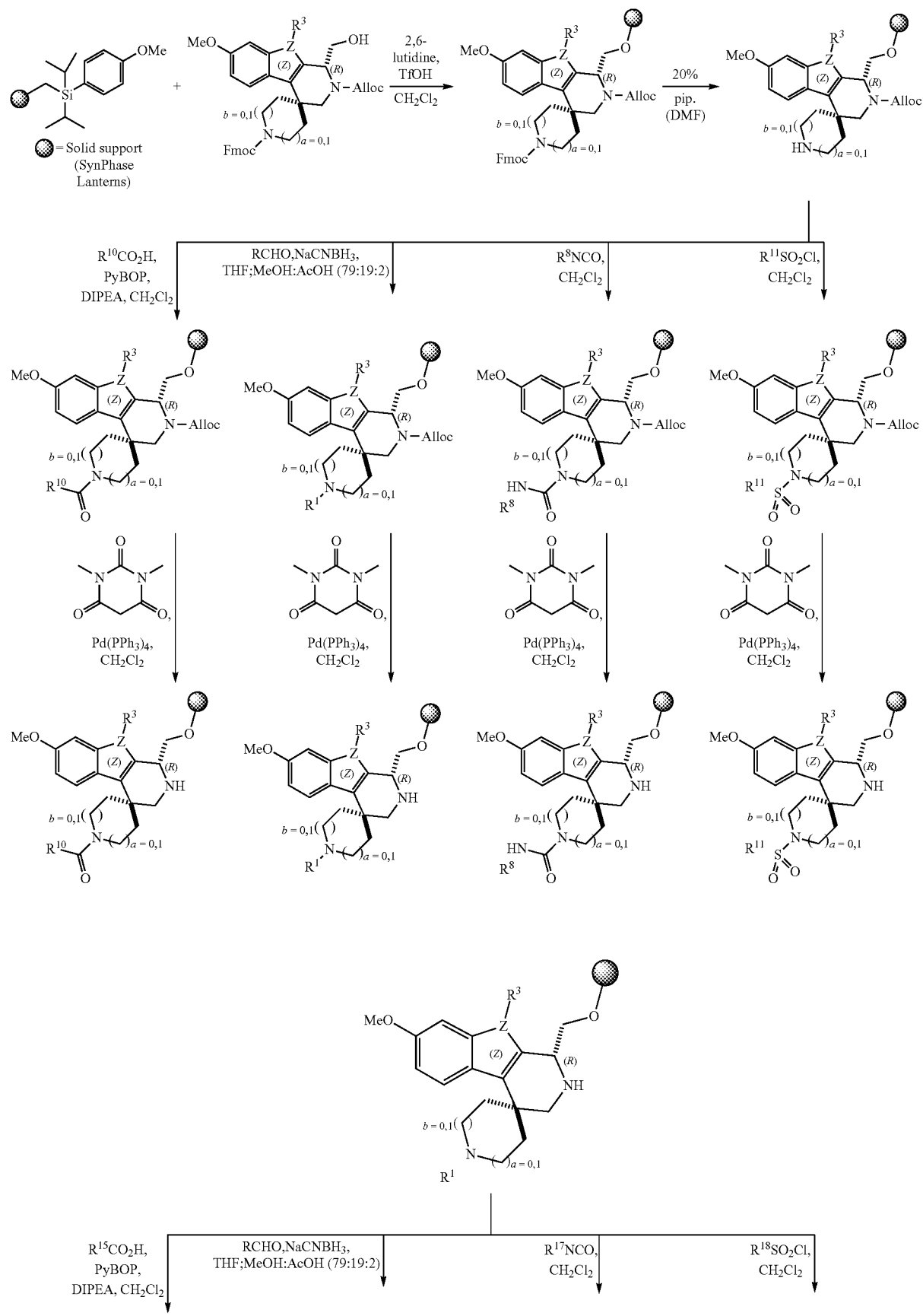

-continued
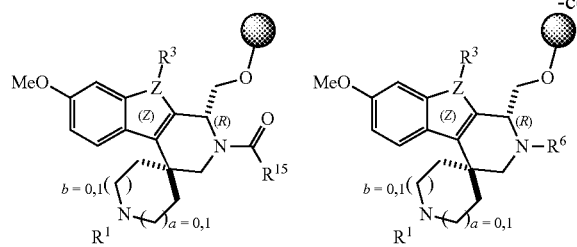
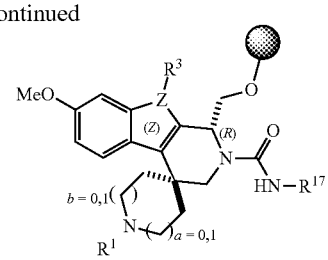
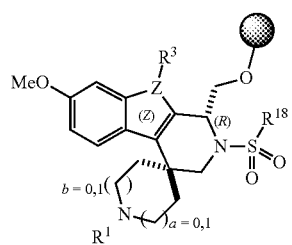
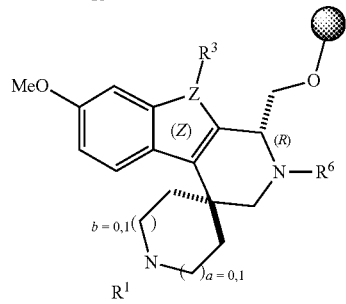
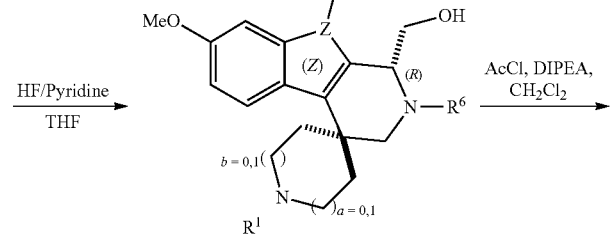
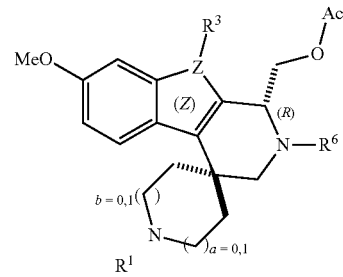
Compounds 4, 7, 17-19, 22, 24-25, 28, 29, 31, 34, 38, 46, 56, 64, 65 and 72-76 can be prepared by the reactions shown in Scheme 2:

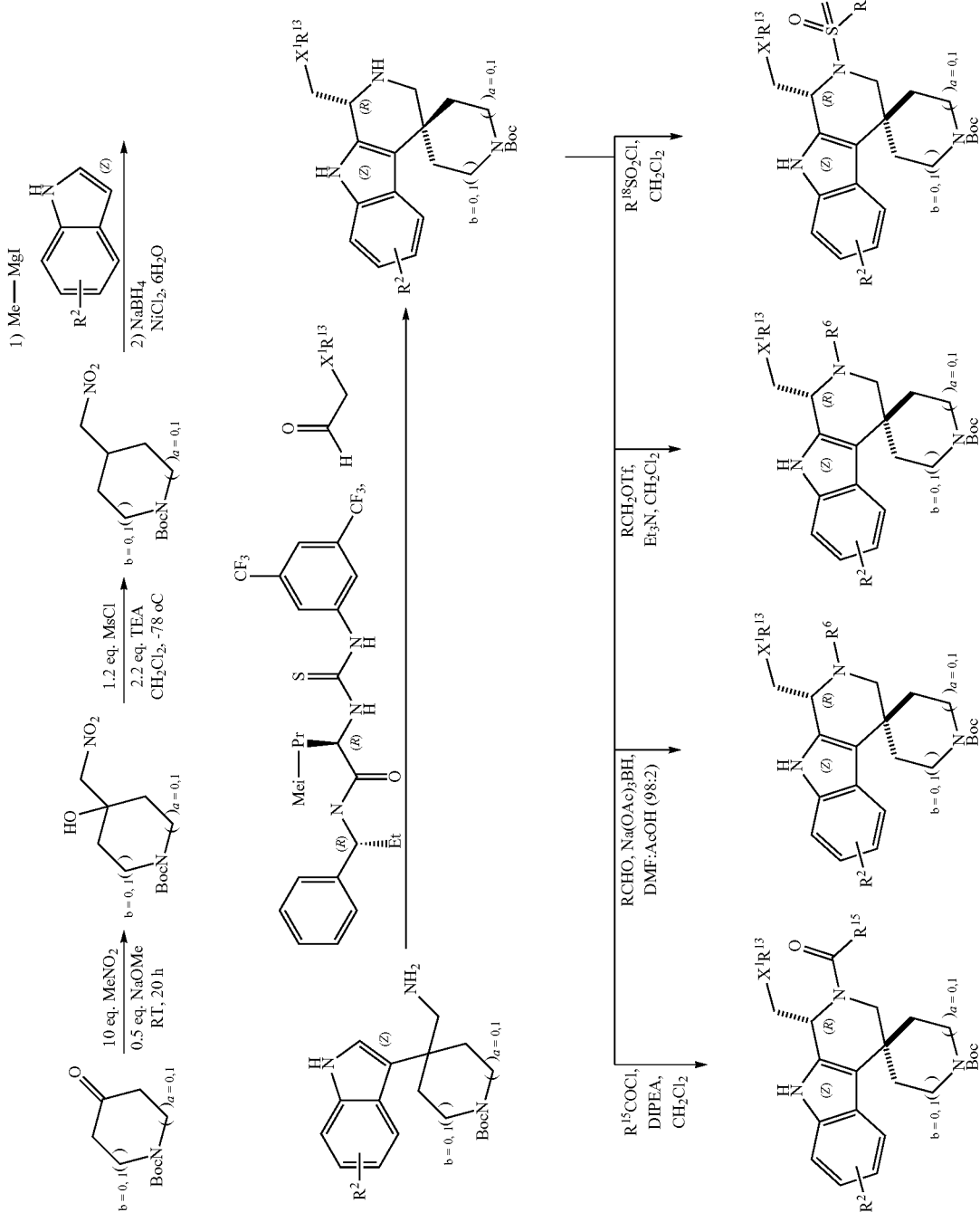

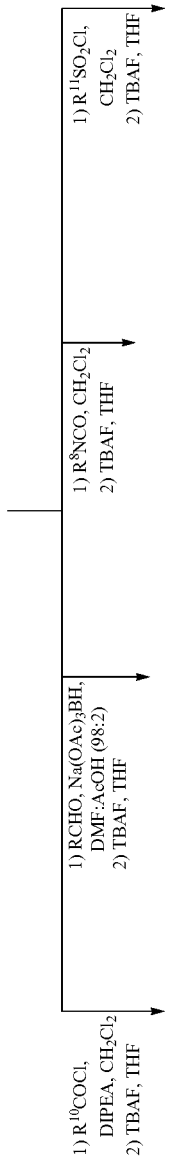
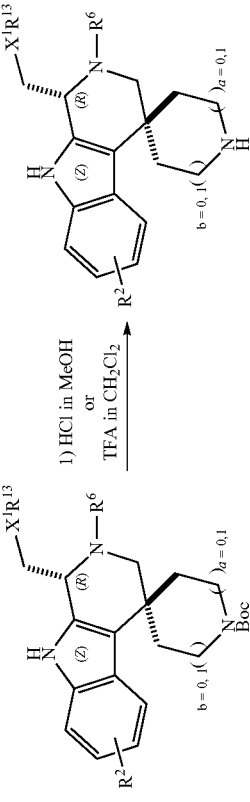
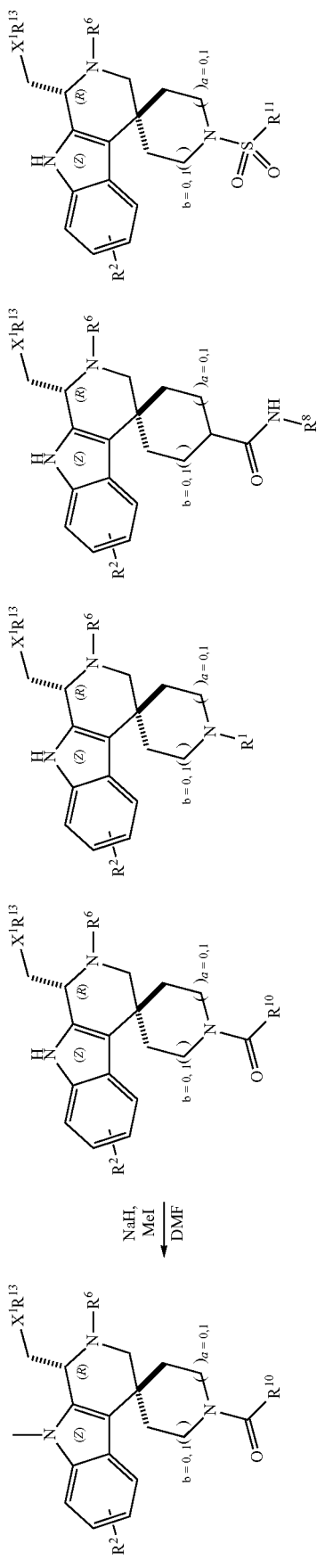

Compounds 2, 11, 14, 30, 34 and 70 can be prepared by the reactions shown in Scheme 3:
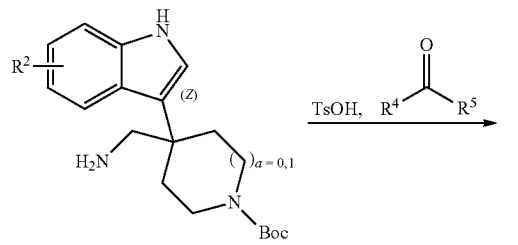
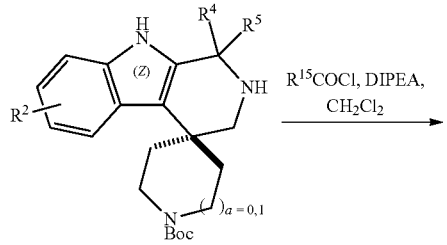
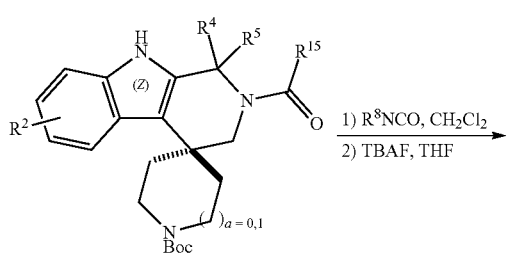
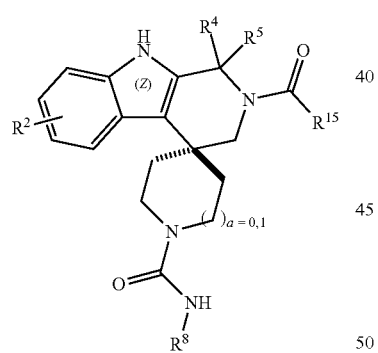
Compound 47 and 140 can be prepared by the reactions shown in Scheme 4:
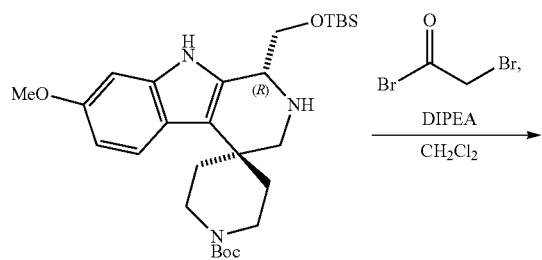
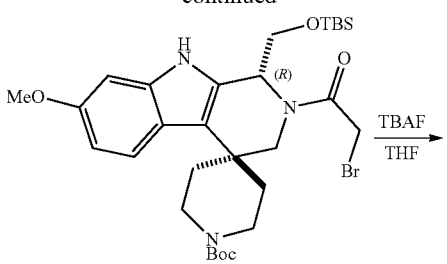
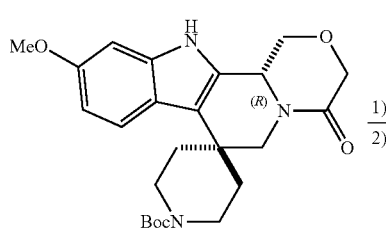
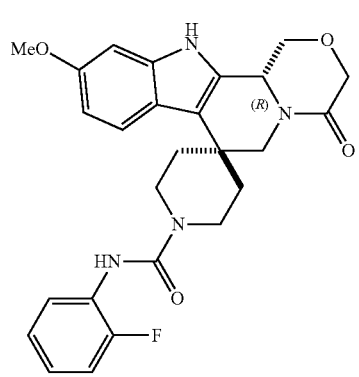
Compound 63 can be prepared according to the reactions shown in Scheme 5:
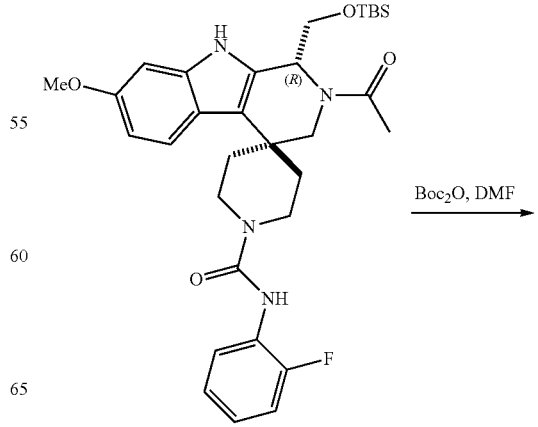

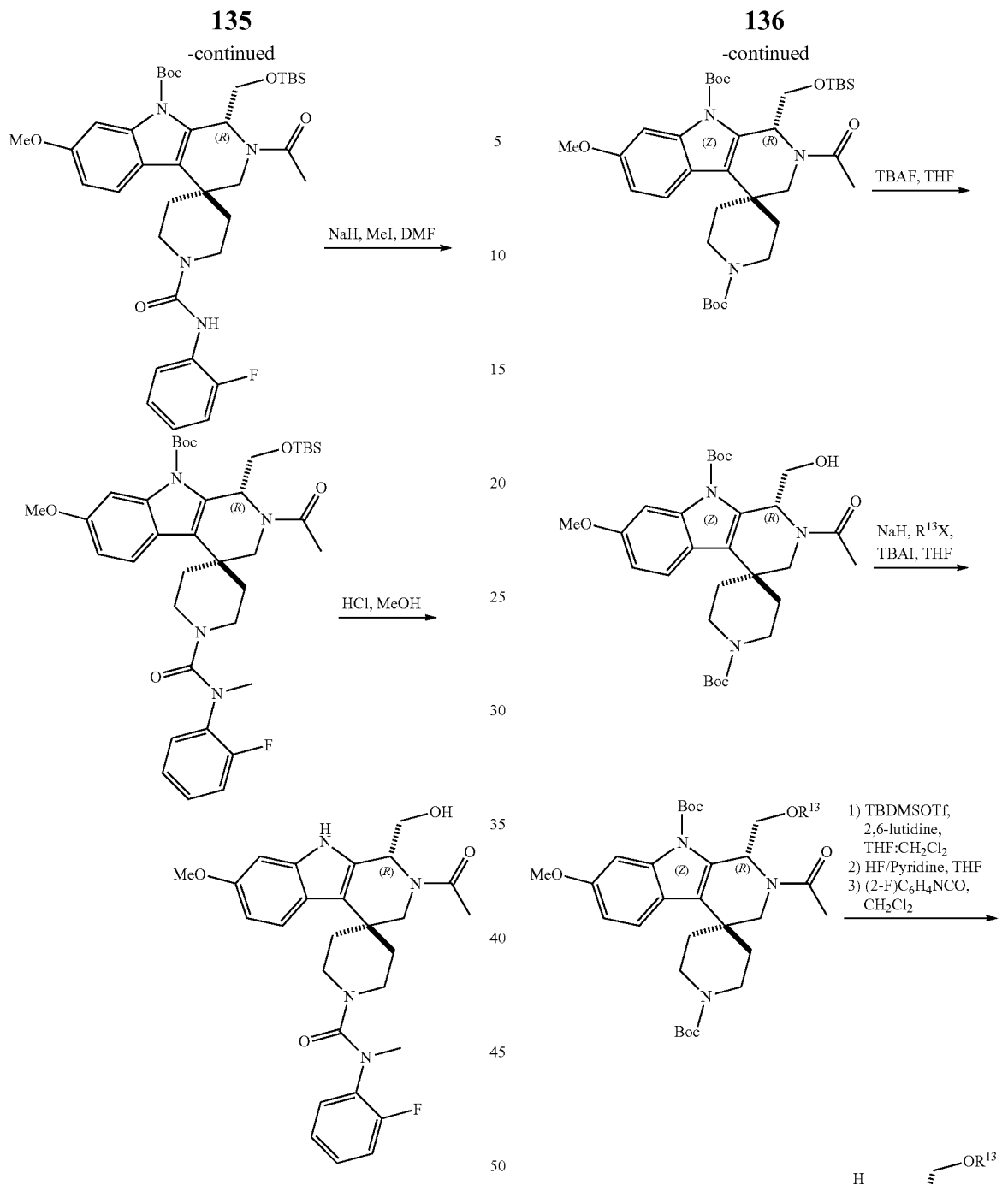
Compounds 64, 66-67 and 69 can be prepared according to the reactions shown in Scheme 6:
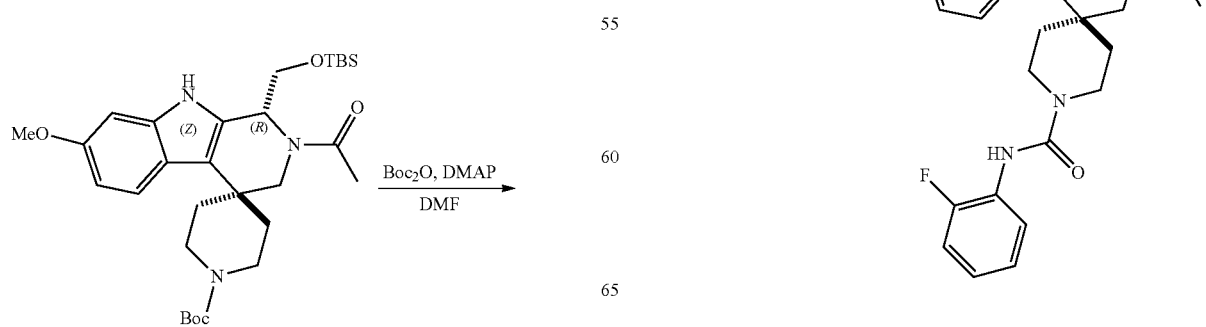

Compounds 6 and 32 can be prepared according to the reactions shown in Scheme 7:
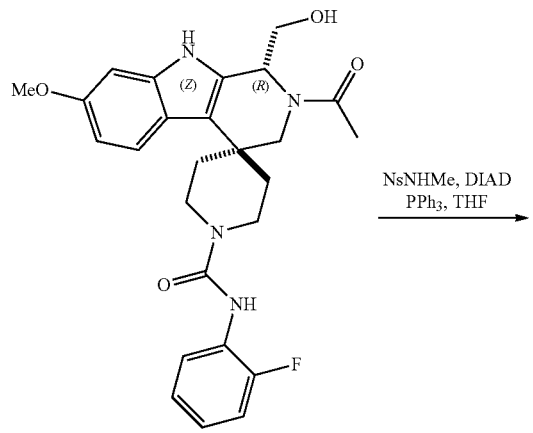
Compounds 26 and 40 can be prepared according to the reactions shown in Scheme 8:
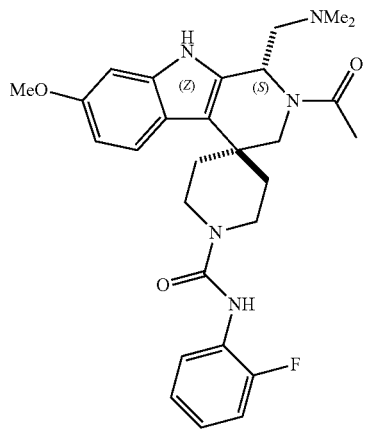
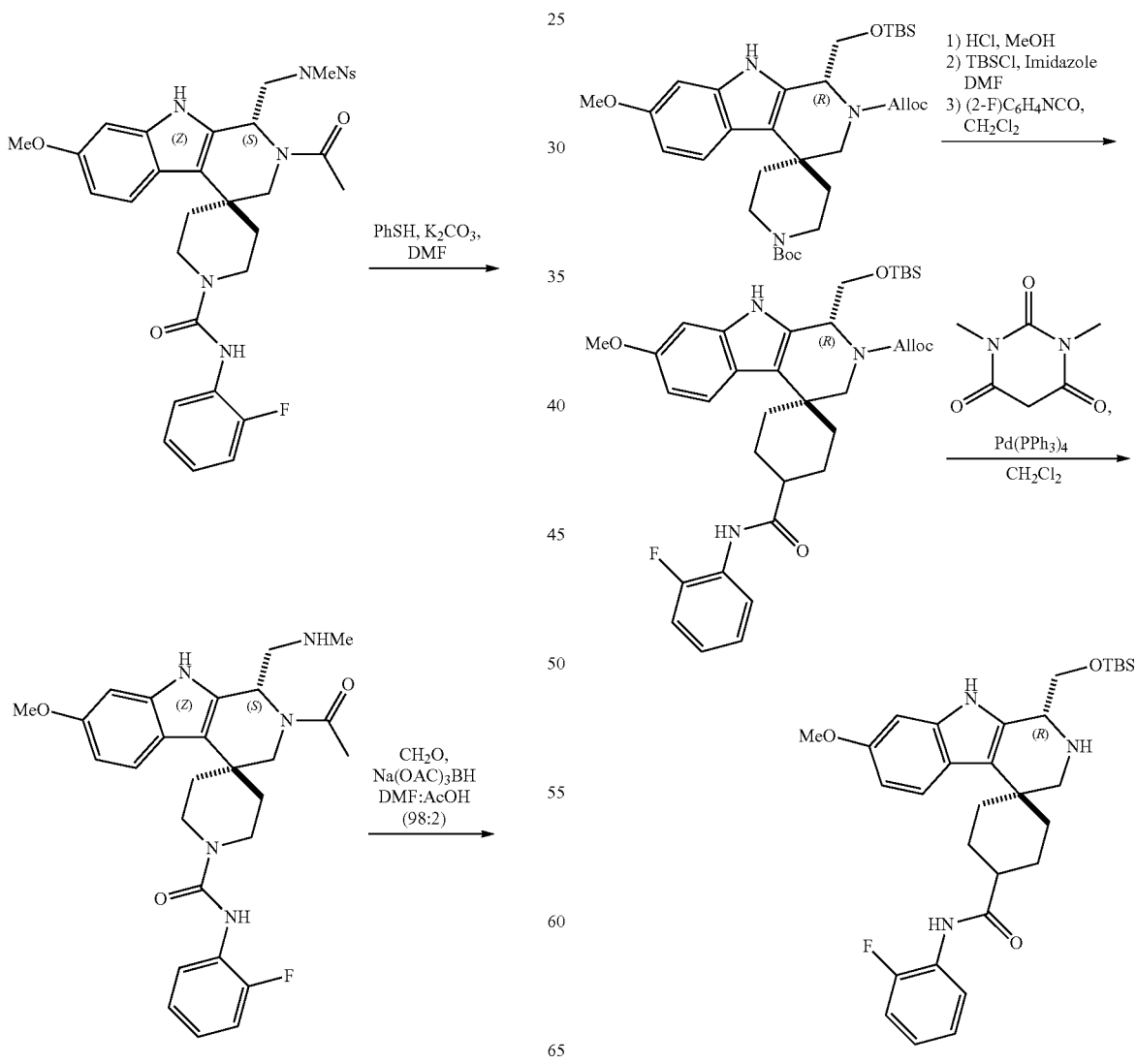

139

Compounds 77, 136, and 137 can be prepared according to the reactions shown in Scheme 9:

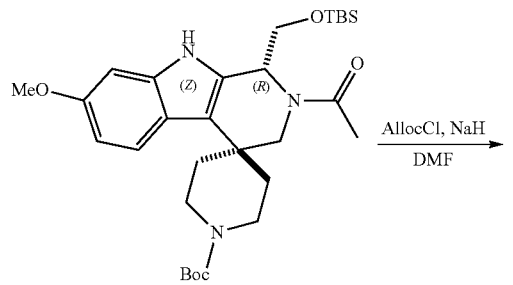

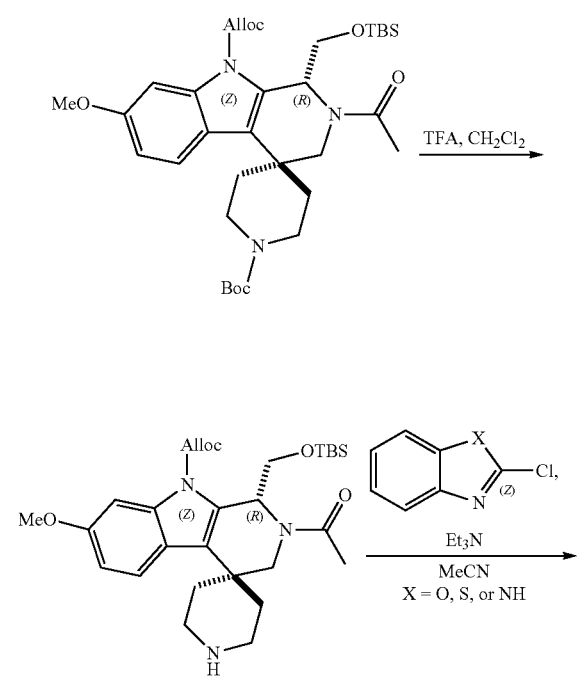

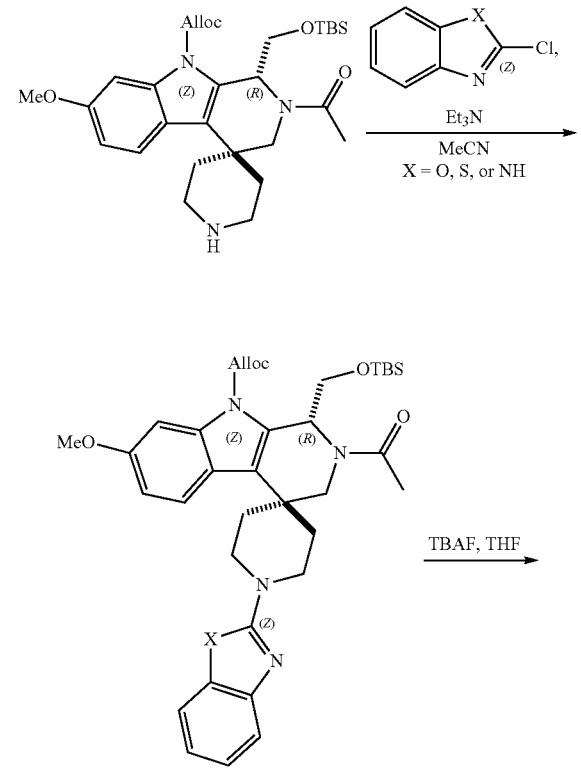

140

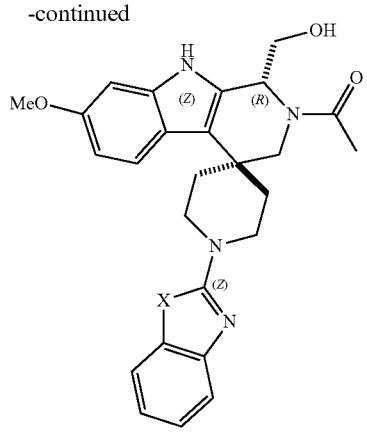

Example 2

Activity of Compounds Against the Dd2 Strain of *P. falciparum*

The Dd2 strain of *P. falciparum* was cultured in complete medium (RPMI with L-glutamine, 4.3% heat-inactivated O-positive human serum, 2.08 mg/ml albumax, 0.013 mg/ml hypoxanthine, 1.17 mg/ml glucose, 0.18% $NaHCO_3$, 0.031 M Hepes, 2.60 mM NaOH, and 0.043 mg/ml gentamicin) until the parasitemia reached 3-8%. Parasitemia was determined by checking at least 500 red blood cells from a Giemsa-stained blood smear. The Dd2 cultures along with tested O-positive red blood cells are centrifuged at room temperature at 2,000 rpm for 5 min using an Eppendorf centrifuge 581 OR with an A-4-81 rotor. The medium was aspirated off. For the compound screening, a parasite dilution at a 1% parasitemia and 1.0% hematocrit was created with screening medium (RPMI with L-glutamine, 4.16 mg/ml albumax II, 0.013 mg/ml hypoxanthine, 1.73 mg/ml glucose, 0.18% NaHCO3, 0.031M Hepes, 2.60 mM NaOH, and 0.043 mg/ml gentamicin). The suspension was gassed with 93% nitrogen, 4% carbon dioxide, and 3% oxygen and placed at 37° C. until needed. Using a liquid dispenser, 20 μl of screening medium was dispensed into 384-well, black, clear-bottom plates. With a PinTool, 100 nl of compounds dissolved in DMSO was transferred into the assay plates along with control compound (mefloquine). Next, 30 μl of the parasite suspension in screening medium was then dispensed into the assay plates such that the final parasitemia was 1%, and the final hematocrit was 1.0%. Final concentration of DMSO was 0.125%. Mefloquine at a final concentration of 20 μM and DMSO at a final concentration of 0.125% were used within the assay plates to serve as background and baseline controls, respectively. The assay plates were transferred to incubators (93% nitrogen, 4% carbon dioxide, and 3% oxygen during the 72-h incubation at 37° C.). Ten microliters of detection reagent consisting of 1 OX SYBR Green I (Invitrogen; supplied in 10,000× concentration) in lysis buffer (20 mM Tris-HCl, 5 mM EDTA, 0.16% Saponin wt/vol, 1.6% Triton X vol/vol) was dispensed into the assay plates. For optimal staining, the assay plates were left at room temperature for 24 h in the dark. The assay plates were read by using an Envision (PerkinElmer) reader, with 505 dichroic mirrors with 485-nm excitation and 530-nm emission settings, and the plate reads were from the bottom.

Results

By following the above protocol, $EC^{50}$ Dd2 results for compounds 1-150 are shown in Table 2 below.

TABLE 2

Bioactivity of Selected Compounds

| Example Number | $EC^{50}$ Dd2 (nM) | Example Number | $EC^{50}$ Dd2 (nM) | Example Number | $EC^{50}$ Dd2 (nM) |
|---|---|---|---|---|---|
| 1 | 214-345 | 51 | 177-235 | 101 | 2046 |
| 2 | 120-303 | 52 | 1450-1977 | 102 | 490 |
| 3 | 1610 | 53 | 37-118 | 103 | 182 |
| 4 | 10698 | 54 | 353-551 | 104 | 467 |
| 5 | 6485 | 55 | 321-719 | 105 | 269 |
| 6 | 183-319 | 56 | 1036-8766 | 106 | 727 |
| 7 | 1379 | 57 | 577-1209 | 107 | 2207 |
| 8 | 1770 | 58 | 1439-1600 | 108 | 1224 |
| 9 | 2908 | 59 | 1459-2889 | 109 | 1027 |
| 10 | 3384 | 60 | 4612-5793 | 110 | 779 |
| 11 | 4431 | 61 | 3777-4116 | 111 | 451 |
| 12 | 246-291 | 62 | 4487-9484 | 112 | 1101 |
| 13 | 127-162 | 63 | 1701-2920 | 113 | 1100 |
| 14 | 415 | 64 | 3620 | 114 | 951 |
| 15 | 15-178 | 65 | 882 | 115 | 1035 |
| 16 | 2405 | 66 | 422 | 116 | 1471 |
| 17 | 834 | 67 | 3037 | 117 | 1608 |
| 18 | 763 | 68 | 918-2270 | 118 | 1962 |
| 19 | 1203 | 69 | 9051 | 119 | 1722 |
| 20 | 620 | 70 | 3890 | 120 | 1647 |
| 21 | 4009 | 71 | 7240 | 121 | 360 |
| 22 | 430 | 72 | 16540 | 122 | 421 |
| 23 | 2401 | 73 | 468 | 123 | 683 |
| 24 | 1242 | 74 | 30-130 | 124 | 880 |
| 25 | 1618 | 75 | 3213 | 125 | 343 |
| 26 | 1331 | 76 | 1469 | 126 | 437 |
| 27 | 2734 | 77 | 8500 | 127 | 1787 |
| 28 | 7140 | 78 | 905 | 128 | 750 |
| 29 | 1386 | 79 | 135 | 129 | 794 |
| 30 | 7443 | 80 | 1300 | 130 | 439 |
| 31 | 571 | 81 | 130 | 131 | 892 |
| 32 | 485 | 82 | 1519 | 132 | 1667 |
| 33 | 2975 | 83 | 522 | 133 | 613 |
| 34 | 3774 | 84 | 2527 | 134 | 2968 |
| 35 | 175-410 | 85 | 1619 | 135 | 2231 |
| 36 | 423 | 86 | 96 | 136 | 2470 |
| 37 | 577 | 87 | 78 | 137 | 5760 |
| 38 | 809 | 88 | 1167 | 138 | 4501 |
| 39 | 752 | 89 | 432 | 139 | 5760 |
| 40 | 1223 | 90 | 2613 | 140 | 2470 |
| 41 | 17487 | 91 | 481 | 141 | 6708 |
| 42 | 1754-1896 | 92 | 681 | 142 | 6040 |
| 43 | 3367-5216 | 93 | 195 | 143 | 5000 |
| 44 | 1602-3279 | 94 | 929 | 144 | 1080 |
| 45 | 44-131 | 95 | 1260 | 145 | 113 |
| 46 | 2427-6328 | 96 | 2869 | 146 | 269 |
| 47 | 2232-3228 | 97 | 1642 | 147 | 391 |
| 48 | 214-236 | 98 | 98 | 148 | 8532 |
| 49 | 2389-2920 | 99 | 1881 | 149 | 221 |
| 50 | 1237-2254 | 100 | 418 | 150 | 14-58 |

Example 3

In Vitro *P. falciparum* Blood-Stage Culture and Assay

Strains of *Plasmodium falciparum* (Dd2, 3D7, D6, K1, NF54, V1/3, HB3, 7G8, FCB, TM90C2B) were obtained from Malaria Research and Reference Reagent Resource Center (MR4). *P. falciparum* isolates were maintained with O-positive human blood in an atmosphere of 93% $N_2$, 4% $CO_2$, 3% $O_2$ at 37° C. in complete culturing medium (10.4 g/L RPMI 1640, 5.94 g/L HEPES, 5 g/L albumax II, 50 mg/L hypoxanthine, 2.1 g/L sodium bicarbonate, 10% human serum and 43 mg/L gentamicin). Parasites were cultured in medium until the parasitemia reached 3-8%. Parasitemia was determined by checking at least 500 red blood cells from a Giemsa-stained blood smear. For the compound screening, a parasite suspension at 2.0% parasitemia and 2.0% hematocrit was created with medium. 25 μl of medium was dispensed into 384-well, black, clear-bottom plates. 100 nl of compounds in DMSO was transferred into the assay plates along with control compound (mefloquine). Next, 25 μl of the parasite suspension in medium was dispensed into the assay plates such that the final parasitemia was 1% and the final hematocrit was 1%. The assay plates were incubated for 72 hours at 37° C. 10 μl of detection reagent consisting of 10×SYBR Green I (Invitrogen; supplied at 10,000× concentration) in lysis buffer (20 mM Tris-HCl, 5 mM EDTA, 0.16% Saponin wt/vol, 1.6% Tritonx vol/vol) was dispensed into the assay plates. For optimal staining, the assay plates were left at room temperature for 24 h in the dark. The assay plates were read with 505 dichroic mirrors with 485-nm excitation and 530-nm emission settings.

Results

Compound 15 was found to be equipotent against all field isolates (see Table 3).

TABLE 3

Activity of compound 15 against multiple drug resistant strains of *P. falciparum*

| Strain | Dd2 | 3D7 | D6 | K1 | NF54 | V1/3 | HB3 | 7G8 | FCB | TM90C2B |
|---|---|---|---|---|---|---|---|---|---|---|
| Activity ($IC_{50}$ nM) | 73 | 65 | 70 | 91 | 88 | 98 | 147 | 113 | 130 | 104 |

Example 4

Activity Against Different Stages of *P. falciparum, P. Berghei* and *P. Cynomolgi*

In vitro *P. berghei* liver-stage assay HepG2 cells were maintained in DMEM, 10% (vol/vol) FBS (Sigma), and 1% (vol/vol) antibiotic-antimycotic in a standard tissue culture incubator (37° C., 5% $CO_2$). *P. berghei* (ANKA GFP-luc)

infected *Anopheles stephensi* mosquitoes were obtained from the New York University Langone Medical Center Insectary (New York). For assays, ~17,500 HepG2 cells per well were added to a 384-well microtiter plate in duplicate. After 18-24 h at 37° C. the media was exchanged and compounds were added. After 1 hour, parasites obtained from freshly dissected mosquitoes were added to the plates (4,000 parasites per well), the plates were spun for 10 min at 1,000 rpm, and then the plates were incubated at 37° C. The final assay volume was 30 µL. After a 48 hour incubation at 37° C., Bright-Glo (Promega) was added to the parasite plate to measure relative luminescence. The relative signal intensity of each plate was evaluated with an EnVision (PerkinElmer) system.

In Vitro *P. cynomolgi* Liver Stage Assay

An in vitro *P. cynomolgi* liver stage assay was performed as described in Zeeman et al. Antimicrobial Agents and Chemotherapy, 2014, 58:1586-1595. 96-well plates are seeded with freshly isolated or thawed cryopreserved stocks of primary rhesus monkey hepatocytes one or two days before infection with $5 \times 10^4$ freshly dissected *P. cynomolgisporozoites* per well. After 2-3 h of sporozoite invasion into the hepatocytes, culture medium is exchanged for culture medium containing appropriate compound dilutions. Initially, compounds are tested in duplicate in 3 dilutions: 0.1, 1 and 10 µM. Plates are incubated for 6 days with medium exchange (including compound dilutions) every other day. Plates are fixed in methanol and parasites are stained with rabbit anti-PcyHSP70 antiserum in the presence of DAPI to stain the nuclei. Plates are automatically counted in a high-content imager (Operetta®) and small parasites (hypnozoites, s.f.) and large schizonts (l.f.) are recorded, as well as number of hepatocytes as a measure for cytotoxic effects of the compounds. Controls include uninfected hepatocytes, sporozoite infected wells without compound and infected wells with primaquine and atovaquone. When activity is recorded and reported, a more extensive dilution curve can be evaluated: a 7-point 3-fold dilution series from days 0-6.

*P. falciparum* Gametocyte Viability Assay

*P. falciparum* 3D7 stage Ill-V gametocytes were isolated by discontinuous Percoll gradient centrifugation of parasite cultures treated with 50 mM N-acetyl-D-glucosamine for 3 days to kill asexual parasites. Gametocytes ($1.0 \times 10^5$) were seeded in 96-well plates and incubated with compounds for 72 hours. In vitro anti-gametocyte activity was measured using Cell-titer glo (Promega).

Results

Compound 15 was found to inhibit the asexual stage and the sexual and transmission stage of the parasites (see Table 4).

TABLE 4

Activity of Compound 15 against different stages of Plasmodium ($IC_{50}$s reported in nM)

| erythrocytic stage (*P. falciparum*) | | exo-erythrocytic stage | |
|---|---|---|---|
| asexual | sexual (IV & V) | *P. berghei* | *P. cynomolgi* (s.f/l.f) |
| 64 | 643 | 459 | 344/832 |

Example 5

In Vivo *P. berghei* Blood-Stage Assay

CD-1 mice (n=4 per experimental group; female; 6-7-week-old; 20-24 g) were inoculated with $1 \times 10^6$ *P. berghei* (ANKA GFP-luc) blood stage parasites intravenously 24 hours before treatment and compounds were administered orally (at 0 hour). Parasitemia was monitored by the In vivo Imaging System (IVIS 100, Xenogen; Caliper Life Sciences) to acquire the bioluminescence signal. In addition, blood smear samples were obtained from each mouse on day 4 after inoculation, stained with Giemsa, and viewed under a microscope for visual detection of blood parasitemia. Animals with parasitemia exceeding 20% were euthanized.

Results

Compound 15 was found to inhibit the blood stage of *P. berghei* in vivo (see Table 5).

TABLE 5

In vivo activity of Compound 15 in blood-stage assay

| Dosage mg/kg | | Parasitized RBC over 100 | | | % of | | Mouse survival in days | | | Avg. Mouse |
|---|---|---|---|---|---|---|---|---|---|---|
| 4x | Route | M1 | M2 | M3 | control | % Activity | M1 | M2 | M3 | survival |
| 50 | T/E p.o. | 3.70 | 3.20 | 2.80 | 5.80 | 94.20 | 6 | 6 | 7 | 6.3 |

T/E = 7% Tween, 3% Ethanol, and 90% water

Example 6

In Vivo *P. berghei* Liver-Stage Assay

CD-1 mice (n=4 per experimental group; female; 6-7-week-old; 20-24 g) were inoculated intravenously with $1 \times 10^5$ freshly isolated *P. berghei*(ANKA GFP-luc) sporozoites intravenously, and compounds were administered orally at 50 mg/kg two hours later. Bioluminescence signals from the transgenic parasites were monitored by the In vivo Imaging System (IVIS 100, Xenogen; Caliper Life Sciences). Animals with parasitemia exceeding 20% were euthanized.

Results

Compound 15 was found to inhibit the liver stage of *P. berghei* in vivo (FIG. 1). Untreated control animals showed systemic (blood stage) parasitemia by day four, while atovaquone or Compound treated animals remained parasite free.

OTHER EMBODIMENTS

While the invention has been described in connection with specific embodiments thereof, it will be understood that

What is claimed:

1. A compound according to Formula (I):

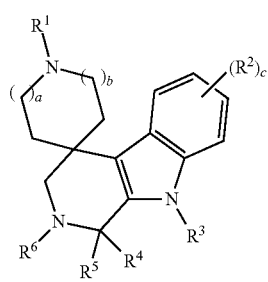

Formula I wherein a and b are independently 0, 1, or 2;
c is 0, 1, 2, 3, or 4;
$R^1$ is hydrogen, $C_1$-$C_6$ alkyl, $C_2$-$C_9$ heteroaryl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, —C(O)NR$^7$R$^8$, —C(O)OR$^9$, —C(O)R$^{10}$, or —S(O)$_2$R$^{11}$;
each $R^2$ is independently hydroxyl, halogen, or —OR$^{12}$;
$R^3$ is hydrogen or $C_1$-$C_6$ alkyl;
$R^4$ is hydrogen or $C_1$-$C_6$ alkyl;
$R^5$ is $C_1$-$C_6$ alkyl, or —(CH$_2$)$_n$X$^1$R$^{13}$, or $R^5$ and $R^6$ together with the carbon and nitrogen atoms to which they are respectively attached, combine to form a 5-8-membered heterocycle;
$R^6$ is hydrogen, $C_1$-$C_6$ alkyl, $C_1$-$C_6$ perfluoroalkyl, $C_3$-$C_{10}$ carbocyclyl $C_1$-$C_6$ alkyl, $C_6$-$C_{10}$ aryl $C_1$-$C_6$ alkyl, $C_2$-$C_9$ heteroaryl $C_1$-$C_6$ alkyl, $C_2$-$C_9$ heterocyclyl $C_1$-$C_6$ alkyl, N-protecting group, —C(O)R$^{15}$, —C(O)NR$^{16}$R$^{17}$, or —S(O)$_2$R$^{18}$;
$R^7$ is hydrogen or $C_1$-$C_6$ alkyl;
$R^8$ is $C_6$-$C_{10}$ aryl, $C_2$-$C_9$ heteroaryl, $C_2$-$C_9$ heterocyclyl, or $C_3$-$C_{10}$ carbocyclyl;
$R^9$ is $C_1$-$C_6$ alkyl or $C_6$-$C_{10}$ aryl;
$R^{10}$ is $C_1$-$C_6$ alkyl, $C_6$-$C_{10}$ aryl, $C_2$-$C_9$ heterocyclyl, $C_6$-$C_{10}$ aryl $C_1$-$C_6$ alkyl, or $C_2$-$C_9$ heteroaryl $C_1$-$C_6$ alkyl;
$R^{11}$ is $C_1$-$C_6$ alkyl, $C_6$-$C_{10}$ aryl, or $C_6$-$C_{10}$ aryl $C_1$-$C_6$ alkyl;
each $R^{12}$ is $C_1$-$C_6$ alkyl or $C_1$-$C_6$ acyl;
n is 1, 2, 3, 4, 5, or 6;
$X^1$ is absent, O, or NR$^{14}$;
$R^{13}$ is hydrogen, $C_1$-$C_6$ alkyl, $C_1$-$C_6$ heteroalkyl, $C_1$-$C_6$ perfluoroalkyl, $C_1$-$C_6$ acyl, $C_6$-$C_{10}$ aryl $C_1$-$C_6$ alkyl, an O- or N-protecting group, or $R^{13}$ and $R^{14}$ combine to form a 5-8-membered heterocycle;
$R^{14}$ is hydrogen or $C_1$-$C_6$ alkyl;
$R^{15}$ is $C_1$-$C_6$ alkyl, $C_1$-$C_6$ perfluoroalkyl, $C_1$-$C_6$ heteroalkyl, $C_3$-$C_{10}$ carbocyclyl, $C_2$-$C_9$ heterocyclyl, $C_6$-$C_{10}$ aryl, $C_6$-$C_{10}$ aryl $C_1$-$C_6$ alkyl;
$R^{16}$ and $R^{17}$ are independently hydrogen, $C_1$-$C_6$ alkyl, or $C_6$-$C_{10}$ aryl; and
$R^{18}$ is $C_1$-$C_6$ alkyl, $C_1$-$C_6$ perfluoroalkyl, $C_3$-$C_{10}$ carbocyclyl, or $C_6$-$C_{10}$ aryl;
wherein the compound is not compound 12, compound 15, or any one of compounds 78-135 of Table 1,
or a pharmaceutically acceptable salt thereof.

2. The compound of claim 1, wherein the compound has a structure of Formula II:

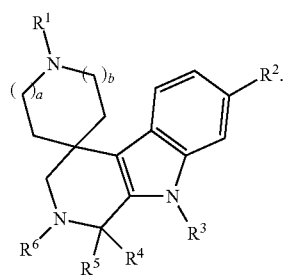

Formula II

3. The compound of claim 1, wherein c is 2.

4. The compound of claim 3, wherein the compound has a structure of Formula III:

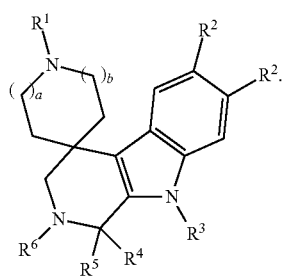

Formula III

5. The compound of claim 1, wherein the compound has a structure of Formula IV:

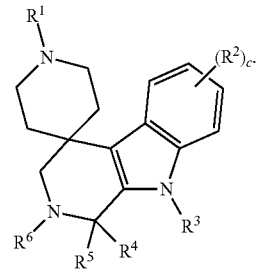

Formula IV

6. The compound of claim 5, wherein said compound has the structure:

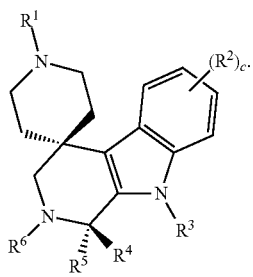

7. The compound of claim 1, wherein the compound has a structure of Formula V:

Formula V

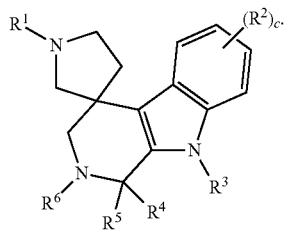

8. The compound of claim 7, wherein the compound has the structure:

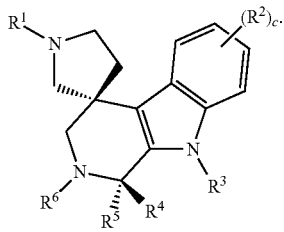

9. The compound of claim 1, wherein the compound has a structure of Formula VI:

Formula VI

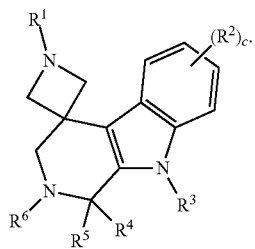

10. The compound of claim 9, wherein the compound has the structure:

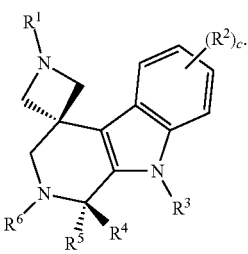

11. The compound of claim 1, wherein $R^5$ and $R^6$ together with the carbon and nitrogen atoms to which they are respectively attached, combine to form a 5-8-membered heterocycle.

12. The compound of claim 11, wherein the compound has the structure of Formula VII:

Formula VII

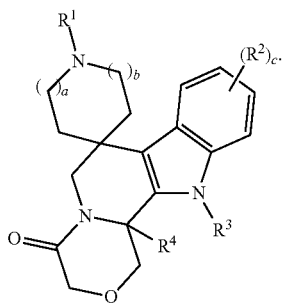

13. The compound of claim 1, wherein R6 is hydrogen, C1-C6 alkyl, C3-C10 carbocyclyl C1-C6 alkyl, C6-C10 aryl C1-C6 alkyl, C2-C9 heteroaryl C1-C6 alkyl, C2-C9 heterocyclyl C1-C6 alkyl, an N-protecting group, —C(O)R15, C(O)NR16R17, or —S(O)2R18.

14. A compound selected from any one of compounds 1 to 11, 13, 14, 16 to 77, or 136 to 150 of Table 1 or a pharmaceutically acceptable salt thereof.

15. A pharmaceutical composition, comprising a therapeutically effective amount of a compound of claim 1 or any one of compounds 12, 15, or 78-135 of Table 1 and a pharmaceutically acceptable excipient.

16. A method of treating malaria in a subject, comprising the step of administering to the subject an effective amount of claim 1, any one of compounds 12, 15, or 78-135 of Table 1, or a composition of claim 15 to a patient in need thereof.

17. The method of claim 16, wherein said malaria is drug resistant malaria.

18. The method of claim 17, wherein said drug resistant malaria is resistant to chloroquine, quinine, prymethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof.

19. The method of claim 16, wherein said malaria is liver stage malaria.

20. The method of claim 16, wherein the liver of said subject is infected with a malaria-causing parasite and said treatment prevents spread of said infection from their liver.

21. The method of claim 16, wherein the compound is compound 15.

* * * * *